(12) United States Patent
Watanabe et al.

(10) Patent No.: US 9,108,957 B2
(45) Date of Patent: Aug. 18, 2015

(54) 3-[1,4]OXAZEPANE-4-PYRIMIDONE DERIVATIVES

(75) Inventors: Kazutoshi Watanabe, Tokyo (JP);
Kazuki Nakayama, Kanagawa (JP);
Daiki Sakai, Kanagawa (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 366 days.

(21) Appl. No.: 13/262,396

(22) PCT Filed: Apr. 1, 2010

(86) PCT No.: PCT/JP2010/056346
§ 371 (c)(1),
(2), (4) Date: Dec. 19, 2011

(87) PCT Pub. No.: WO2010/114179
PCT Pub. Date: Oct. 7, 2010

(65) Prior Publication Data
US 2012/0095216 A1    Apr. 19, 2012

(30) Foreign Application Priority Data
Apr. 2, 2009 (JP) ................................. 2009-105674

(51) Int. Cl.
*A61K 31/553* (2006.01)
*C07D 401/14* (2006.01)
*C07D 403/14* (2006.01)
*C07D 413/14* (2006.01)

(52) U.S. Cl.
CPC ............ *C07D 413/14* (2013.01); *C07D 401/14* (2013.01); *C07D 403/14* (2013.01)

(58) Field of Classification Search
CPC .. A61K 31/553; C07D 401/14; C07D 403/14; C07D 413/14
USPC ...................... 514/211.15; 540/544
See application file for complete search history.

(56) References Cited

U.S. PATENT DOCUMENTS

| | | | |
|---|---|---|---|
| 7,256,199 B1 | 8/2007 | Watanabe et al. | |
| 2003/0187004 A1 | 10/2003 | Almario Garcia et al. | |
| 2005/0090490 A1 | 4/2005 | Uehara et al. | |
| 2005/0130967 A1 | 6/2005 | Uehara et al. | |

FOREIGN PATENT DOCUMENTS

| | | |
|---|---|---|
| EP | 0 616 032 | 3/1994 |
| EP | 1115721 | 7/2001 |
| EP | 1136482 | 9/2001 |
| EP | 1136483 | 9/2001 |
| JP | 2003-528095 A | 9/2003 |
| WO | 01/70729 | 9/2001 |
| WO | 03/027080 | 4/2003 |
| WO | 03/037888 | 5/2003 |
| WO | 2007/119463 A1 | 10/2007 |
| WO | 2008/023239 A1 | 2/2008 |

OTHER PUBLICATIONS

E.P.O. Office action, mail date is Jul. 1, 2013.
Search report from International Preliminary Report on Patentability and Written Opinion for PCT/JP2010/056346, mail date is Oct. 4, 2011.
Search report from International Application No. PCT/JP2010/056346, mail date is Jun. 14, 2010.
Japanese Office Action issued with respect to Japanese Application No. 2011-542382, mail date is Nov. 19, 2013.

*Primary Examiner* — Brenda Coleman
(74) *Attorney, Agent, or Firm* — Greenblum & Bernstein, P.L.C.

(57) ABSTRACT

A compound represented by the formula (I) or a pharmaceutically acceptable salt thereof:

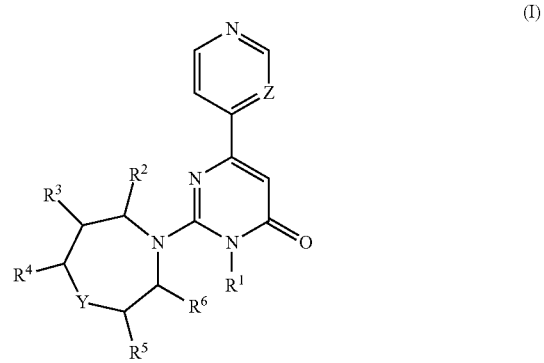

wherein Z represents nitrogen atom, C—F or the like; $R^1$ represents a $C_1$-$C_3$ alkyl group;
Y represents oxygen atom or N—$R^7$; $R^2$, $R^3$, $R^4$, $R^5$, $R^6$ and $R^7$ each independently represents hydrogen atom, a $C_1$-$C_6$ alkyl group, or a group represented by the formula (II):

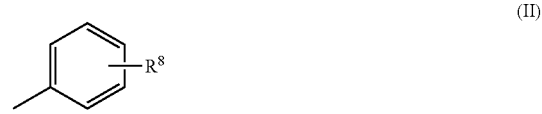

which is used for preventive and/or therapeutic treatment of a disease caused by tau protein kinase 1 hyperactivity such as a neurodegenerative diseases (e.g. Alzheimer disease).

4 Claims, No Drawings

3-[1,4]OXAZEPANE-4-PYRIMIDONE DERIVATIVES

TECHNICAL FIELD

The present invention relates to compounds that are useful as an active ingredient of a medicament for preventive and/or therapeutic treatment of diseases mainly caused by abnormal activity of tau protein kinase 1 (TPK1 also called GSK3beta: glycogen synthase kinase 3 beta), such as neurodegenerative diseases (e.g. Alzheimer disease).

BACKGROUND ART

Alzheimer disease is progressive senile dementia, in which marked cerebral cortical atrophy is observed due to degeneration of nerve cells and decrease of nerve cell number. Pathologically, numerous senile plaques and neurofibrillary tangles are observed in brain. The number of patients has been increased with the increment of aged population, and the disease arises a serious social problem. Although various theories have been proposed, a cause of the disease has not yet been elucidated. Early resolution of the cause has been desired.

It has been known that the degree of appearance of two characteristic pathological changes of Alzheimer disease well correlates to the degree of intellectual dysfunction. Therefore, researches have been conducted from early 1980's to reveal the cause of the disease through molecular level investigations of components of the two pathological changes. Senile plaques accumulate extracellularly, and β amyloid protein has been elucidated as their main component (abbreviated as "Aβ" hereinafter in the specification: Biochem. Biophys. Res. Commun., 120, 885 (1984); EMBO J., 4, 2757 (1985); Proc. Natl. Acad. Sci. USA, 82, 4245 (1985)). In the other pathological change, i.e., the neurofibrillary tangles, a double-helical filamentous substance called paired helical filament (abbreviated as "PHF" hereinafter in the specification) accumulate intracellularly, and tau protein, which is a kind of microtubule-associated protein specific for brain, has been revealed as its main component (Proc. Natl. Acad. Sci. USA, 85, 4506 (1988); Neuron, 1, 827 (1988)).

Furthermore, on the basis of genetic investigations, presenilins 1 and 2 were found as causative genes of familial Alzheimer disease (Nature, 375, 754 (1995); Science, 269, 973 (1995); Nature. 376, 775 (1995)), and it has been revealed that presence of mutants of presenilins 1 and 2 promotes the secretion of Aβ (Neuron, 17, 1005 (1996); Proc. Natl. Acad. Sci. USA, 94, 2025 (1997)). From these results, it is considered that, in Alzheimer disease, Aβ abnormally accumulates and agglomerates due to a certain reason, which engages with the formation of PHF to cause death of nerve cells. It is also expected that extracellular outflow of glutamic acid and activation of glutamate receptor responding to the outflow may possibly be important factors in an early process of the nerve cell death caused by ischemic cerebrovascular accidents.

It has been reported that kainic acid treatment that stimulates the AMPA receptor, one of glutamate receptor, increases mRNA of the amyloid precursor protein (abbreviated as "APP" hereinafter in the specification) as a precursor of Aβ (Society for Neuroscience Abstracts, 17, 1445 (1991)), and also promotes metabolism of APP (The Journal of Neuroscience, 10, 2400 (1990)). Therefore, it has been strongly suggested that the accumulation of Aβ is involved in cellular death due to ischemic cerebrovascular disorders. Other diseases in which abnormal accumulation and agglomeration of Aβ are observed include, for example, Down syndrome, cerebral bleeding due to solitary cerebral amyloid angiopathy, Lewy body disease and the like. Furthermore, as diseases showing neurofibrillary tangles due to the PHF accumulation, examples include progressive supranuclear palsy, subacute sclerosing panencephalitic parkinsonism, postencephalitic parkinsonism, pugilistic encephalitis, Guam parkinsonism-dementia complex, Lewy body disease and the like.

The tau protein is generally composed of a group of related proteins that forms several bands at molecular weights of 48-65 kDa in SDS-polyacrylamide gel electrophoresis, and it promotes the formation of microtubules. It has been verified that tau protein incorporated in the PHF in the brain suffering from Alzheimer disease is abnormally phosphorylated compared with usual tau protein (J. Biochem., 99, 1807 (1986); Proc. Natl. Acad. Sci. USA, 83, 4913 (1986)). An enzyme catalyzing the abnormal phosphorylation has been isolated. The protein was named as tau protein kinase 1 (abbreviated as "TPK1" hereinafter in the specification), and its physicochemical properties have been elucidated (J. Biol. Chem., 267, 10897 (1992)). Moreover, cDNA of rat TPK1 was cloned from a rat cerebral cortex cDNA library based on a partial amino acid sequence of TPK1, and its nucleotide sequence was determined and an amino acid sequence was deduced. As a result, it has been revealed that the primary structure of the rat TPK1 corresponds to that of the enzyme known as rat GSK-3β (glycogen synthase kinase 3β, FEBS Lett., 325, 167 (1993)).

It has been reported that Aβ, the main component of senile plaques, is neurotoxic (Science, 250, 279 (1990)). However, various theories have been proposed as for the reason why Aβ causes the cell death, and any authentic theory has not yet been established. Takashima et al. observed that the cell death was caused by Aβ treatment of fetal rat hippocampus primary culture system, and then found that the TPK1 activity was increased by Aβ treatment and the cell death by Aβ was inhibited by antisense of TPK1 (Proc. Natl. Acad. Sci. USA, 90, 7789 (1993); EP616032).

In view of the foregoing, compounds which inhibit the TPK1 activity may possibly suppress the neurotoxicity of Aβ and the formation of PHF and inhibit the nerve cell death in the Alzheimer disease, thereby cease or defer the progress of the disease. The compounds may also be possibly used as a medicament for therapeutic treatment of ischemic cerebrovascular disorder, Down syndrome, cerebral amyloid angiopathy, cerebral bleeding due to Lewy body disease and the like by suppressing the cytotoxicity of Aβ. Furthermore, the compounds may possibly be used as a medicament for therapeutic treatment of neurodegenerative diseases such as progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration and frontotemporal dementia, vascular dementia, traumatic injuries, brain and spinal cord trauma, peripheral neuropathies, retinopathies and glaucoma, as well as other diseases such as non-insulin dependent diabetes, obesity, manic depressive illness, schizophrenia, alopecia, breast cancer, non-small cell lung carcinoma, thyroid cancer, T or B-cell leukemia, and several virus-induced tumors.

From the point of view described above, the discovery of potent TPK1 inhibitor may lead to the effective drug for the treatment of Alzheimer's disease and many structurally diverse classes of compounds with in vitro TPK1 inhibitory activity have been already disclosed. However, design of novel structures for the TPK1 inhibitor is expected to lead to clinically more efficient compounds through several improvements in in vitro and in vivo activities, kinase selectivity, ADME, PK/PD profiles and physical properties.

As structurally similar compounds to the compounds of the present invention represented by formula (I) described later, the compounds disclosed in the International Publication Nos. WO01/70729, WO03/037888 and WO03/027080 are known, which have amino components bearing chainlike, six membered ring or five membered ring. On the other hand, the pharmacological profiles of seven membered ring like [1,4] oxazepane ring shared among the compounds of the present invention have not been known commonly because of synthetically challenging structures. The changing ring size may bring about the higher inhibitory activity of the protein by adjusted direction of functional groups to the amino acid residue of the protein and vice versa. On the other hand, the more flexible seven membered ring structures may also lead to decrease the inhibitory activity because of the attenuation of interaction between the compound and the protein caused by the increase of entropy. Additionally, the compounds bearing seven-membered ring like [1,4]oxazepane are expected to be more lipophilic than six membered ring like morpholine. The increasing lipophilicity often tends to induce CYP inhibition which is one of the factors to drop the compounds off from clinical stage. Despite the prediction described above, the compounds of the present invention presented by formula (I) described later show the high inhibitory activity to TPK1 and improve CYP inhibition (especially, CYP1A2 and CYP2D6).

CITATION LIST

Patent Literature

EP616032
WO01/70729
WO03/037888
WO03/027080

Non Patent Literature

Biochem. Biophys. Res. Commun., 120, 885 (1984)
EMBO J., 4, 2757 (1985)
Proc. Natl. Acad. Sci. USA, 82, 4245 (1985)
Proc. Natl. Acad. Sci. USA, 85, 4506 (1988)
Neuron, 1, 827 (1988)
Nature, 375, 754 (1995)
Science, 269, 973 (1995)
Nature. 376, 775 (1995)
Neuron, 17, 1005 (1996)
Proc. Natl. Acad. Sci. USA, 94, 2025 (1997)
Society for Neuroscience Abstracts, 17, 1445 (1991)
The Journal of Neuroscience, 10, 2400 (1990)
J. Biochem., 99, 1807 (1986)
Proc. Natl. Acad. Sci. USA, 83, 4913 (1986)
J. Biol. Chem., 267, 10897 (1992)
FEBS Lett., 325, 167 (1993)
Science, 250, 279 (1990)
Proc. Natl. Acad. Sci. USA, 90, 7789 (1993)

SUMMARY OF INVENTION

Technical Problem

An object of the present invention is to provide a compound useful as an active ingredient of a medicament for preventive and/or therapeutic treatment of diseases such as Alzheimer disease, which has high clinical efficacy and can be administered with other medicament. More specifically, the object is to provide a novel compound useful as an active ingredient of a medicament that enables radical prevention and/or treatment of the neurodegenerative diseases such as Alzheimer disease by inhibiting the TPK1 activity to suppress the neurotoxicity of Aβ and the formation of the PHF and by inhibiting the death of nerve cells, which has high clinical efficacy and can be administered with other medicament.

Solution to Problem

In order to achieve the foregoing object, the inventors of the present invention conducted synthesis of compounds represented by the general formula (I) and screening their in vitro TPK1 inhibitory activities. As a result, they found that a novel compound represented by the following formula (I) had the desired activity. The present invention was achieved on the basis of these findings.

The present invention thus provides;
1. A compound represented by the following formula (I) or a pharmaceutically acceptable salt thereof:

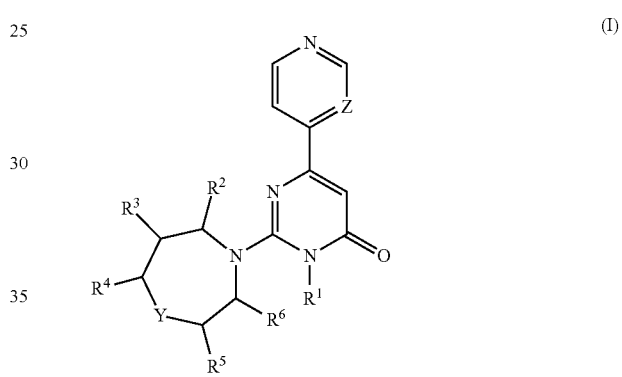

(I)

wherein Z represents nitrogen atom or C—X;
X represents hydrogen atom or a halogen atom;
$R^1$ represents a $C_1$-$C_8$ alkyl group;
Y represents oxygen atom or N—$R^7$;
$R^2$, $R^3$, $R^4$, $R^5$, $R^6$ and $R^7$ may be the same or different and each independently represents hydrogen atom, a $C_1$-$C_8$ alkyl group, or a group represented by the following formula (II):

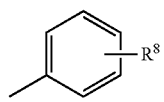

(II)

wherein $R^8$ represents hydrogen atom, a halogen atom, cyano group, nitro group, a $C_1$-$C_6$ alkyl group, or a group represented by any one of the following formulas (IIIa) to (IIIh):

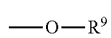

(IIIa)

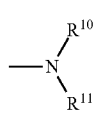

(IIIb)

-continued

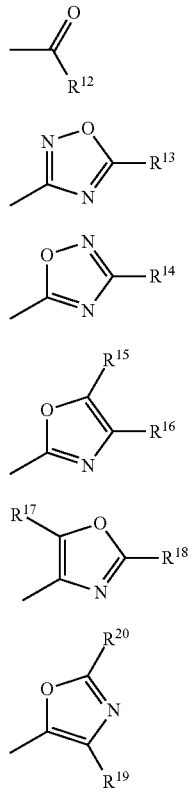

wherein R⁹ represents hydrogen atom or a $C_1$-$C_6$ alkyl group;
$R^{11}$, $R^{13}$, $R^{14}$, $R^{15}$, $R^{16}$, $R^{17}$, $R^{18}$, $R^{19}$ and $R^{20}$ may be the same or different and each independently represents hydrogen atom, a $C_1$-$C_6$ alkyl group, or a $C_6$-$C_{10}$ is aryl group;
$R^{12}$ represents hydrogen atom, hydroxyl group, amino group, a $C_1$-$C_6$ alkyl group, a $C_1$-$C_3$ alkyloxy group, a $C_1$-$C_3$ alkylamino group, a di($C_1$-$C_3$ alkyl)amino group, or a $C_6$-$C_{10}$ aryl group;
$R^{10}$ represents hydrogen atom or a group represented by the following formula (IV):

-A-R²¹                  (IV)

wherein A represents —$(CH_2)_p$—, —CO—, or —$SO_2$—, wherein p represents an integer of 1 to 3;
$R^{21}$ represents hydrogen atom, a $C_1$-$C_6$ alkyl group, —$OR^{22}$, —$NR^{23}R^{24}$, or a $C_6$-$C_{10}$ aryl group:
wherein $R^{22}$, $R^{23}$ and $R^{24}$ may be the same or different and each independently represents hydrogen atom, a $C_1$-$C_6$ alkyl group, a $C_1$-$C_6$ alkenyl group, or a $C_6$-$C_{10}$ aryl-methyl group;
or $R^{10}$ and $R^{11}$ may be combined to each other to form a heterocyclic group together with the nitrogen atom to which $R^{10}$ and $R^{11}$ bind to.

2. The compound or a pharmaceutically acceptable salt thereof according to the above 1, wherein Z is nitrogen atom or C—F.

3. The compound or a pharmaceutically acceptable salt thereof according to the above 1 or 2, wherein Y is oxygen atom and each of at least four substituents selected from the group consisting of $R^2$, $R^3$, $R^4$, $R^5$ and $R^6$ is hydrogen atom.

4. The compound or a pharmaceutically acceptable salt thereof according to any one of the above 1 to 3, wherein $R^2$, $R^3$, $R^4$, $R^5$ and $R^6$ may be the same or different and is each independently hydrogen atom, a $C_1$-$C_6$ alkyl group or a group represented by the formula (II), wherein $R^8$ is hydrogen atom, a halogen atom, cyano group, a $C_1$-$C_6$ alkyl group, or a group represented by any one of the formula (IIIa), (IIId), and (IIIe).

5. The compound or a pharmaceutically acceptable salt thereof according to the above 1 or 2, wherein Y is N—$R^7$ and each of $R^2$, $R^3$, $R^4$, $R^5$ and $R^6$ is hydrogen atom.

6. A compound which is selected from the group consisting of:
(S)-2-[6-(4-Bromo-phenyl)-[1,4]oxazepan-4-yl]-1-methyl-1H-[4,4']bipyrimidinyl-6-one;
2-(6-phenyl-[1,4]oxazepan-4-yl)-1-methyl-1H-[4,4']bipyrimidinyl-6-one;
6-(3-Fluoro-pyridin-4-yl)-3-methyl-2-(2-phenyl-[1,4]oxazepan-4-yl)-3H-pyrimidin-4-one;
(S)-2-[6-(4-cyano-phenyl)-[1,4]oxazepan-4-yl]-1-methyl-1H-[4,4']bipyrimidinyl-6-one;
(S)-4-{4-[4-(3-Fluoro-pyridin-4-yl)-1-methyl-6-oxo-1,6-dihydro-pyrimidin-2-yl]-[1,4]oxazepan-2-yl}-benzamide;
(S)-2-[2-(3-Bromo-phenyl)-[1,4]oxazepan-4-yl]-6-(3-fluoro-pyridin-4-yl)-3-methyl-3H-pyrimidin-4-one;
(S)-2-[2-(4-Bromo-phenyl)-[1,4]oxazepan-4-yl]-1-methyl-1H-[4,4']bipyrimidinyl-6-one;
(+)-6-(3-Fluoro-pyridin-4-yl)-3-methyl-2-[7-(4-[1,2,4]oxadiazol-3-yl-phenyl)-[1,4]oxazepan-4-yl]-3H-pyrimidin-4-one;
6-(3-Fluoro-pyridin-4-yl)-3-methyl-2-(5-phenyl-[1,4]oxazepan-4-yl)-3H-pyrimidin-4-one;
(S)-2-[2-(4-Bromo-phenyl)-[1,4]oxazepan-4-yl]-6-(3-fluoro-pyridin-4-yl)-3-methyl-3H-pyrimidin-4-one;
6-(3-Fluoro-pyridin-4-yl)-3-methyl-2-{6-[4-(3-methyl-[1,2,4]oxadiazol-5-yl)-phenyl]-[1,4]oxazepan-4-yl}-3H-pyrimidin-4-one;
(S)-2-[2-(4-Fluoro-phenyl)-[1,4]oxazepan-4-yl]-6-(3-fluoro-pyridin-4-yl)-3-methyl-3H-pyrimidin-4-one;
(+)-6-(3-Fluoro-pyridin-4-yl)-3-methyl-2-{7-[4-(3-methyl-[1,2,4]oxadiazol-5-yl)-phenyl]-[1,4]oxazepan-4-yl}-3H-pyrimidin-4-one;
(S)-3-{4-[4-(3-Fluoro-pyridin-4-yl)-1-methyl-6-oxo-1,6-dihydro-pyrimidin-2-yl]-[1,4]oxazepan-2-yl}-benzamide;
(+)-6-(3-Fluoro-pyridin-4-yl)-3-methyl-2-{7-[4-(5-methyl-[1,2,4]oxadiazol-3-yl)-phenyl]-[1,4]oxazepan-4-yl}-3H-pyrimidin-4-one;
6-(3-Fluoro-pyridin-4-yl)-3-methyl-2-[6-(4-[1,2,4]oxadiazol-3-yl-phenyl)-[1,4]oxazepan-4-yl]-3H-pyrimidin-4-one;
(S)-2-[2-(3-Bromo-phenyl)-[1,4]oxazepan-4-yl]-1-methyl-1H-[4,4']bipyrimidinyl-6-one;
(S)-2-[2-(4-cyano-phenyl)-[1,4]oxazepan-4-yl]-6-(3-fluoro-pyridin-4-yl)-3-methyl-3H-pyrimidin-4-one;
2-[7-(2-Fluoro-phenyl)-[1,4]oxazepan-4-yl]-6-(3-fluoro-pyridin-4-yl)-3-methyl-3H-pyrimidin-4-one;
(S)-2-[2-(4-Fluoro-phenyl)-[1,4]oxazepan-4-yl]-1-methyl-1H-[4,4']bipyrimidinyl-6-one;
(S)-3-[4-(1-Methyl-6-oxo-1,6-dihydro-[4,4']bipyrimidinyl-2-yl)-[1,4]oxazepan-2-yl]-benzamide;
6-(3-Fluoro-pyridin-4-yl)-2-[7-(3-methoxy-phenyl)-[1,4]oxazepan-4-yl]-3-methyl-3H-pyrimidin-4-one;
6-(3-Fluoro-pyridin-4-yl)-3-methyl-2-(5-methyl-[1,4]oxazepan-4-yl)-3H-pyrimidin-4-one; and
(R)-6-(3-Fluoro-pyridin-4-yl)-3-methyl-2-(5-methyl-[1,4]oxazepan-4-yl)-3H-pyrimidin-4-one;
or a pharmaceutically acceptable salt thereof.

7. A medicament comprising as an active ingredient the compound or a pharmaceutically acceptable salt thereof according to any one of the above 1 to 6.

8. The medicament according to the above 7 which is used for preventive and/or therapeutic treatment of a disease caused by tau protein kinase 1 hyperactivity.

9. The medicament according to the above 7 which is used for preventive and/or therapeutic treatment of a neurodegenerative disease.

10. The medicament according to the above 9, wherein the disease is selected from the group consisting of non-insulin dependent diabetes, obesity, manic depressive illness, schizophrenia, alopecia, breast cancer, non-small cell lung carcinoma, thyroid cancer, T or B-cell leukemia, and a virus-induced tumor.

11. The medicament according to the above 9, wherein the neurodegenerative disease is selected from the group consisting of Alzheimer disease, ischemic cerebrovascular accidents, Down syndrome, cerebral bleeding due to cerebral amyloid angiopathy, progressive supranuclear palsy, subacute sclerosing panencephalitic parkinsonism, postencephalitic parkinsonism, pugilistic encephalitis, Guam parkinsonism-dementia complex, Lewy body disease, Pick's disease, corticobasal degeneration, frontotemporal dementia, vascular dementia, traumatic injuries, brain and spinal cord trauma, peripheral neuropathies, retinopathies, glaucoma, amyotrophic lateral sclerosis, malaria, Pemphigus vulgaris, and neutropenia induced by cancer chemotherapy.

DESCRIPTION OF EMBODIMENTS

Unless otherwise indicated, the following definitions are set forth to illustrate and defined the meaning and scope of the various terms used to describe the invention herein.

The term "$C_1$-$C_3$ alkyl group" means an alkyl group having 1 to 3 carbon atoms which may be either linear or branched. The examples of $C_1$-$C_3$ alkyl group include methyl group, ethyl group, n-propyl group, and isopropyl group. A $C_1$-$C_3$ alkyl group moiety of substituents containing a $C_1$-$C_3$ alkyl moiety mentioned in the specification, such as a $C_1$-$C_3$ alkyloxy group, a $C_1$-$C_3$ alkylamino group, or a di($C_1$-$C_3$ alkyl) amino group, has the same meaning. The $C_1$-$C_3$ alkyl group represented by $R^1$ is preferably methyl group.

The term "$C_1$-$C_6$ alkyl group" means an alkyl group having 1 to 6 carbon atoms which may be either linear or branched. The examples of $C_1$-$C_6$ alkyl group include methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, and isohexyl group.

The term "halogen atom" means chlorine atom, bromine atom, fluorine atom, or iodine atom.

The term "heterocyclic group" in the specification means a cyclic group derived from a nitrogen-containing heterocyclic ring. Examples of the heterocyclic ring include pyrrole, pyrroline, pyrrolidine, imidazole, imidazoline, imidazolidine, pyrazole, pyrazoline, pyrazolidine, triazole, tetrazole, pyridine, pyridine oxide, piperidine, pyrazine, piperazine, pyrimidine, pyridazine, piperidine, azepane, morpholine, and homopiperazine. The bond position in the cycle is any one of the nitrogen atoms included in the heterocyclic ring.

The symbol "Z" in the aforementioned formula (I) is preferably nitrogen atom, C—H, or C—F, more preferably nitrogen atom or C—F.

The seven-membered ring substituted at 2-position of the pyrimidone ring in the aforementioned formula (I) may be non-substituted or substituted with one or more substituents. The substituent may be present as $R^2$, $R^3$, $R^4$, $R^5$, $R^6$, or $R^7$ in the aforementioned formula (I).

Preferably, the seven-membered ring is non-substituted or substituted with one substituent:
when Y represents oxygen atom, each of at least four of $R^2$, $R^3$, $R^4$, $R^5$ and $R^6$ is preferably hydrogen atom; and
when Y represents N—$R^7$, preferably each of at least five of $R^2$, $R^3$, $R^4$, $R^5$, $R^6$ and $R^7$ is hydrogen atom, and more preferably each of $R^2$, $R^3$, $R^4$, $R^5$, and $R^6$ is hydrogen atom.

The position of $R^8$ on the phenyl group in the aforementioned formula (II) is not particularly limited, and the meta- or para-position is preferable.

$R^8$ is preferably hydrogen atom, bromine atom, fluorine atom, cyano group, methyl group, or a group represented by formula (IIIa), (IIId), or (IIIe). In formula (IIIa), $R^9$ is preferably methyl group. In formula (IIIc), $R^{12}$ is preferably amino group. In formula (IIId), $R^{13}$ is preferably hydrogen atom or methyl group. In formula (IIIe), $R^{14}$ is preferably hydrogen atom or methyl group.

The pharmaceutically acceptable salt of the compound represented by the aforementioned formula (I) may include the salt with inorganic acid such as hydrochloric acid, hydrobromic acid and the like and the salt with organic acid such as acetic acid, propionic acid, tartaric acid, fumaric acid, maleic acid, malic acid, oxalic acid, succinic acid, citric acid, benzoic acid and the like.

In addition to the compound represented by the aforementioned formula (I), a pharmaceutically acceptable salt thereof, solvates thereof and hydrates thereof can also be used. The compound represented by the aforementioned formula (I) may have one or more asymmetric carbon atoms. As for the stereochemistry of such asymmetric carbon atoms, they may independently be in either (R) or (S) configuration, and the compound may exist as stereoisomers such as optical isomers, or diastereoisomers. Any stereoisomers of pure form, any mixtures of stereoisomers, racemates and the like fall within the scope of the present invention.

Examples of preferred compounds of the present invention are shown in the table 1 set out below. However, the scope of the present invention is not limited by the following compounds.

TABLE 1

| A001 | 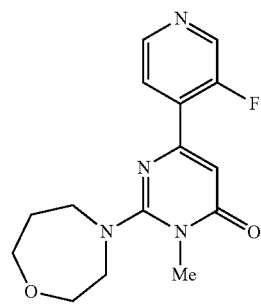 [SMILES: Cn1c(N2CCCOCC2)nc(-c2ccncc2F)cc1=O] | 6-(3-fluoropyridin-4-yl)-3-methyl-2-(1,4-oxazepan-4-yl)pyrimidin-4(3H)-one |
| --- | --- | --- |

TABLE 1-continued
| | | |
|---|---|---|
| A002 | 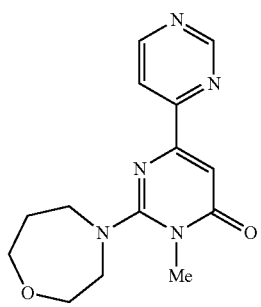 [SMILES: Cn1c(N2CCCOCC2)nc(-c2ccncn2)cc1=O] | 2-(1,4-oxazepan-4-yl)-3-methyl-6-(pyrimidin-4-yl)pyrimidin-4(3H)-one |
| A003 | 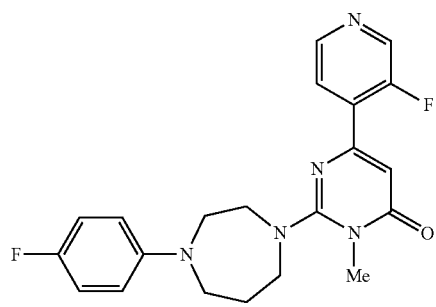 [SMILES: Cn1c(N2CCCN(c3ccc(F)cc3)CC2)nc(-c2ccncc2F)cc1=O] | 2-[4-(4-fluorophenyl)-1,4-diazepan-1-yl]-6-(3-fluoropyridin-4-yl)-3-methylpyrimidin-4(3H)-one |
| A004 | 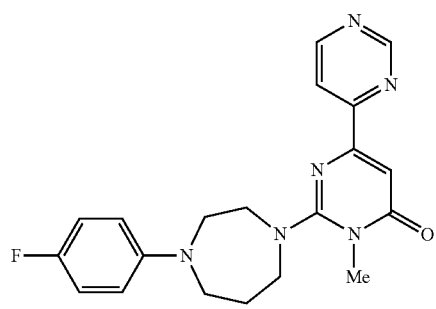 | 2-[4-(4-fluorophenyl)-1,4-diazepan-1-yl]-3-methyl-6-(pyrimidin-4-yl)pyrimidin-4(3H)-one |
| A005 | 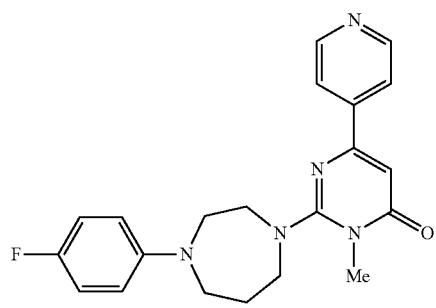 [SMILES: Cn1c(N2CCCN(c3ccc(F)cc3)CC2)nc(-c2ccncc2)cc1=O] | 2-[4-(4-fluorophenyl)-1,4-diazepan-1-yl]-3-methyl-6-(pyridin-4-yl)pyrimidin-4(3H)-one |
| A006 | 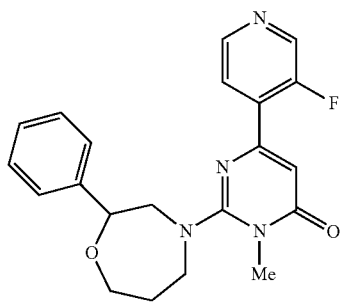 [SMILES: Cn1c(N2CCCOC(c3ccccc3)C2)nc(-c2ccncc2F)cc1=O] | 2-(2-phenyl-1,4-oxazepan-4-yl)-6-(3-fluoropyridin-4-yl)-3-methylpyrimidin-4(3H)-one |

TABLE 1-continued

| | | |
|---|---|---|
| A007 | 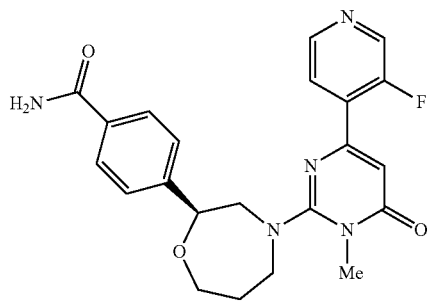 [SMILES: Cn1c(N2CCCO[C@@H](c3ccc(C(N)=O)cc3)C2)nc(-c2ccncc2F)cc1=O] | (S)-2-[2-(4-aminocarbonylphenyl)-1,4-oxazepan-4-yl]-6-(3-fluoropyridin-4-yl)-3-methylpyrimidin-4(3H)-one |
| A008 | 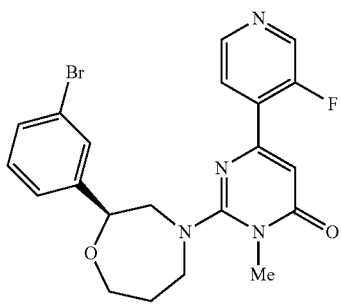 [SMILES: Cn1c(N2CCCO[C@@H](c3cccc(Br)c3)C2)nc(-c2ccncc2F)cc1=O] | (S)-2-[2-(3-bromophenyl)-1,4-oxazepan-4-yl]-6-(3-fluoropyridin-4-yl)-3-methylpyrimidin-4(3H)-one |
| A009 | 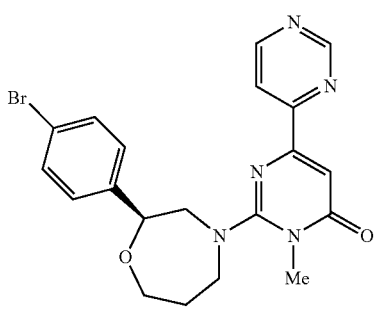 | (S)-2-[2-(4-bromophenyl)-1,4-oxazepan-4-yl]-3-methyl-6-(pyrimidin-4-yl)pyrimidin-4(3H)-one |
| A010 | 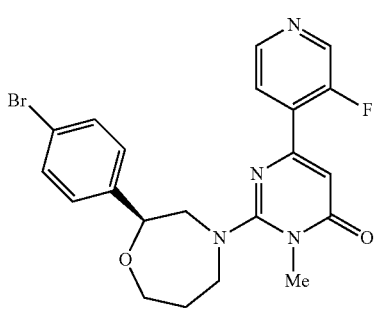 [SMILES: Cn1c(N2CCCO[C@@H](c3ccc(Br)cc3)C2)nc(-c2ccncc2F)cc1=O] | (S)-2-[2-(4-bromophenyl)-1,4-oxazepan-4-yl]-6-(3-fluoropyridin-4-yl)-3-methylpyrimidin-4(3H)-one |
| A011 | 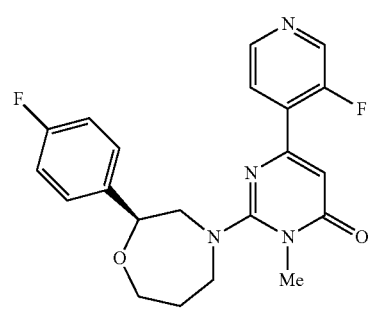 [SMILES: Cn1c(N2CCCO[C@@H](c3ccc(F)cc3)C2)nc(-c2ccncc2F)cc1=O] | (S)-2-[2-(4-fluorophenyl)-1,4-oxazepan-4-yl]-6-(3-fluoropyridin-4-yl)-3-methylpyrimidin-4(3H)-one |

TABLE 1-continued

| | | |
|---|---|---|
| A012 | 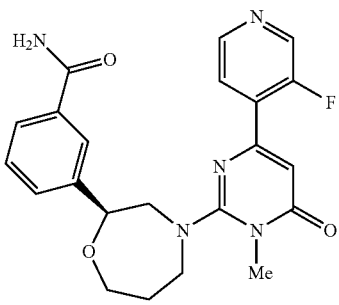 [SMILES: Cn1c(N2CCCO[C@@H](c3cccc(C(N)=O)c3)C2)nc(-c2ccncc2F)cc1=O] | (S)-2-[2-(4-aminocarbonylphenyl)-1,4-oxazepan-4-yl]-6-(3-fluoropyridin-4-yl)-3-methylpyrimidin-4(3H)-one |
| A013 | 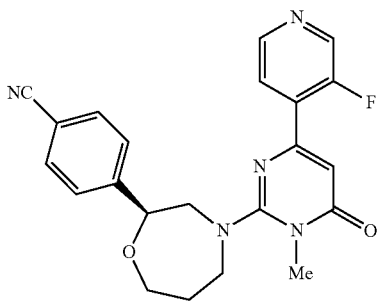 [SMILES: Cn1c(N2CCCO[C@@H](c3ccc(C#N)cc3)C2)nc(-c2ccncc2F)cc1=O] | (S)-2-[2-(4-cyanophenyl)-1,4-oxazepan-4-yl]-6-(3-fluoropyridin-4-yl)-3-methylpyrimidin-4(3H)-one |
| A014 | 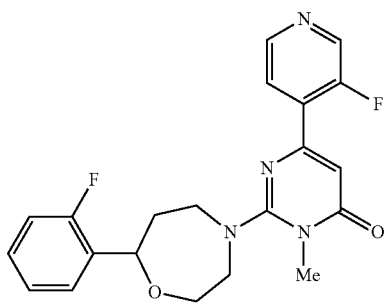 [SMILES: Cn1c(N2CCOC(c3ccccc3F)CC2)nc(-c2ccncc2F)cc1=O] | 2-[7-(2-fluorophenyl)-1,4-oxazepan-4-yl]-6-(3-fluoropyridin-4-yl)-3-methylpyrimidin-4(3H)-one |
| A015 | 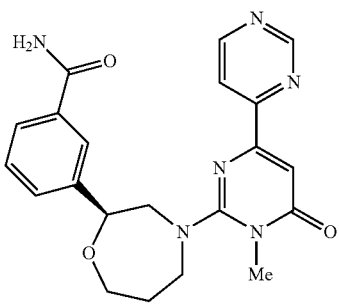 [SMILES: Cn1c(N2CCCO[C@@H](c3cccc(C(N)=O)c3)C2)nc(-c2ccncn2)cc1=O] | (S)-2-[2-(3-aminocarbonylphenyl)-1,4-oxazepan-4-yl]-3-methyl-6-(pyrimidin-4-yl)pyrimidin-4(3H)-one |
| A016 | 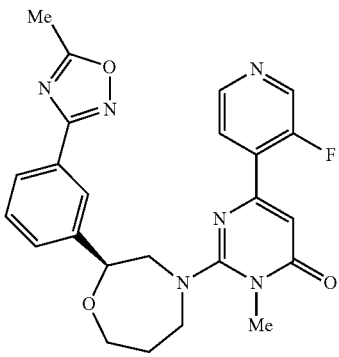 [SMILES: Cc1nc(-c2cccc([C@H]3CN(c4nc(-c5ccncc5F)cc(=O)n4C)CCCO3)c2)no1] | (S)-2-[2-[3-(5-methyl-1,2,4-oxadiazol-3-yl)-phenyl]-1,4-oxazepan-4-yl]-6-(3-fluoropyridin-4-yl)-3-methylpyrimidin-4(3H)-one |

TABLE 1-continued

| | | |
|---|---|---|
| A017 | 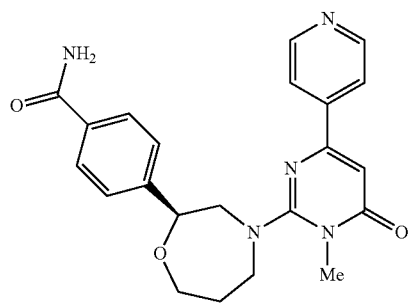 [SMILES: Cn1c(N2CCCO[C@@H](c3ccc(C(N)=O)cc3)C2)nc(-c2ccncc2)cc1=O] | (S)-2-[2-(4-aminocarbonylphenyl)-1,4-oxazepan-4-yl]-3-methyl-6-(pyridin-4-yl)pyrimidin-4(3H)-one |
| A018 | 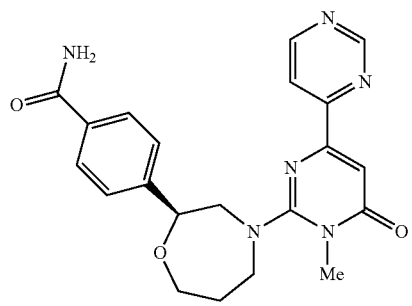 [SMILES: Cn1c(N2CCCO[C@@H](c3ccc(C(N)=O)cc3)C2)nc(-c2ccncn2)cc1=O] | (S)-2-[2-(4-aminocarbonylphenyl)-1,4-oxazepan-4-yl]-3-methyl-6-(pyrimidin-4-pyrimidin-4(3H)-one |
| A019 | 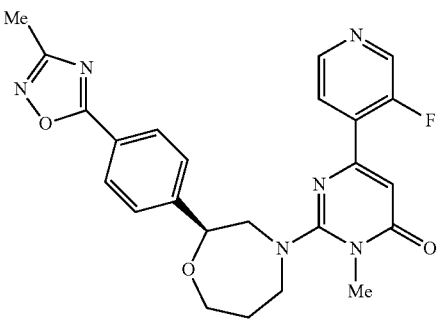 [SMILES: Cc1noc(-c2ccc([C@H]3CN(c4nc(-c5ccncc5F)cc(=O)n4C)CCCO3)cc2)n1] | (S)-2-[2-[4-(3-methyl-1,2,4-oxadiazol-5-yl)-phenyl]-1,4-oxazepan-4-yl]-6-(3-fluoropyridin-4-yl)-3-methylpyrimidin-4(3H)-one |
| A020 | 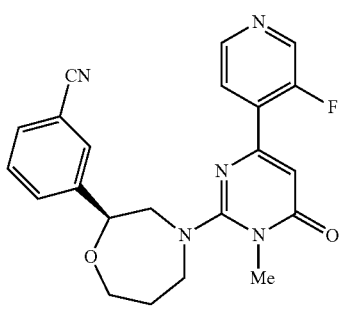 [SMILES: Cn1c(N2CCCO[C@@H](c3cccc(C#N)c3)C2)nc(-c2ccncc2F)cc1=O] | (S)-2-[2-(4-cyanophenyl)-1,4-oxazepan-4-yl]-6-(3-fluoropyridin-4-yl)-3-methylpyrimidin-4(3H)-one |
| A021 | 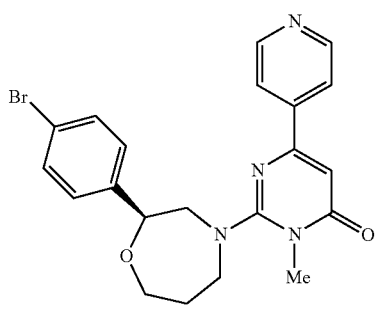 [SMILES: Cn1c(N2CCCO[C@@H](c3ccc(Br)cc3)C2)nc(-c2ccncc2)cc1=O] | (S)-2-[2-(4-bromophenyl)-1,4-oxazepan-4-yl]-3-methyl-6-(pyridin-4-yl)pyrimidin-4(3H)-one |

TABLE 1-continued
| A022 | 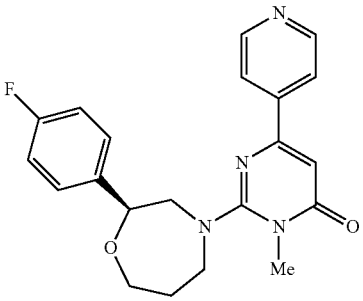 [SMILES: Cn1c(N2CCCO[C@@H](c3ccc(F)cc3)C2)nc(-c2ccncc2)cc1=O] | (S)-2-[2-(4-fluorophenyl)-1,4-oxazepan-4-yl]-3-methyl-6-(pyridin-4-yl)pyrimidin-4(3H)-one |
| A023 | 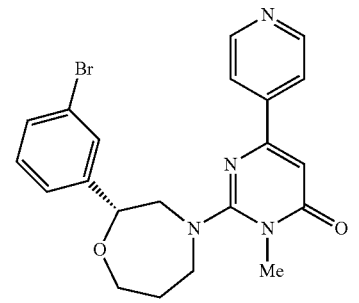 [SMILES: Cn1c(N2CCCO[C@H](c3cccc(Br)c3)C2)nc(-c2ccncc2)cc1=O] | (R)-2-[2-(3-bromophenyl)-1,4-oxazepan-4-yl]-3-methyl-6-(pyridin-4-yl)pyrimidin-4(3H)-one |
| A024 | 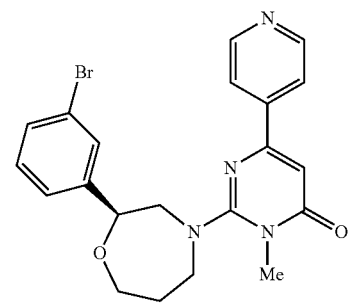 [SMILES: Cn1c(N2CCCO[C@@H](c3cccc(Br)c3)C2)nc(-c2ccncc2)cc1=O] | (S)-2-[2-(3-bromophenyl)-1,4-oxazepan-4-yl]-3-methyl-6-(pyridin-4-yl)pyrimidin-4(3H)-one |
| A025 | 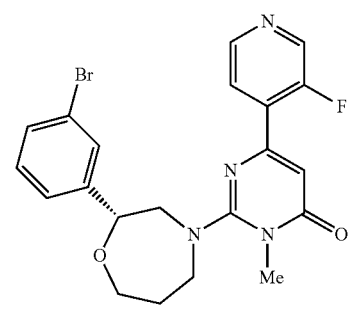 [SMILES: Cn1c(N2CCCO[C@H](c3cccc(Br)c3)C2)nc(-c2ccncc2F)cc1=O] | (R)-2-[2-(3-bromophenyl)-1,4-oxazepan-4-yl]-6-(3-fluoropyridin-4-yl)-3-methylpyrimidin-4(3H)-one |
| A026 | 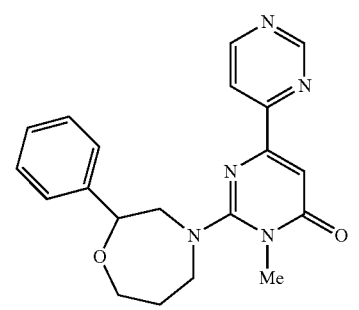 [SMILES: Cn1c(N2CCCOC(c3ccccc3)C2)nc(-c2ccncn2)cc1=O] | 2-(2-phenyl-1,4-oxazepan-4-yl)-3-methyl-6-(pyrimidin-4-yl)pyrimidin-4(3H)-one |

TABLE 1-continued

| | | |
|---|---|---|
| A027 | 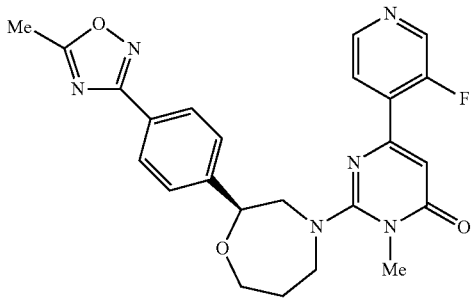 [SMILES: Cc1nc(-c2ccc([C@H]3CN(c4nc(-c5ccncc5F)cc(=O)n4C)CCCO3)cc2)no1] | (S)-2-[2-[4-(5-methyl-1,2,4-oxadiazol-3-yl)-phenyl]-1,4-oxazepan-4-yl]-6-(3-fluoropyridin-4-yl)-3-methylpyrimidin-4(3H)-one |
| A028 | 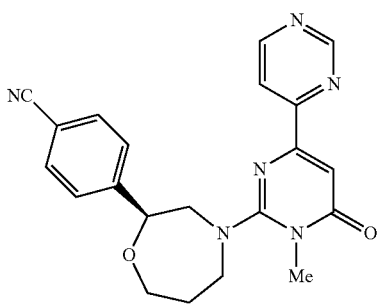 | (S)-2-[2-(4-cyanophenyl)-1,4-oxazepan-4-yl]-3-methyl-6-(pyrimidin-4-yl)pyrimidin-4(3H)-one |
| A029 | 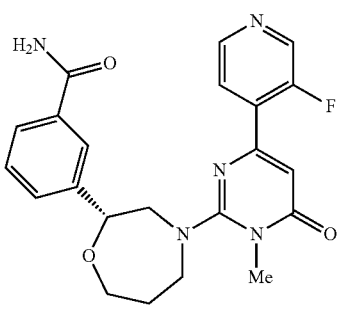 [SMILES: Cn1c(N2CCCO[C@H](c3cccc(C(N)=O)c3)C2)nc(-c2ccncc2F)cc1=O] | (R)-2-[2-(3-aminocarbonylphenyl)-1,4-oxazepan-4-yl]-6-(3-fluoropyridin-4-yl)-3-methylpyrimidin-4(3H)-one |
| A030 | 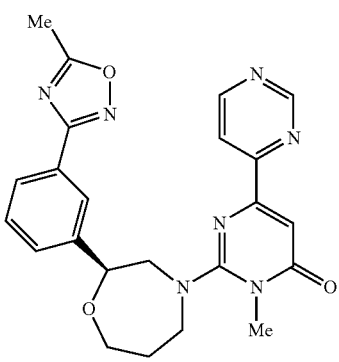 [SMILES: Cc1nc(-c2cccc([C@H]3CN(c4nc(-c5ccncn5)cc(=O)n4C)CCCO3)c2)no1] | (S)-2-[2-[3-(5-methyl-1,2,4-oxadiazol-3-yl)-phenyl]-1,4-oxazepan-4-yl]-3-methyl-6-(pyrimidin-4-yl)pyrimidin-4(3H)-one |
| A031 | 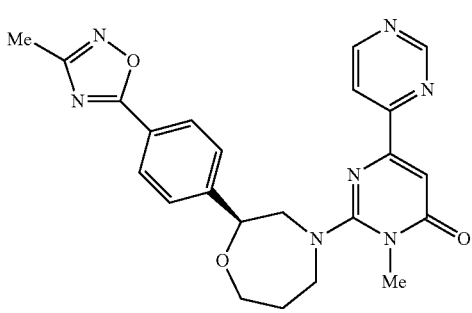 [SMILES: Cc1noc(-c2ccc([C@H]3CN(c4nc(-c5ccncn5)cc(=O)n4C)CCCO3)cc2)n1] | (S)-2-[2-[4-(3-methyl-1,2,4-oxadiazol-5-yl)-phenyl]-1,4-oxazepan-4-yl]-3-methyl-6-(pyrimidin-4-yl)pyrimidin-4(3H)-one |

TABLE 1-continued

| | | |
|---|---|---|
| A032 | | (S)-2-[2-[3-(3-methyl-1,2,4-oxadiazol-5-yl)-phenyl]-1,4-oxazepan-4-yl]-6-(3-fluoropyridin-4-yl)-3-methylpyrimidin-4(3H)-one |
| A033 | | (S)-2-[2-(3-aminocarbonylphenyl)-1,4-oxazepan-4-yl]-3-methyl-6-(pyridin-4-yl)pyrimidin-4(3H)-one |
| A034 | | (R)-2-[2-[4-(5-methyl-1,2,4-oxadiazol-3-yl)-phenyl]-1,4-oxazepan-4-yl]-3-methyl-6-(pyrimidin-4-yl)pyrimidin-4(3H)-one |
| A035 | | 2-[2-(4-fluorophenyl)-1,4-oxazepan-4-yl]-3-methyl-6-(pyridin-4-yl)pyrimidin-4(3H)-one hydrochloride |
| A036 | | (S)-2-[2-[4-(3-methyl-1,2,4-oxadiazol-5-yl)-phenyl]-1,4-oxazepan-4-yl]-3-methyl-6-(pyridin-4-yl)pyrimidin-4(3H)-one |

TABLE 1-continued
| | | |
|---|---|---|
| A037 | 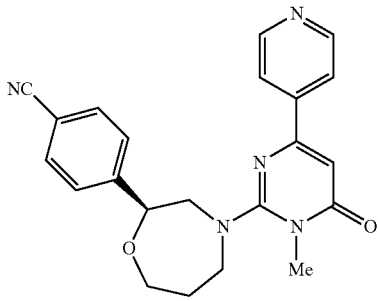 [SMILES: Cn1c(N2CCCO[C@@H](c3ccc(C#N)cc3)C2)nc(-c2ccncc2)cc1=O] | (S)-2-(2-(4-cyanophenyl)-1,4-oxazepan-4-yl)-3-methyl-6-(pyridin-4-yl)pyrimidin-4(3H)-one |
| A038 | 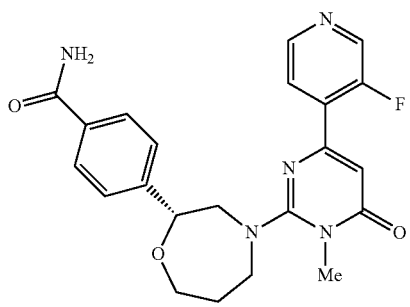 [SMILES: Cn1c(N2CCCO[C@H](c3ccc(C(N)=O)cc3)C2)nc(-c2ccncc2F)cc1=O] | (R)-2-[2-(4-aminocarbonylphenyl)-1,4-oxazepan-4-yl]-6-(3-fluoropyridin-4-yl)-3-methylpyrimidin-4(3H)-one |
| A039 | 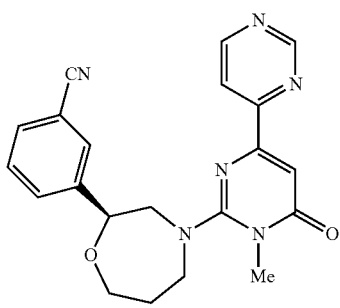 [SMILES: Cn1c(N2CCCO[C@@H](c3cccc(C#N)c3)C2)nc(-c2ccncn2)cc1=O] | (S)-2-[2-(3-cyanophenyl)-1,4-oxazepan-4-yl]-3-methyl-6-(pyrimidin-4-yl)pyrimidin-4(3H)-one |
| A040 | 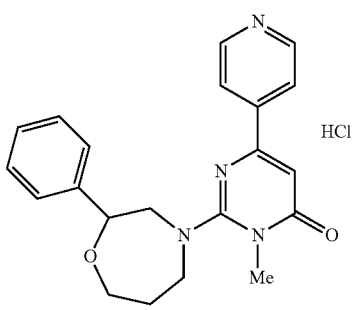 [SMILES: Cn1c(N2CCCOC(c3ccccc3)C2)nc(-c2ccncc2)cc1=O ; Cl] | 2-(2-phenyl-1,4-oxazepan-4-yl)-3-methyl-6-(pyridin-4-yl)pyrimidin-4(3H)-one |
| A041 | 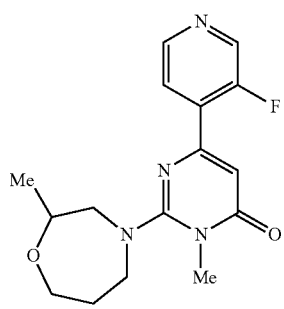 [SMILES: CC1CN(c2nc(-c3ccncc3F)cc(=O)n2C)CCCO1] | 2-(2-methyl-1,4-oxazepan-4-yl)-6-(3-fluoropyridin-4-yl)-3-methylpyrimidin-4(3H)-one |

TABLE 1-continued

| ID | Name |
|---|---|
| A042 | (S)-2-[2-[3-(5-methyl-1,2,4-oxadiazol-3-yl)-phenyl]-1,4-oxazepan-4-yl]-3-methyl-6-(pyridin-4-yl)pyrimidin-4(3H)-one |
| A043 | (R)-2-[2-(3-bromophenyl)-1,4-oxazepan-4-yl]-3-methyl-6-(pyrimidin-4-yl)pyrimidin-4(3H)-one |
| A044 | (R)-2-[2-(4-bromophenyl)-1,4-oxazepan-4-yl]-6-(3-fluoropyridin-4-yl)-3-methylpyrimidin-4(3H)-one |
| A045 | (S)-2-[2-[3-(3-methyl-1,2,4-oxadiazol-5-yl)phenyl]-1,4-oxazepan-4-yl]-3-methyl-6-(pyrimidin-4-yl)pyrimidin-4(3H)-one |
| A046 | (S)-2-[2-(3-cyanophenyl)-1,4-oxazepan-4-yl]-3-methyl-6-(pyridin-4-yl)pyrimidin-4(3H)-one |

TABLE 1-continued

| | | |
|---|---|---|
| A047 | 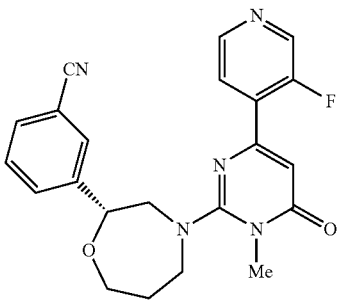 [SMILES: Cn1c(N2CCCO[C@H](c3cccc(C#N)c3)C2)nc(-c2ccncc2F)cc1=O] | (R)-2-(2-(3-cyanophenyl)-1,4-oxazepan-4-yl)-6-(3-fluoropyridin-4-yl)-3-methylpyrimidin-4(3H)-one |
| A048 | 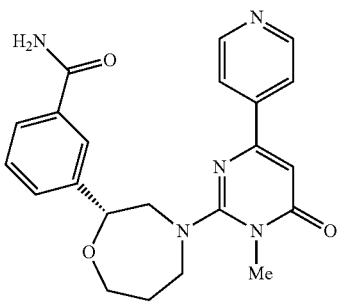 [SMILES: Cn1c(N2CCCO[C@H](c3cccc(C(N)=O)c3)C2)nc(-c2ccncc2)cc1=O] | (R)-2-[2-(3-aminocarbonylphenyl)-1,4-oxazepan-4-yl]-3-methyl-6-(pyridin-4-yl)pyrimidin-4(3H)-one |
| A049 | 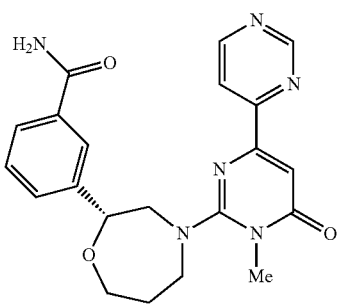 [SMILES: Cn1c(N2CCCO[C@H](c3cccc(C(N)=O)c3)C2)nc(-c2ccncn2)cc1=O] | (R)-2-[2-(3-aminocarbonylphenyl)-1,4-oxazepan-4-yl]-3-methyl-6-(pyrimidin-4-yl)pyrimidin-4(3H)-one |
| A050 | 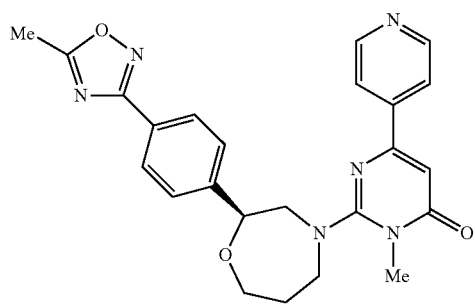 [SMILES: Cc1nc(-c2ccc([C@H]3CN(c4nc(-c5ccncc5)cc(=O)n4C)CCCO3)cc2)no1] | (S)-2-[2-[4-(5-methyl-[1,2,4]oxadiazol-3-yl)-phenyl]-1,4-oxazepan-4-yl]-3-methyl-6-(pyridin-4-yl)pyrimidin-4(3H)-one |
| A051 | 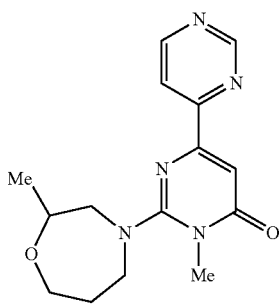 [SMILES: CC1CN(c2nc(-c3ccncn3)cc(=O)n2C)CCCO1] | 2-(2-methyl-1,4-oxazepan-4-yl)-3-methyl-6-(pyrimidin-4-yl)pyrimidin-4(3H)-one |

TABLE 1-continued

| | | |
|---|---|---|
| A052 | | (R)-2-[2-[4-(5-methyl-1,2,4-oxadiazol-3-yl)-phenyl]-1,4-oxazepan-4-yl]-6-(3-fluoropyridin-4-yl)-3-methylpyrimidin-4(3H)-one |
| A053 | | (R)-2-[2-[4-(3-methyl-1,2,4-oxadiazol-5-yl)-phenyl]-1,4-oxazepan-4-yl]-6-(3-fluoropyridin-4-yl)-3-methylpyrimidin-4(3H)-one |
| A054 | | (R)-2-[2-(4-fluorophenyl)-1,4-oxazepan-4-yl]-6-(3-fluoropyridin-4-yl)-3-methylpyrimidin-4(3H)-one |
| A055 | | (R)-2-[2-[4-(5-methyl-1,2,4-oxadiazol-3-yl)-1,4-oxazepan-4-yl]-6-(3-fluoropyridin-4-yl)-3-methylpyrimidin-4(3H)-one |
| A056 | | (S)-2-[2-[3-(3-methyl-1,2,4-oxadiazol-5-yl)-phenyl]-1,4-oxazepan-4-yl]-3-methyl-6-(pyridin-4-yl)pyrimidin-4(3H)-one |

TABLE 1-continued
| | | |
|---|---|---|
| A057 | 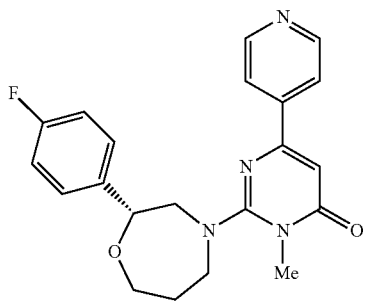 [SMILES: Cn1c(N2CCCO[C@H](c3ccc(F)cc3)C2)nc(-c2ccncc2)cc1=O] | (R)-2-(2-(4-fluorophenyl)-1,4-oxazepan-4-yl)-3-methyl-6-(pyridin-4-yl)pyrimidin-4(3H)-one |
| A058 | 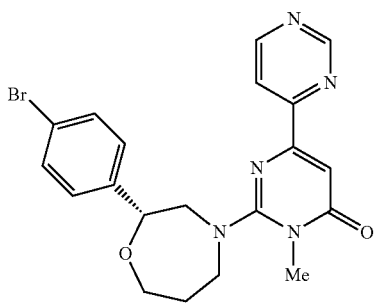 [SMILES: Cn1c(N2CCCO[C@H](c3ccc(Br)cc3)C2)nc(-c2ccncn2)cc1=O] | (R)-2-(2-(4-bromophenyl)-1,4-oxazepan-4-yl)-3-methyl-6-(pyrimidin-4-yl)pyrimidin-4(3H)-one |
| A059 | 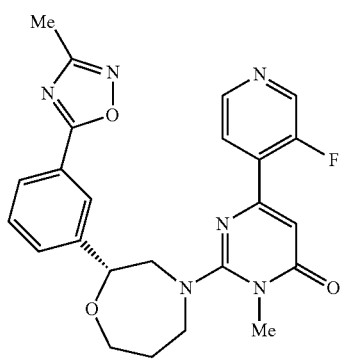 [SMILES: Cc1noc(-c2cccc([C@@H]3CN(c4nc(-c5ccncc5F)cc(=O)n4C)CCCO3)c2)n1] | (R)-2-[2-[3-(3-methyl-1,2,4-oxadiazol-5-yl)-phenyl]-1,4-oxazepan-4-yl]-6-(3-fluoropyridin-4-yl)-3-methylpyrimidin-4(3H)-one |
| A060 | 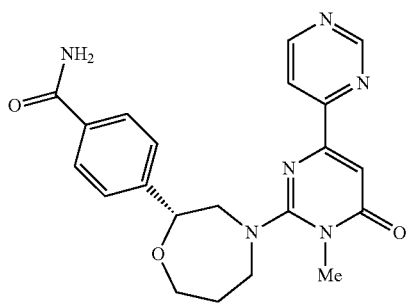 [SMILES: Cn1c(N2CCCO[C@H](c3ccc(C(N)=O)cc3)C2)nc(-c2ccncn2)cc1=O] | (R)-2-[2-(4-aminocarbonylphenyl)-1,4-oxazepan-4-yl]-3-methyl-6-(pyrimidin-4-yl)pyrimidin-4(3H)-one |
| A061 | 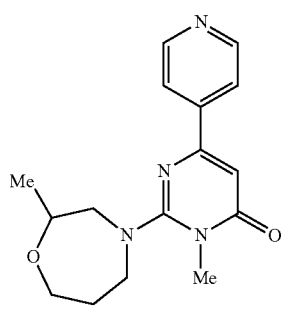 [SMILES: CC1CN(c2nc(-c3ccncc3)cc(=O)n2C)CCCO1] | 2-(2-methyl-1,4-oxazepan-4-yl)-3-methyl-6-(pyridin-4-yl)pyrimidin-4(3H)-one |

TABLE 1-continued
| | | |
|---|---|---|
| A062 | 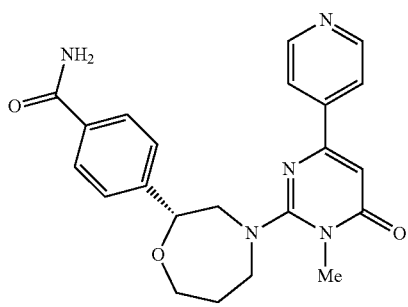 [SMILES: Cn1c(N2CCCO[C@H](c3ccc(C(N)=O)cc3)C2)nc(-c2ccncc2)cc1=O] | (R)-2-[2-(4-aminocarbonylphenyl)-1,4-oxazepan-4-yl]-3-methyl-6-(pyridin-4-yl)pyrimidin-4(3H)-one |
| A063 | 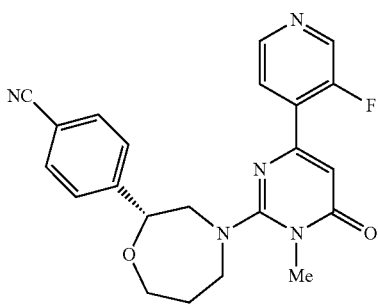 [SMILES: Cn1c(N2CCCO[C@H](c3ccc(C#N)cc3)C2)nc(-c2ccncc2F)cc1=O] | (R)-2-[2-(4-cyanophenyl)-1,4-oxazepan-4-yl]-6-(3-fluoropyridin-4-yl)-3-methylpyrimidin-4(3H)-one |
| A064 | 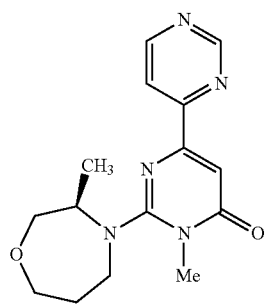 [SMILES: C[C@@H]1COCCCN1c1nc(-c2ccncn2)cc(=O)n1C] | (R)-3-methyl-2-(3-methyl-1,4-oxazepan-4-yl)-6-(pyrimidin-4-yl)pyrimidin-4(3H)-one |
| A065 | 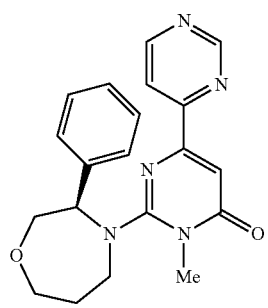 [SMILES: Cn1c(N2CCCOC[C@H]2c2ccccc2)nc(-c2ccncn2)cc1=O] | (S)-3-methyl-2-(3-phenyl-1,4-oxazepan-4-yl)-6-(pyrimidin-4-yl)pyrimidin-4(3H)-one |
| A066 | 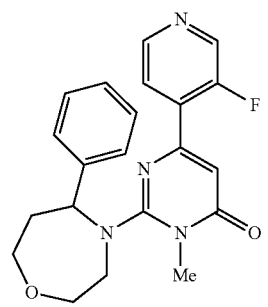 [SMILES: Cn1c(N2CCOCCC2c2ccccc2)nc(-c2ccncc2F)cc1=O] | 6-(3-fluoropyridin-4-yl)-3-methyl-2-(5-phenyl-1,4-oxazepan-4-yl)pyrimidin-4(3H)-one |

TABLE 1-continued
| | | |
|---|---|---|
| A067 | 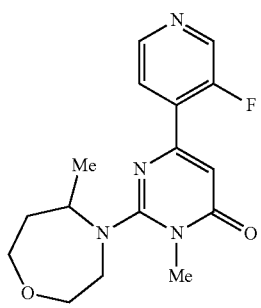 [SMILES: CC1CCOCCN1c1nc(-c2ccncc2F)cc(=O)n1C] | 6-(3-fluoropyridin-4-yl)-3-methyl-2-(5-methyl-1,4-oxazepan-4-yl)pyrimidin-4(3H)-one |
| A068 | 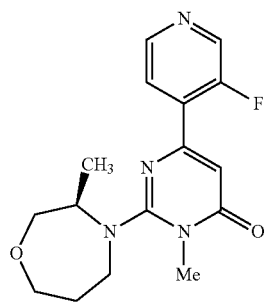 [SMILES: C[C@@H]1COCCCN1c1nc(-c2ccncc2F)cc(=O)n1C] | (R)-6-(3-fluoropyridin-4-yl)-3-methyl-2-(5-methyl-1,4-oxazepan-4-yl)pyrimidin-4(3H)-one |
| A069 | 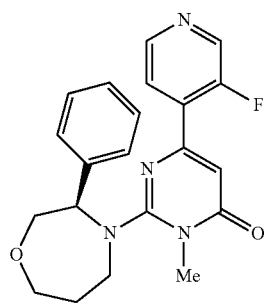 [SMILES: Cn1c(N2CCCOC[C@H]2c2ccccc2)nc(-c2ccncc2F)cc1=O] | (S)-6-(3-fluoropyridin-4-yl)-3-methyl-2-(5-phenyl-1,4-oxazepan-4-yl)pyrimidin-4(3H)-one |
| A070 | 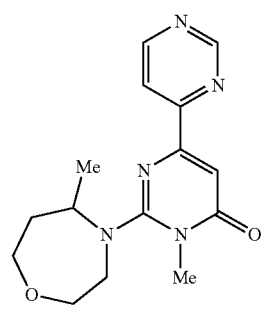 [SMILES: CC1CCOCCN1c1nc(-c2ccncn2)cc(=O)n1C] | 3-methyl-2-(5-methyl-1,4-oxazepan-4-yl)-6-(pyrimidin-4-yl)pyrimidin-4(3H)-one |
| A071 | 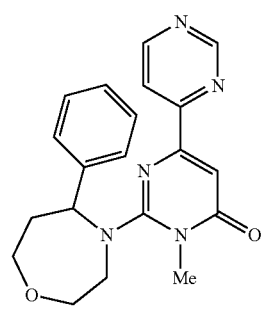 [SMILES: Cn1c(N2CCOCCC2c2ccccc2)nc(-c2ccncn2)cc1=O] | 3-methyl-2-(5-phenyl-1,4-oxazepan-4-yl)-6-(pyrimidin-4-yl)pyrimidin-4(3H)-one |

TABLE 1-continued
| A072 | 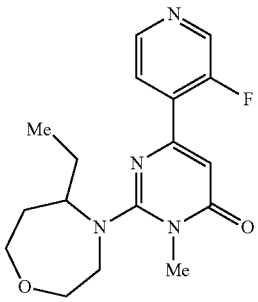 [SMILES: CCC1CCOCCN1c1nc(-c2ccncc2F)cc(=O)n1C] | 6-(3-fluoropyridin-4-yl)-3-methyl-2-(5-ethyl-1,4-oxazepan-4-yl)pyrimidin-4(3H)-one |
| A073 | 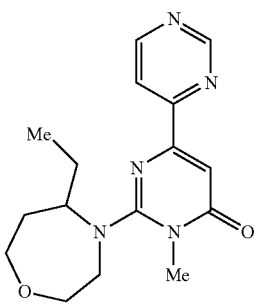 [SMILES: CCC1CCOCCN1c1nc(-c2ccncn2)cc(=O)n1C] | 3-methyl-2-(5-ethyl-1,4-oxazepan-4-yl)-6-(pyrimidin-4-yl)pyrimidin-4(3H)-one |
| A074 | 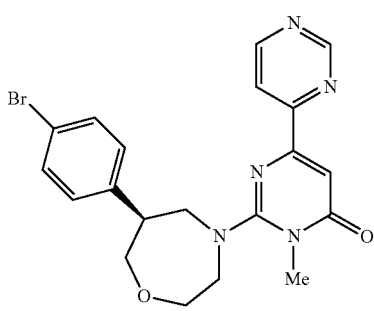 [SMILES: Cn1c(N2CCOC[C@@H](c3ccc(Br)cc3)C2)nc(-c2ccncn2)cc1=O] | (S)-2-[6-(4-bromophenyl)-1,4-oxazepan-4-yl]-3-methyl-6-(pyrimidin-4-yl)pyrimidin-4(3H)-one |
| A075 | 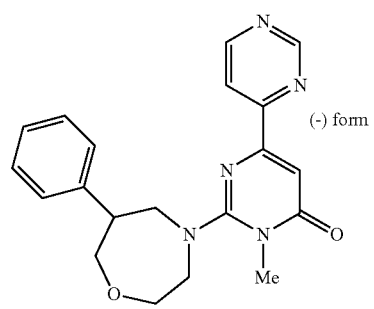 [SMILES: Cn1c(N2CCOCC(c3ccccc3)C2)nc(-c2ccncn2)cc1=O] | (−)-2-(6-phenyl-1,4-oxazepan-4-yl)-3-methyl-6-(pyrimidin-4-yl)pyrimidin-4(3H)-one |
| A076 | 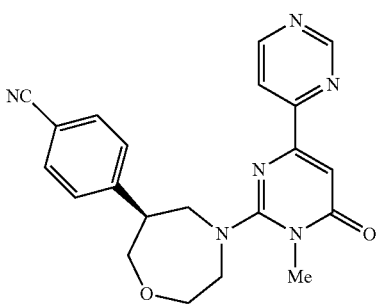 [SMILES: Cn1c(N2CCOC[C@@H](c3ccc(C#N)cc3)C2)nc(-c2ccncn2)cc1=O] | (S)-2-[6-(4-cyanoophenyl)-1,4-oxazepan-4-yl]-3-methyl-6-(pyrimidin-4-yl)pyrimidin-4(3H)-one |

TABLE 1-continued

| | | |
|---|---|---|
| A077 | | 2-[6-[4-(3-methyl-1,2,4-oxadiazol-5-yl)-phenyl]-1,4-oxazepan-4-yl]-6-(3-fluoropyridin-4-yl)-3-methylpyrimidin-4(3H)-one |
| A078 | | 2-[6-[4-(1,2,4-oxadiazol-3-yl)-phenyl]-1,4-oxazepan-4-yl]-6-(3-fluoropyridin-4-yl)-3-methylpyrimidin-4(3H)-one |
| A079 | | (S)-2-[2-(3-bromophenyl)-1,4-oxazepan-4-yl]-3-methyl-6-(pyrimidin-4-yl)pyrimidin-4(3H)-one |
| A080 | | 2-[6-[4-(1,2,4-oxadiazol-5-yl)-phenyl]-1,4-oxazepan-4-yl]-3-methyl-6-(pyrimidin-4-yl)pyrimidin-4(3H)-one |
| A081 | | 2-[6-[4-(3-methyl-1,2,4-oxadiazol-5-yl)-phenyl]-1,4-oxazepan-4-yl]-3-methyl-6-(pyrimidin-4-yl)pyrimidin-4(3H)-one |

TABLE 1-continued

| | | |
|---|---|---|
| A082 | 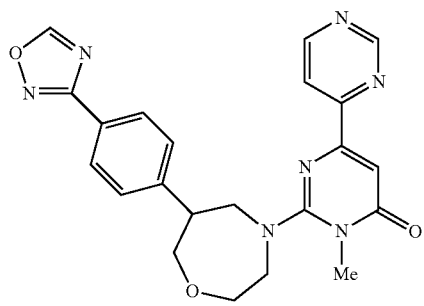 [SMILES: Cn1c(N2CCOCC(c3ccc(-c4ncon4)cc3)C2)nc(-c2ccncn2)cc1=O] | 2-[6-[4-(1,2,4-oxadiazol-3-yl)-phenyl]-1,4-oxazepan-4-yl]-3-methyl-6-(pyrimidin-4-yl)-pyrimidin-4(3H)-one |
| A083 | 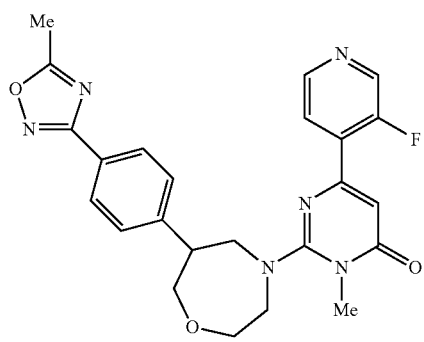 [SMILES: Cc1nc(-c2ccc(C3COCCN(c4nc(-c5ccncc5F)cc(=O)n4C)C3)cc2)no1] | 2-[6-[4-(5-methyl-1,2,4-oxadiazol-3-yl)-phenyl]-1,4-oxazepan-4-yl]-6-(3 fluoropyridin-4-yl)-3-methylpyrimidin-4(3H)-one |
| A084 | 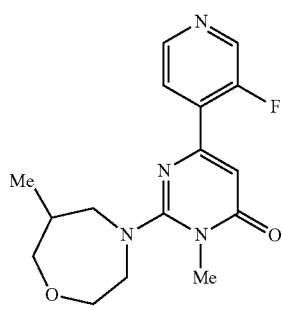 [SMILES: CC1COCCN(c2nc(-c3ccncc3F)cc(=O)n2C)C1] | 2-(6-methyl-1,4-oxazepan-4-yl)-6-(3-fluoropyridin-4-yl)-3-methylpyrimidin-4(3H)-one |
| A085 | 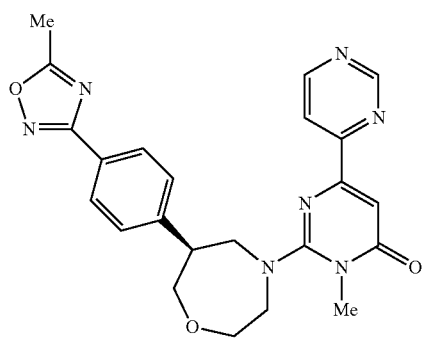 [SMILES: Cc1nc(-c2ccc([C@@H]3COCCN(c4nc(-c5ccncn5)cc(=O)n4C)C3)cc2)no1] | (S)-2-[6-[4-(5-methyl-1,2,4-oxadiazol-3-yl)-phenyl]-1,4-oxazepan-4-yl]-3-methyl-6-(pyrimidin-4-yl)pyrimidin-4(3H)-one |
| A086 | 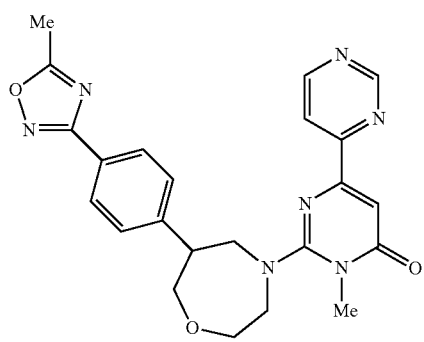 [SMILES: Cc1nc(-c2ccc(C3COCCN(c4nc(-c5ccncn5)cc(=O)n4C)C3)cc2)no1] | 2-[6-[4-(5-methyl-1,2,4-oxadiazol-3-yl)-phenyl]-1,4-oxazepan-4-yl]-3-methyl-6-(pyrimidin-4-yl)pyrimidin-4(3H)-one |

TABLE 1-continued

| | | |
|---|---|---|
| A087 | 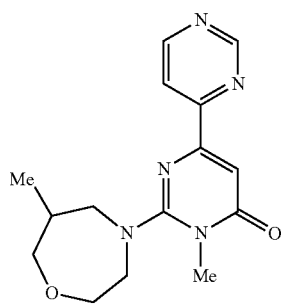 [SMILES: CC1COCCN(c2nc(-c3ccncn3)cc(=O)n2C)C1] | 2-(6-methyl-1,4-oxazepan-4-yl)-3-methyl-6-(pyrimidin-4-yl)pyrimidin-4(3H)-one |
| A088 | 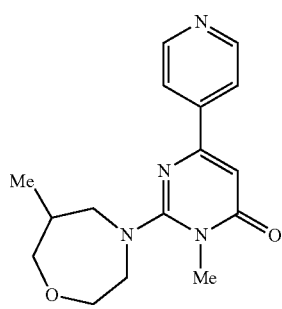 [SMILES: CC1COCCN(c2nc(-c3ccncc3)cc(=O)n2C)C1] | 2-(6-methyl-1,4-oxazepan-4-yl)-3-methyl-6-(pyridin-4-yl)pyrimidin-4(3H)-one |
| A089 | 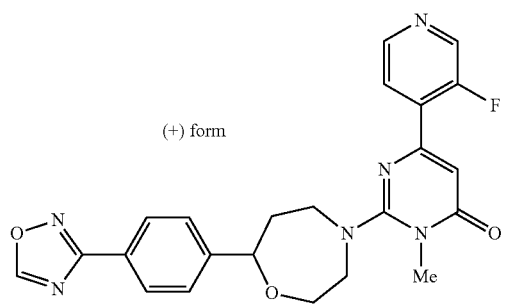 [SMILES: Cn1c(N2CCOC(c3ccc(-c4ncon4)cc3)CC2)nc(-c2ccncc2F)cc1=O] | (+)-2-[7-[4-(1,2,4-oxadiazol-3-yl-phenyl)-1,4-oxazepan-4-yl]-6-(3-fluoropyridin-4-yl)-3-methylpyrimidin-4(3H)-one |
| A090 | 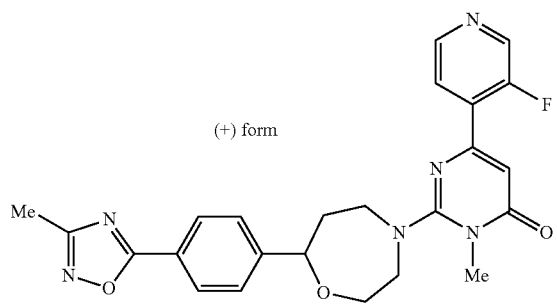 [SMILES: Cc1noc(-c2ccc(C3CCN(c4nc(-c5ccncc5F)cc(=O)n4C)CCO3)cc2)n1] | (+)-2-[7-[4-(3-methyl-1,2,4-oxadiazol-5-yl)-phenyl]-1,4-oxazepan-4-yl]-6-(3-fluoropyridin-4-yl)-3-methylpyrimidin-4(3H)-one |
| A091 | 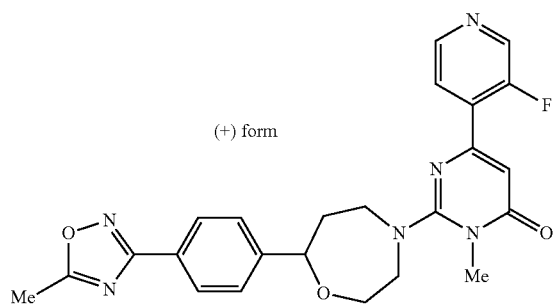 [SMILES: Cc1nc(-c2ccc(C3CCN(c4nc(-c5ccncc5F)cc(=O)n4C)CCO3)cc2)no1] | (+)-2-[7-[4-(5-methyl-1,2,4-oxadiazol-3-yl)-phenyl]-1,4-oxazepan-4-yl]-6-(3-fluoropyridin-4-yl)-3-methylpyrimidin-4(3H)-one |

TABLE 1-continued

| | | |
|---|---|---|
| A092 | 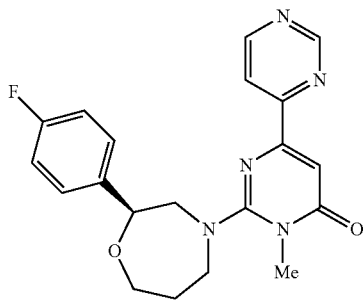 [SMILES: Cn1c(N2CCCO[C@@H](c3ccc(F)cc3)C2)nc(-c2ccncn2)cc1=O] | (S)-2-[2-(4-fluorophenyl)-1,4-oxazepan-4-yl]-3-methyl-6-(pyrimidin-4-yl)pyrimidin-4(3H)-one |
| A093 | 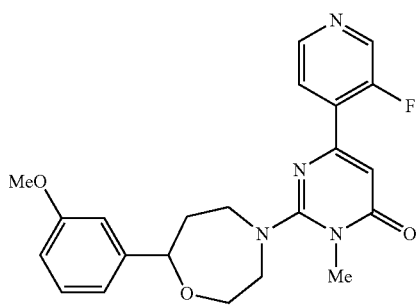 [SMILES: COc1cccc(C2CCN(c3nc(-c4ccncc4F)cc(=O)n3C)CCO2)c1] | 2-[7-(3-methoxyphenyl)-1,4-oxazepan-4-yl]-6-(3-fluoropyridin-4-yl)-3-methylpyrimidin-4(3H)-one |
| A094 | 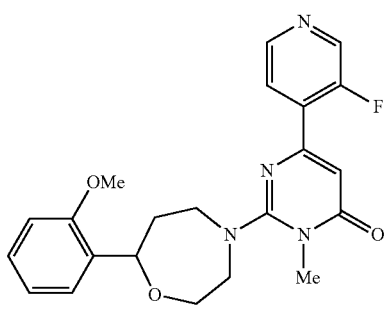 [SMILES: COc1ccccc1C1CCN(c2nc(-c3ccncc3F)cc(=O)n2C)CCO1] | 2-[7-(2-methoxyphenyl)-1,4-oxazepan-4-yl]-6-(3-fluoropyridin-4-yl)-3-methylpyrimidin-4(3H)-one |
| A095 | 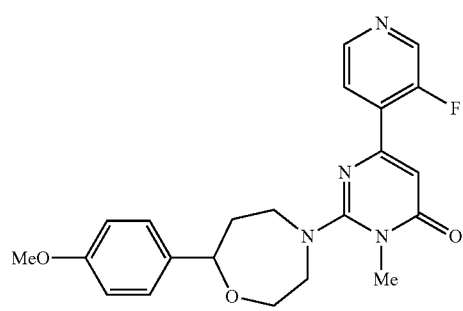 [SMILES: COc1ccc(C2CCN(c3nc(-c4ccncc4F)cc(=O)n3C)CCO2)cc1] | 2-[7-(4-methoxyphenyl)-1,4-oxazepan-4-yl]-6-(3-fluoropyridin-4-yl)-3-methylpyrimidin-4(3H)-one |
| A096 | (+) form<br>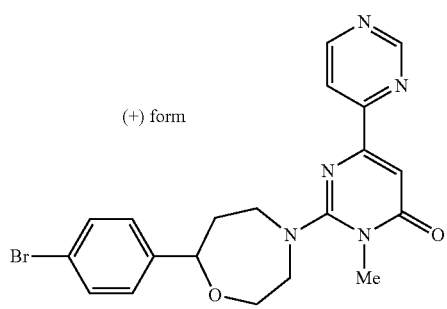 [SMILES: Cn1c(N2CCOC(c3ccc(Br)cc3)CC2)nc(-c2ccncn2)cc1=O] | (+)-2-[7-(4-bromophenyl)-1,4-oxazepan-4-yl]-3-methyl-6-(pyrimidin-4-yl)pyrimidin-4(3H)-one |

TABLE 1-continued

| | | |
|---|---|---|
| A097 | (−) form | (−)-2-[7-[4-(5-methyl-1,2,4-oxadiazol-3-yl)-phenyl]-1,4-oxazepan-4-yl]-6-(3-fluoropyridin-4-yl)-3-methylpyrimidin-4(3H)-one |
| A098 | | 2-[7-(4-fluorophenyl)-1,4-oxazepan-4-yl]-3-methyl-6-(pyrimidin-4-yl)pyrimidin-4(3H)-one |
| A099 | (+) form | (+)-2-[7-[4-(1,2,4-oxadiazol-3-yl)-phenyl]-1,4-oxazepan-4-yl]-3-methyl-6-(pyrimidin-4-yl)pyrimidin-4(3H)-one |
| A100 | (+) form | (+)-2-[7-[4-(5-methyl-1,2,4-oxadiazol-3-yl)-phenyl]-1,4-oxazepan-4-yl]-3-methyl-6-(pyrimidin-4-yl)pyrimidin-4(3H)-one |
| A101 | | 2-[7-(3-methoxyphenyl)-1,4-oxazepan-4-yl]-3-methyl-6-(pyrimidin-4-yl)pyrimidin-4(3H)-one |

TABLE 1-continued

| | | |
|---|---|---|
| A102 | 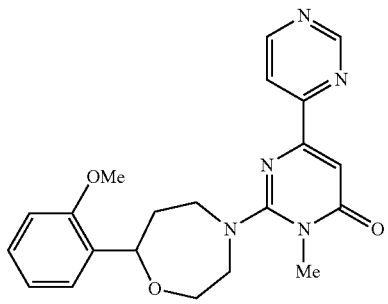 [SMILES: COc1ccccc1C1CCN(c2nc(-c3ccncn3)cc(=O)n2C)CCO1] | 2-[7-(2-methoxyphenyl)-1,4-oxazepan-4-yl]-3-methyl-6-(pyrimidin-4-yl)pyrimidin-4(3H)-one |
| A103 | 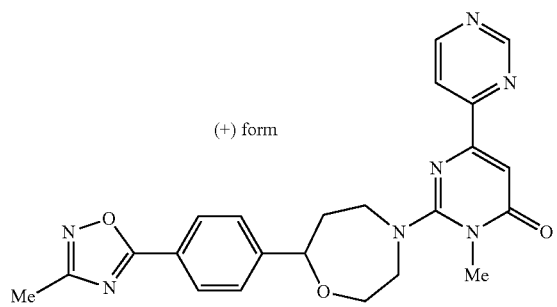 [SMILES: Cc1noc(-c2ccc(C3CCN(c4nc(-c5ccncn5)cc(=O)n4C)CCO3)cc2)n1] (+) form | (+)-2-[7-[4-(3-methyl-1,2,4-oxadiazol-5-yl)-phenyl]-1,4-oxazepan-4-yl]-3-methyl-6-(pyrimidin-4-yl)pyrimidin-4(3H)-one |
| A104 | 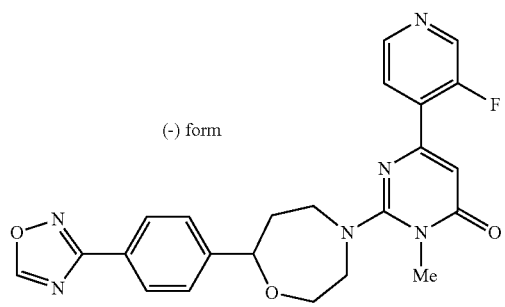 [SMILES: Cn1c(N2CCOC(c3ccc(-c4ncon4)cc3)CC2)nc(-c2ccncc2F)cc1=O] (−) form | (−)-2-[7-[4-(1,2,4-oxadiazol-3-yl)-phenyl]-1,4-oxazepan-4-yl]-6-(3-fluoropyridin-4-yl)-3-methylpyrimidin-4(3H)-one |
| A105 | 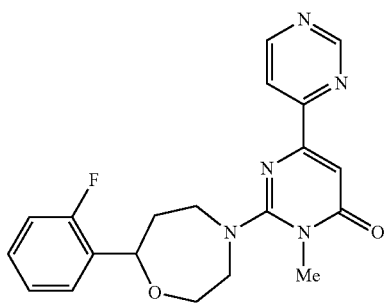 [SMILES: Cn1c(N2CCOC(c3ccccc3F)CC2)nc(-c2ccncn2)cc1=O] | 2-[7-(2-fluorophenyl)-1,4-oxazepan-4-yl]-3-methyl-6-(pyrimidin-4-yl)pyrimidin-4(3H)-one |
| A106 | 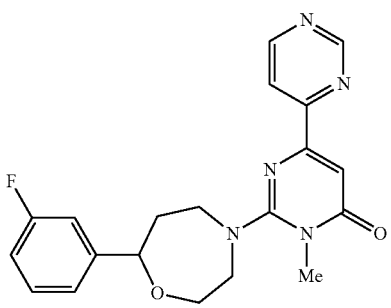 [SMILES: Cn1c(N2CCOC(c3cccc(F)c3)CC2)nc(-c2ccncn2)cc1=O] | 2-[7-(3-fluorophenyl)-1,4-oxazepan-4-yl]-3-methyl-6-(pyrimidin-4-yl)pyrimidin-4(3H)-one |

TABLE 1-continued

| | | |
|---|---|---|
| A107 | 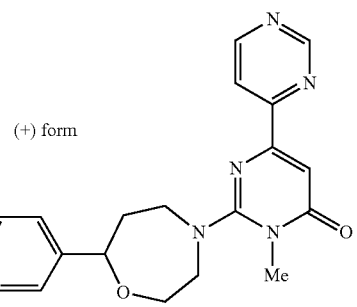 (+) form | (+)-2-[7-[4-(1,2,4-oxadiazol-5-yl)-phenyl]-1,4-oxazepan-4-yl]-3-methyl-6-(pyrimidin-4-yl)pyrimidin-4(3H)-one |
| A108 | 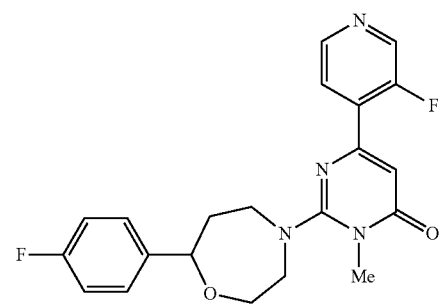 [SMILES: Cn1c(N2CCOC(c3ccc(F)cc3)CC2)nc(-c2ccncc2F)cc1=O] | 2-[7-(4-fluorophenyl)-1,4-oxazepan-4-yl]-6-(3-fluoropyridin-4-yl)-3-methylpyrimidin-4(3H)-one |
| A109 | 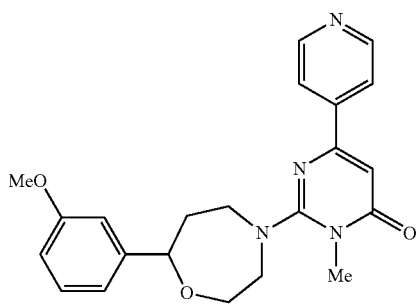 [SMILES: COc1cccc(C2CCN(c3nc(-c4ccncc4)cc(=O)n3C)CCO2)c1] | 2-[7-(3-methoxyphenyl)-1,4-oxazepan-4-yl]-3-methyl-6-(pyridin-4-yl)pyrimidin-4(3H)-one |
| A110 | 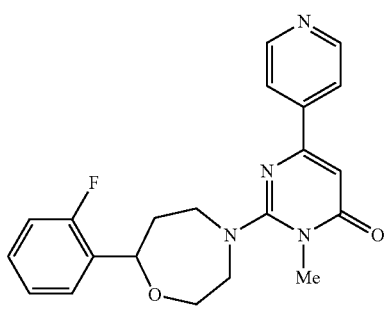 [SMILES: Cn1c(N2CCOC(c3ccccc3F)CC2)nc(-c2ccncc2)cc1=O] | 2-(7-(2-fluorophenyl)-1,4-oxazepan-4-yl)-3-methyl-6-(pyridin-4-yl)pyrimidin-4(3H)-one |
| A111 | 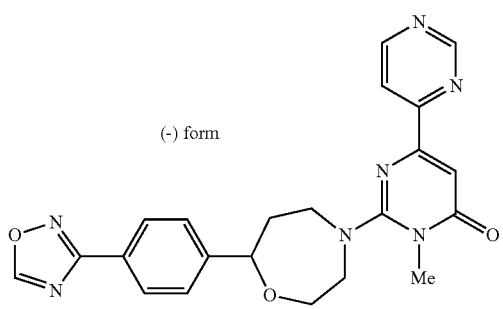 [SMILES: Cn1c(N2CCOC(c3ccc(-c4ncon4)cc3)CC2)nc(-c2ccncn2)cc1=O] (−) form | (−)-2-[7-[4-(1,2,4-oxadiazol-3-yl)-phenyl]-1,4-oxazepan-4-yl]-3-methyl-6-(pyrimidin-4-yl)pyrimidin-4(3H)-one |

TABLE 1-continued

| | | |
|---|---|---|
| A112 | 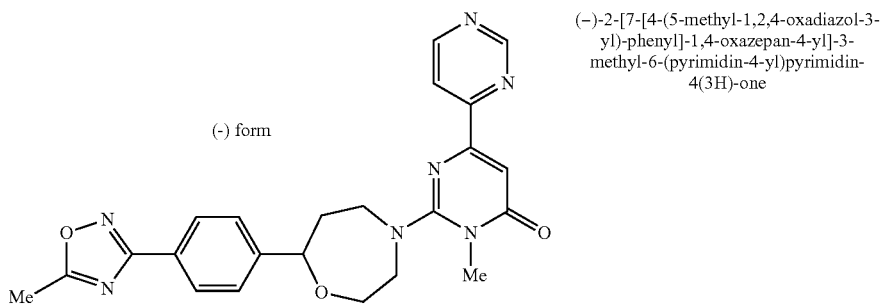 (−) form | (−)-2-[7-[4-(5-methyl-1,2,4-oxadiazol-3-yl)-phenyl]-1,4-oxazepan-4-yl]-3-methyl-6-(pyrimidin-4-yl)pyrimidin-4(3H)-one |
| A113 | 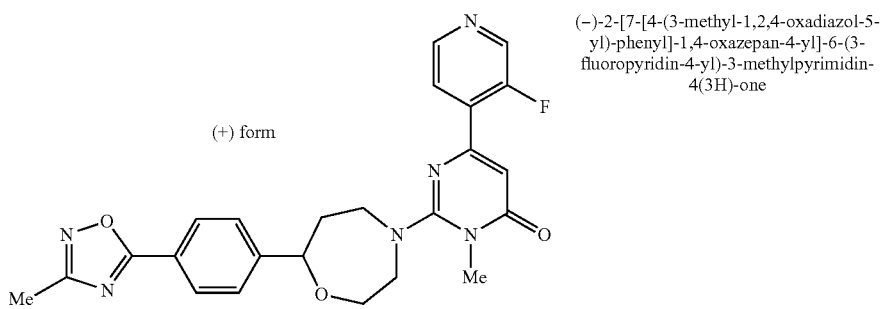 (+) form | (−)-2-[7-[4-(3-methyl-1,2,4-oxadiazol-5-yl)-phenyl]-1,4-oxazepan-4-yl]-6-(3-fluoropyridin-4-yl)-3-methylpyrimidin-4(3H)-one |
| A114 | 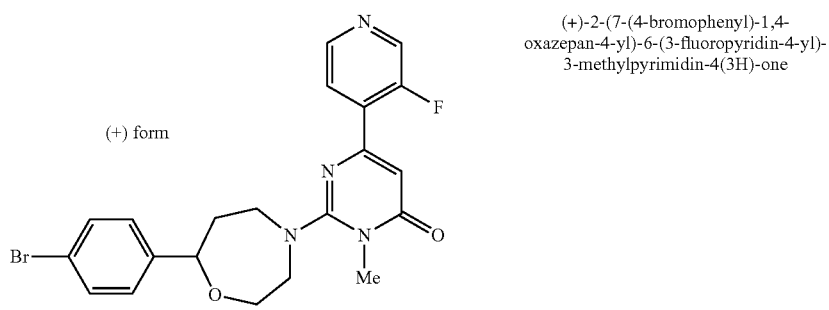 (+) form | (+)-2-(7-(4-bromophenyl)-1,4-oxazepan-4-yl)-6-(3-fluoropyridin-4-yl)-3-methylpyrimidin-4(3H)-one |
| A115 | 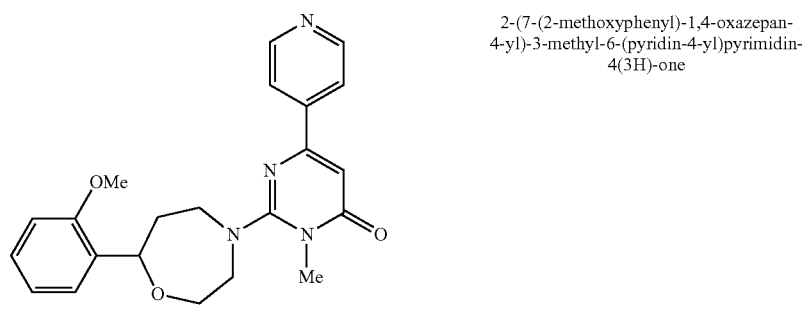 | 2-(7-(2-methoxyphenyl)-1,4-oxazepan-4-yl)-3-methyl-6-(pyridin-4-yl)pyrimidin-4(3H)-one |
| A116 | 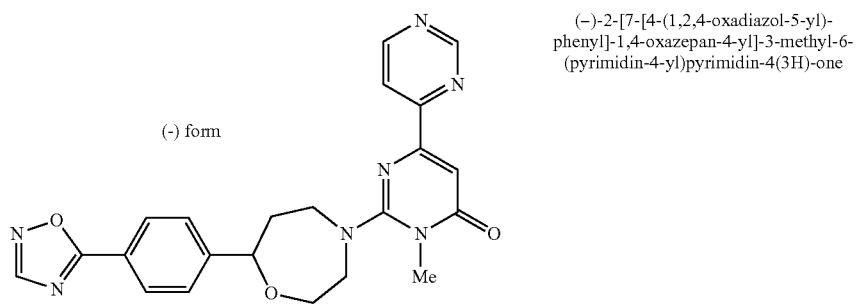 (−) form | (−)-2-[7-[4-(1,2,4-oxadiazol-5-yl)-phenyl]-1,4-oxazepan-4-yl]-3-methyl-6-(pyrimidin-4-yl)pyrimidin-4(3H)-one |

TABLE 1-continued

| | | |
|---|---|---|
| A117 | 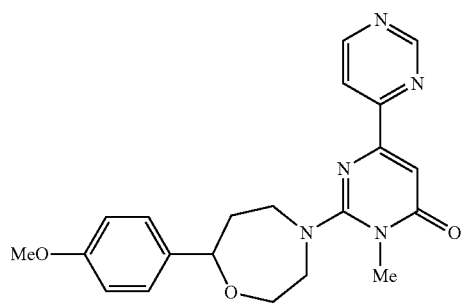 [SMILES: COc1ccc(C2CCN(c3nc(-c4ccncn4)cc(=O)n3C)CCO2)cc1] | 2-(7-(4-methoxyphenyl)-1,4-oxazepan-4-yl)-3-methyl-6-(pyrimidin-4-yl)pyrimidin-4(3H)-one |
| A118 | 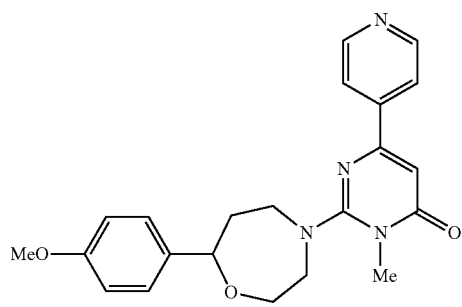 [SMILES: COc1ccc(C2CCN(c3nc(-c4ccncc4)cc(=O)n3C)CCO2)cc1] | 2-(7-(4-methoxyphenyl)-1,4-oxazepan-4-yl)-3-methyl-6-(pyridin-4-yl)pyrimidin-4(3H)-one |
| A119 | 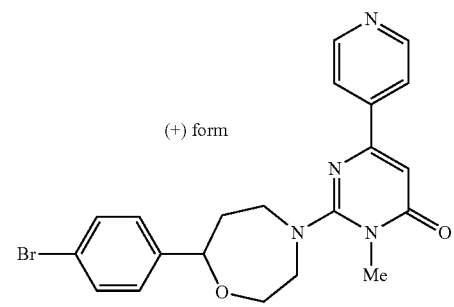 [SMILES: Cn1c(N2CCOC(c3ccc(Br)cc3)CC2)nc(-c2ccncc2)cc1=O] (+) form | (+)-2-[7-(4-bromophenyl)-1,4-oxazepan-4-yl]-3-methyl-6-(pyridin-4-yl)pyrimidin-4(3H)-one |
| A120 | 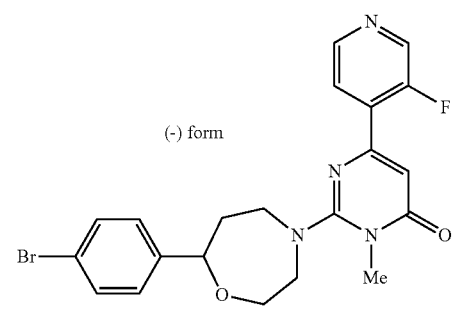 [SMILES: Cn1c(N2CCOC(c3ccc(Br)cc3)CC2)nc(-c2ccncc2F)cc1=O] (−) form | (−)-2-(7-(4-bromophenyl)-1,4-oxazepan-4-yl)-6-(3-fluoropyridin-4-yl)-3-methylpyrimidin-4(3H)-one |
| A121 | 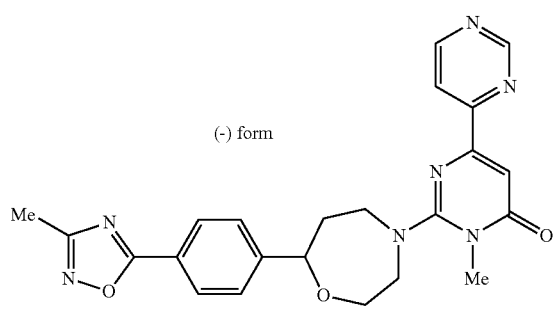 [SMILES: Cc1noc(-c2ccc(C3CCN(c4nc(-c5ccncn5)cc(=O)n4C)CCO3)cc2)n1] (−) form | (−)-2-[7-[4-(3-methyl-1,2,4-oxadiazol-5-yl)-phenyl]-1,4-oxazepan-4-yl]-3-methyl-6-(pyrimidin-4-yl)pyrimidin-4(3H)-one |

TABLE 1-continued

| | | |
|---|---|---|
| A122 | 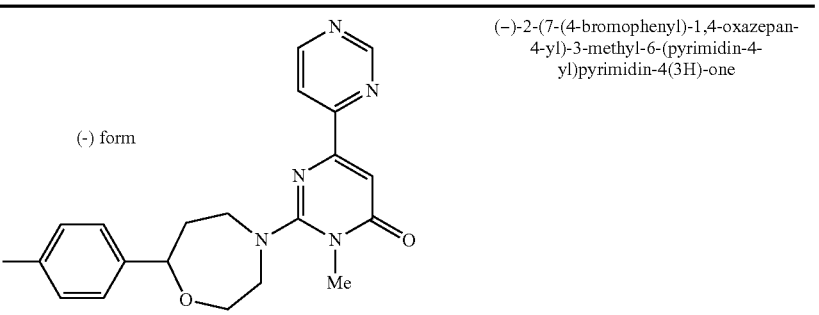 (-) form | (−)-2-(7-(4-bromophenyl)-1,4-oxazepan-4-yl)-3-methyl-6-(pyrimidin-4-yl)pyrimidin-4(3H)-one |
| A123 | 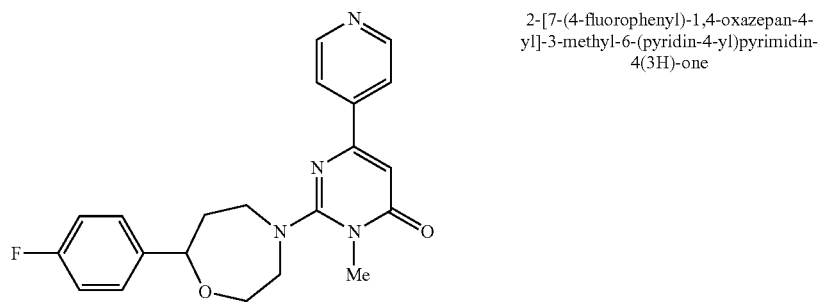 | 2-[7-(4-fluorophenyl)-1,4-oxazepan-4-yl]-3-methyl-6-(pyridin-4-yl)pyrimidin-4(3H)-one |

The compound names of the list are based on the names generated automatically by the nomenclature of CambridgSoft.

The compounds of the present invention have inhibitory activity in vitro against TPK1. Therefore, they can inhibit TPK1 activity in patients of neurodegenerative diseases such as Alzheimer disease, thereby suppressing the neurotoxicity of Aβ and the formation of PHF and inhibiting the nerve cell death. Accordingly, the compounds of the present invention are useful as an active ingredient of a medicament which radically enables preventive and/or therapeutic treatment of Alzheimer disease. In addition, the compounds of the present invention are also useful as an active ingredient of a medicament for preventive and/or therapeutic treatment of ischemic cerebrovascular accidents, Down syndrome, cerebral bleeding due to solitary cerebral amyloid angiopathy, progressive supranuclear palsy, subacute sclerosing panencephalitis, postencephalitic parkinsonism, pugilistic encephalosis, Guam parkinsonism-dementia complex, Lewy body disease, Pick's disease, corticobasal degeneration frontotemporal dementia, vascular dementia, traumatic injuries, brain and spinal cord trauma, peripheral neuropathies, retinopathies and glaucoma, non-insulin dependent diabetes, obesity, manic depressive illness, schizophrenia, alopecia, breast cancer, non-small cell lung carcinoma, thyroid cancer, T or B-cell leukemia, and several virus-induced tumors.

As the active ingredient of the medicament of the present invention, a substance may be used which is selected from the group consisting of the compound represented by the aforementioned formula (I) and pharmacologically acceptable salts thereof. The substance, per se, may be administered as the medicament of the present invention, however, it is desirable to administer the medicament in a form of a pharmaceutical composition which comprises the aforementioned substance as an active ingredient and one or more of pharmaceutical additives. As the active ingredient of the medicament of the present invention, two or more of the aforementioned substance may be used in combination.

A type of the pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like.

Dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 3000 mg (the weight of an active ingredient) to an adult.

EXAMPLES

The present invention will be explained more specifically with reference to examples. However, the scope of the present invention is not limited to the following examples. The compound number in the examples corresponds to that in the table above.

Preparation Example

Reference Example 1

Synthesis of 2-mercapto-3-methyl-6-(4-pyrimidyl)-3H-pyrimidin-4-one

A solution of ethyl 3-oxo-3-(4-pyrimidyl)propionate (34.1 g, 176 mmol), N-methyl thiourea (47.5 g, 527 mmol) and 1,8-diazabicyclo[5,4,0]-7-undecene (26.3 ml, 176 mmol) in ethanol (340 ml) was refluxed for 2 hours and the solution of methanesulfonic acid (16.9 g, 176 mmol) in water (70 ml) was added after cooling by ice-water. The precipitate was washed with water, filtered and dried to give the title compound (30.2 g, 78%).

$^1$H-NMR (DMSO-d$_6$) δ: 3.56(s, 3H), 6.88(s, 1H), 8.24(dd, J=1.2, 5.4 Hz, 2H), 9.05 (dd, J=5.4 Hz, 1H), 11.94(s, 1H).

Reference Example 2

Synthesis of 2-chloro-3-methyl-6-(4-pyrimidyl)-3H-pyrimidin-4-one

Phosphorous oxychloride (4.60 g, 30 mmol) was added to dimethylformamide (32 ml) and stirred for 20 min at 0° C. 2-Mercapto-3-methyl-6-(4-pyrimidyl)-3H-pyrimidine-4-one (4.40 g, 20 mmol) was added to the solution and stirred 5 min and then stirred at 70° C. for 2 hours. The reaction mixture was poured into ice water, neutralized by solid potassium carbonate, and extracted with ethyl acetate. The organic layer was washed with brine, dried over sodium sulfate, and evaporated under reduced pressure. Purification of the residue by silica gel chromatography (ethyl acetate) gave the title compound (1.20 g, 27%).

$^1$H-NMR (CDCl$_3$) δ: 3.74(s, 3H), 7.56(s, 1H), 8.18(d, J=5.1 Hz, 1H), 8.92(d, J=5.1 Hz, 1H), 9.30(s, 1H).

MS[M+H]$^+$:223.

Example 1

2-(5-Methyl-[1,4]-oxazepane-4-yl)-3-methyl-6-pyrimidin-4-yl-3H-pyrimidin-4-one (A070)

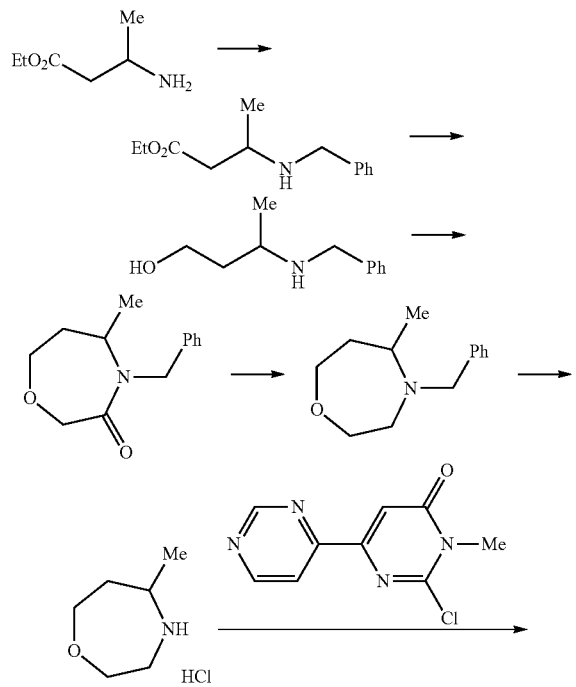

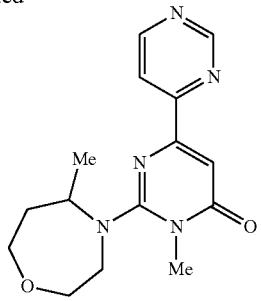

A070

To a solution of 3-amino-butyric acid ethyl ester (5.00 g, 34.3 mmol), benzaldehyde (4.1 mL, 40 mmol) and acetic acid (1.9 mL, 34 mmol) in 1,2-dichloroethane (120 mL) was added sodium triacetoxyborohydride (17 g, 80 mmol) at room temperature and the mixture was stirred for 20 hours. The reaction mixture was poured into sodium bicarbonate saturated aqueous solution and extracted with chloroform. The organic phase was dried over anhydrous sodium sulfate and concentrated. The resulting residue was purified by flash column chromatography on silica gel (chloroform/methanol=10/1 as an eluant) to afford 3-benzylamino-butyric acid ethyl ester (2.1 g, 9.5 mmol, 28%) as colorless oil.

To a suspension of lithium aluminum hydride (0.76 g, 20 mmol) in cyclopentylmethylether (20 mL) was added a solution of 3-benzylamino-butyric acid ethyl ester (2.10 g, 9.5 mmol) in cyclopentylmethylether (10 mL) dropwise at 0° C. under nitrogen atmosphere. The resulting mixture was warmed to room temperature and stirred for 3 hours. Then small amount of sodium sulfate saturated aqueous solution was added dropwise to quench the reaction at 0° C. and stirred for one hour. The resulting solid material was removed by filtration and the organic solution was concentrated to yield 3-benzylamino-butan-1-ol (1.49 g, 8.3 mmol, 87%) as colorless oil. The oil was used in the subsequent step without further purification.

To a solution of 3-benzylamino-butan-1-ol (0.50 g, 2.8 mmol) and triethylamine (0.84 mL, 6.0 mmol) in dichloromethane was added chloroacetylchloride (0.26 mL, 3.3 mmol) at 0° C. and stirred for one hour. The reaction mixture was poured into 1N hydrochloric acid aqueous solution and extracted with ethyl acetate. The organic extracts were dried over anhydrous sodium sulfate and concentrated under reduced pressure. The resulting residue was dissolved in 2-propanol (20 mL) and potassium hydroxide (0.66 g, 10 mmol) was added to the mixture at room temperature. After stirring for 18 hours, the reaction mixture was diluted with water and extracted with ethyl acetate. The organic phase was dried over anhydrous sodium sulfate and concentrated. The residual material was purified by flash column chromatography on silica gel (hexane/ethyl acetate=100/0 to 1/1 as an eluant) to afford 4-benzyl-5-methyl-[1,4]oxazepan-3-one (0.32 g, 1.4 mmol, 52%) as yellow viscous oil.

To a solution of 4-benzyl-5-methyl-[1,4]oxazepan-3-one (0.32 g, 1.4 mmol) in tetrahydrofuran (5 mL) was added 1M solution of boran-tetrahydrofran complex in tetrahydrofuran (5 mL, 5.0 mmol) dropwise at 0° C. under nitrogen atmosphere. The mixture was warmed to room temperature and stirred for 3 hours. Then the reaction was quenched by the addition of methanol and the solution was concentrated. The residual oil was dissolved in methanol (10 mL) and 1M sodium hydroxide aqueous solution was added at room temperature. The mixture was refluxed for 3 hours and diluted with water. Extraction with ethyl acetate was performed and the organic extracts were dried over anhydrous sodium sulfate. After evaporation of solvents, the residue was purified by flash column chromatography on silica gel to yield 4-benzyl-5-methyl-[1,4]oxazepane (0.30 g, 1.4 mmol, 100%) as colorless oil.

To a solution of 4-benzyl-5-methyl-[1,4]oxazepane (0.30 g, 1.4 mmol) in 1,2-dichloroethane (3 mL) was added chloroethyl chloroformate (0.56 mL, 7 mmol) at room temperature. The mixture was refluxed for 10 hours and concentrated. The resulting residue was dissolved in methanol (5 mL) and the solution was refluxed for one hour. After concentration, the residual material was triturated, washed with ethyl acetate and collected by filtration to afford 5-methyl-[1,4]oxazepane hydrochloride (0.16 g, 1.1 mmol, 76%) as a white solid.

To a suspension of 5-methyl-[1,4]oxazepane hydrochloride (0.08 g, 0.50 mmol) and 2-chloro-3-methyl-6-(pyrimidin-4-yl)-3H-pyrimidin-4-one (0.09 g, 0.40 mmol) in tetrahydrofuran (2 mL) in a sealed tube was added triethylamine (0.14 mL) at room temperature. The mixture was heated to 150° C. under microwave irradiation and stirred for 30 min. After cooling to room temperature, the reaction mixture was poured into water and extracted with chloroform. The extracts were dried over anhydrous sodium sulfate and concentrated. The residue was purified by flash column chromatography on silica gel (chloroform/methanol=10/1 as an eluant) to yield 2-(5-methyl-[1,4]oxazepane-4-yl)-3-methyl-6-pyrimidin-4-yl-3H-pyrimidin-4-one (0.03 g, 0.09 mmol, 22%) as a white solid.

Example 2

2-(5-Phenyl-[1,4]oxazepane-4-yl)-3-methyl-6-pyrimidin-4-yl-3H-pyrimidin-4-one (A071)

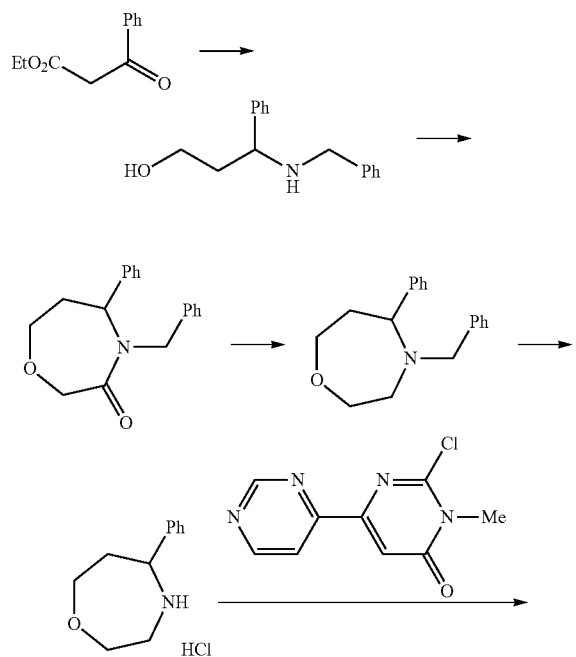

-continued

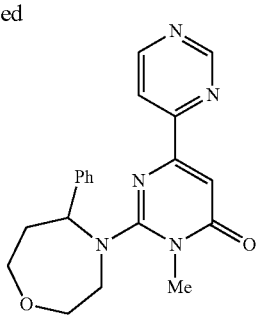

A071

The mixture of 3-oxo-3-phenyl-propionic acid ethyl ester (5.0 g, 26 mmol), benzylamine (2.9 mL, 26 mmol) and p-toluenesulfonic acid monohydrate (0.50 g, 2.6 mmol) in toluene (100 mL) was refluxed for 3 hours and concentrated. The residual materials were dissolved in cyclopentylmethylether (150 ml) and lithium aluminum hydride (3.0 g, 78 mmol) was added portionwise at 0° C. under nitrogen atmosphere. After stirring for 3 hours, small amount of sodium sulfate saturated aqueous solution was added dropwise and stirred for one hour. The resulting mixture was filtrated to remove solid materials and concentrated. Then the resulting residue was dissolved in dichloromethane (30 mL) To the mixture was added triethylamine (1.4 mL, 10 mmol) and chloroacetylchloride (0.56 g, 7.0 mmol) at 0° C. and the resulting mixture was stirred for one hour. The reaction mixture was poured into water and extracted with chloroform. The organic extracts were dried over sodium sulfate and concentrated. The residual material was dissolved in 2-propanol (30 mL) and potassium hydroxide (1.3 g, 20 mmol) was added at room temperature. After stirring for 18 hours, the reaction mixture was diluted with water and extracted with ethyl acetate. The organic phase was dried over anhydrous sodium sulfate and concentrated. The residual material was purified by flash column chromatography on silica gel (hexane/ethyl acetate=100/0 to 1/1 as an eluant) to afford 4-benzyl-5-phenyl-[1,4]oxazepan-3-one (0.77 g, 2.7 mmol, 10% from ethylbenzoyl acetate) as yellow oil.

4-Benzyl-5-phenyl-[1,4]oxazepane was prepared by the same procedure as that of 4-benzyl-5-methyl-[1,4]oxazepane except for utilizing 4-benzyl-5-phenyl-[1,4]oxazepan-3-one instead of 4-benzyl-5-methyl-[1,4]oxazepan-3-one. 4-Benzyl-5-phenyl-[1,4]oxazepane was obtained as colorless oil (0.28 g, 1.0 mmol, 39%).

5-Phenyl-[1,4]oxazepane hydrochloride was prepared by the same procedure as that of 5-methyl-[1,4]oxazepane hydrochloride except for utilizing 4-benzyl-5-phenyl-[1,4]oxazepane instead of 4-benzyl-5-methyl-[1,4]oxazepane. Then 5-phenyl-[1,4]oxazepane hydrochloride was obtained as white solid (0.14 g, 0.65 mmol, 73%).

To a suspension of 5-phenyl-[1,4]oxazepane hydrochloride (0.07 g, 0.33 mmol) and 2-chloro-3-methyl-6-(pyrimidin-4-yl)-3H-pyrimidin-4-one (0.07 g, 0.30 mmol) in tetrahydrofuran (2 mL) in a sealed tube was added triethylamine (0.14 mL) at room temperature. The mixture was heated to 150° C. under microwave irradiation and stirred for 15 min. After cooling to room temperature, the reaction mixture was poured into water and extracted with chloroform. The extracts were dried over anhydrous sodium sulfate and concentrated. The residue was purified by flash column chromatography on silica gel (chloroform/methano=10/1 as an eluant) to yield 2-(5-phenyl-[1,4]oxazepane-4-yl)-3-methyl-6-pyrimidin-4-yl-3H-pyrimidin-4-one (A071) (0.07 g, 0.20 mmol, 66%) as a white solid.

Example 3

1-Methyl-2-(6-methyl-[1,4]oxazepan-4-yl)-1H-[4,4']bipyrimidinyl-6-one (A087)

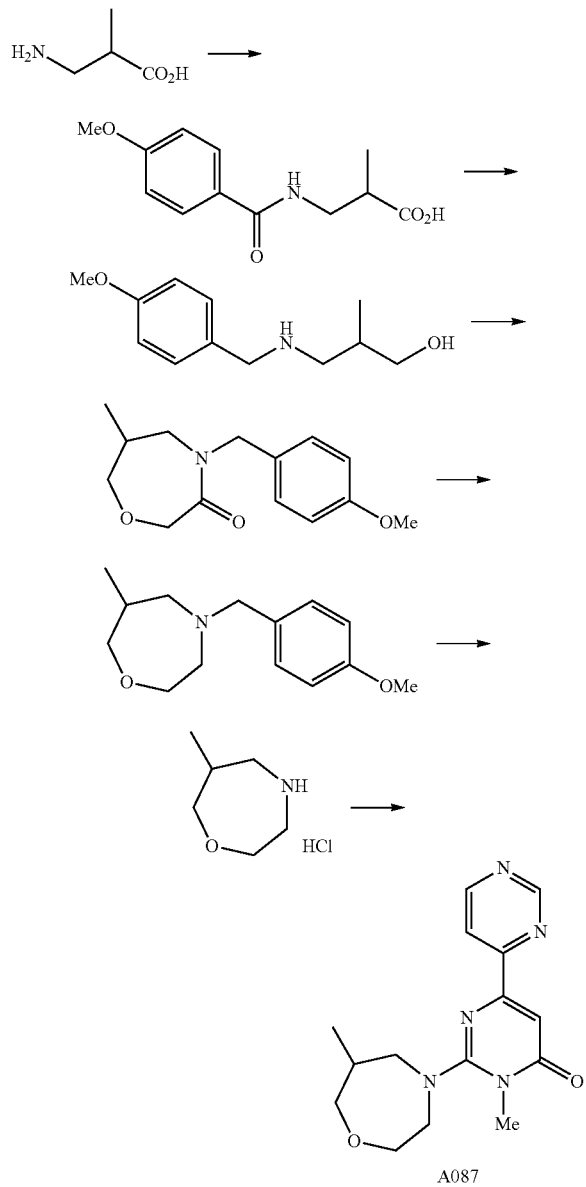

A087

To a solution of 3-amino-2-methyl-propionic acid (5.00 g, 48.4 mmol) in tetrahydrofuran (107 ml) and 1N sodium hydroxide (107 ml, 107 mmol) was added 4-methoxybenzoyl chloride (8.69 g, 50.9 mmol) at 0° C. The mixture was stirred at room temperature for 3 hours and partitioned between water and ethyl acetate. The water phase was washed with ethyl acetate and acidified with 1N hydrochloric acid. The product was extracted with ethyl acetate. The organic phase was dried over sodium sulfate, and concentrated in vacuo. To the residue dissolved into tetrahydrofuran (20 ml) was added 1M borane-tetrahydrofuran complex (6.40 ml, 6.40 mmol) at 0° C. The mixture was stirred at room temperature. After 30 minutes, the mixture was refluxed for 5 hours and acidified with 3N hydrochloric acid. The acidic aqueous solution was stirred at 60° C. for 2 hours. The organic solvent was evaporated under reduced pressure, then the residue was partitioned between water and ethyl acetate. The water phase was washed with ethyl acetate and basified with 3N sodium hydroxide. The product was extracted with chloroform. The organic phase was dried over sodium sulfate, and concentrated in vacuo to afford 3-(4-methoxy-benzylamino)-2-methyl-propan-1-ol as colorless oil (8.28 g, 82%).

To a solution of 3-(4-methoxy-benzylamino)-2-methyl-propan-1-ol (4.14 g, 19.8 mmol) in dichloromethane (60 ml) was added triethylamine (2.20 g, 21.8 mmol) and chloroacetyl chloride (2.46 g, 21.8 mmol) at 0° C. The mixture was stirred at 0° C. for one hour and partitioned between 0.5N—HCl and dichloromethane. The organic layer was washed with brine, dried over sodium sulfate and concentrated in vacuo. The residue was dissolved into 2-propanol (66.7 ml), then potassium hydroxide (2.22 g, 39.6 mmol) was added at 0° C. The mixture was stirred for 16 hours and partitioned between saturated ammonium chloride aqueous solution and ethyl acetate. The organic layer was washed with brine, dried over sodium sulfate and concentrated in vacuo. The residue was purified by silica gel column chromatography (eluant: hexane/ethyl acetate=1/1 to 1/3) to afford 4-(4-methoxy-benzyl)-6-methyl-[1,4]oxazepan-3-one as white solid (4.35 g, 88%).

To a solution of 4-(4-methoxy-benzyl)-6-methyl-[1,4]oxazepan-3-one (4.35 g, 17.5 mmol) in tetrahydrofuran (10.0 ml) was added 1M borane-tetrahydrofuran complex in tetrahydrofuran (52.3 ml, 52.3 mmol) at 0° C. The mixture was stirred at room temperature for 4 hours. After cooling to 0° C., methanol (20 ml) and 6N sodium hydroxide aqueous solution (30 ml) was added carefully. The mixture was refluxed for 2 hours and cooled to room temperature. The organic solvent was removed under reduced pressure. The residue was partitioned between saturated ammonium chloride solution and ethyl acetate. The organic layer was washed with brine, dried over sodium sulfate and concentrated in vacuo. The residue was purified by silica gel column chromatography (eluant; hexane/ethyl acetate=1/1) to afford 4-(4-methoxy-benzyl)-6-methyl-[1,4]oxazepane as colorless oil (3.24 g, 79%).

To a solution of 4-(4-methoxy-benzyl)-6-methyl-[1,4]oxazepane (3.24 g, 13.8 mmol) in 1,2-dichloroethane (23 ml) was added 1-chloroethyl chloroformate (4.93 g, 34.5 mmol) at room temperature. The mixture was refluxed for 7 hours. The reaction mixture was cooled to room temperature and then methanol (30 ml) was added. The mixture was refluxed for 5 hours and concentrated in vacuo. This crude product was washed with hexane, dried under reduced pressure to afford 6-methyl-[1,4]oxazepane hydrochloride as white solid (1.73 g, 83%).

To a slurry of 2-chloro-1-methyl-1H-[4,4']bipyrimidinyl-6-one (113 mg, 0.507 mmol) and 6-methyl-[1,4]oxazepane hydrochloride (100 mg, 0.660 mmol) in tetrahydrofuran (1.1 mL) was added triethylamine (154 mg, 1.52 mmol) at room temperature. The mixture was stirred for 15 hours and partitioned between water and ethyl acetate. The organic layer was washed with brine, dried over sodium sulfate and concentrated in vacuo. The crude product was washed with ether and dried under reduced pressure to afford 1-methyl-2-(6-methyl-[1,4]oxazepan-4-yl)-1H-[4,4']bipyrimidinyl-6-one (A087) as white solid (92.2 mg, 60%).

Example 4

2-[(6S)-6-(4-Bromophenyl)-1,4-oxazepan-4-yl]-3-methyl-6-(pyrimidin-4-yl)pyrimidin-4(3H)-one (A074)

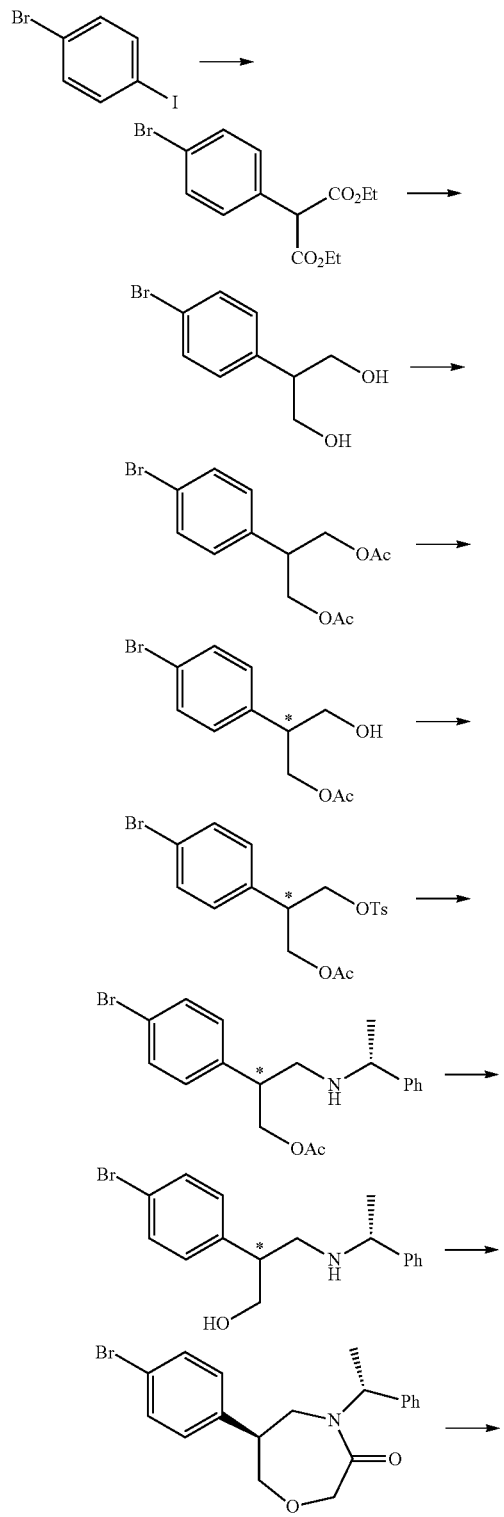

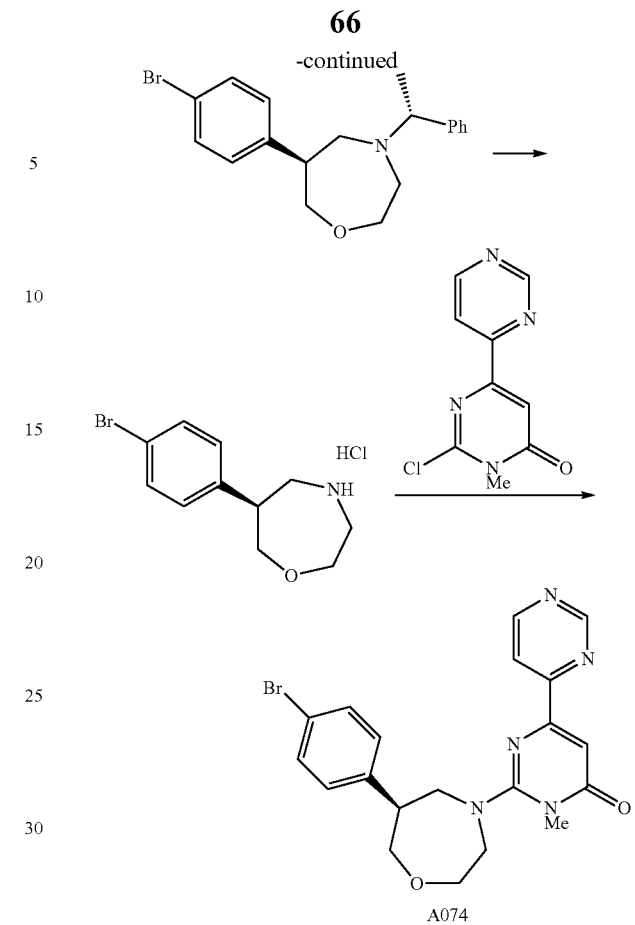

A074

To a solution of 60 wt %-sodium hydride (2.47 g, 61.7 mmol) in 1,4-dioxane (103 ml) and hexamethylphosphoramide (7.70 ml) was added diethyl malonate (9.88 g, 61.7 mmol) at room temperature under nitrogen atmosphere. The resulting mixture was stirred at room temperature for one hour and copper(I) bromide (10.6 g, 74.0 mmol) and 1-bromo-4-iodobenzene (19.2 g, 67.9 mmol) was added. The mixture was refluxed for 5 hours and cooled to room temperature. The solid materials were filtered off through a pad of Celite. After concentration, the residue was partitioned between water and ethyl acetate. The organic layer was dried over sodium sulfate, and concentrated in vacuo. The residue was purified by silica gel column chromatography (eluant: hexane/ethyl acetate=24/1) to afford diethyl 2-(4-bromophenyl)malonate as colorless oil (8.82 g, 41%).

To a solution of diethyl 2-(4-bromophenyl)malonate (18.1 g, 57.5 mmol) in ether (285 ml) was added 0.98M-diisobutylaluminium hydride in hexane (259 ml, 254 mmol) at 0° C. under nitrogen atmosphere. The resulting mixture was stirred at 0° C. for 4 hours. Aqueous potassium sodium tartrate (0.57M, 500 ml) was added to the reaction mixture for quenching the aluminum reagent and the mixture was stirred for 14 hours. The organic layer was extracted with ethyl acetate and dried over sodium sulfate. After concentration, the residue was purified by silica gel column chromatography (eluant: hexane/ethyl acetate=40/60 to ethyl acetate only) to afford 2-(4-bromophenyl)propane-1,3-diol as white solid (4.97 g, 37%).

To a solution of 2-(4-bromophenyl)propane-1,3-diol (9.01 g, 39.0 mmol) in vinyl acetate (100 ml) was added Lipase AK Amano (purchased from WAKO, 12.0 g) at room temperature. The mixture was stirred at room temperature for 11 hours and filtered through a pad of Celite to remove solid materials. After concentration, to the residue dissolved into ethanol (35 ml) and diisopropyl ether (200 ml) was added Lipase from porcine pancreas (type II, purchased from SIGMA, 22.2 g). The mixture was stirred at room temperature for 107 hours and filtered through a pad of Celite. The filtrate was concentrated in vacuo. The residue was purified by silica gel column chromatography (eluant: hexane/ethyl acetate=2/1) to afford (−)-2-(4-bromophenyl)-3-hydroxypropyl acetate as colorless oil (6.88 g, 65%). $[\alpha]_D$=−11.2 (C=0.5, CHCl$_3$).

To a solution of (−)-2-(4-bromophenyl)-3-hydroxypropyl acetate (5.88 g, 21.5 mmol) in dichloromethane (100 ml) was added triethylamine (5.45 g, 53.8 mmol), p-toluenesulfonyl chloride (4.93 g, 25.8 mmol) and 4-dimethylaminopyridine (0.263 g, 2.15 mmol) at 0° C. The mixture was stirred at room temperature for 2 hours and partitioned between saturated ammonium chloride solution and dichloromethane. The organic layer was washed with brine, dried over sodium sulfate and concentrated in vacuo. The residue was purified by silica gel column chromatography (eluant: hexane/ethyl acetate=4/1) to afford (+)-3-acetoxy-2-(4-bromophenyl)propyl 4-methyl-benzenesulfonate as colorless oil (8.32 g, 90%). $[\alpha]_D$=+1.63 (C=0.5, CHCl$_3$).

To a solution of (+)-3-acetoxy-2-(4-bromophenyl)propyl 4-methylbenzene-sulfonate (8.00 g, 18.7 mmol) in N,N-dimethylformamide (94.0 ml) was added (R)-(+)-1-phenylethylamine(11.3 g, 93.2 mmol) at room temperature. The mixture was stirred at 120° C. for 7 hours and concentrated in vacuo. The residue was partitioned between water and ethyl acetate. The organic layer was washed with brine, dried over sodium sulfate, and concentrated in vacuo. The residue was purified by silica gel column chromatography (eluant: hexane/ethyl acetate=7/3) to afford diastereopure 3-((R)-1-phenylethylamino)-2-(4-bromophenyl)propyl acetate as pale yellow oil (2.85 g, 40%).

$^1$H-NMR(400 MHz, CDCl$_3$) δ:1.27(3H, d, J=7.0 Hz), 1.32-1.40(1H, brs), 1.93(3H, s), 2.72(2H, d, J=7.0 Hz), 3.02-3.09(1H, m), 3.70(1H, q, J=7.0 Hz), 4.23(2H, d, J=7.0 Hz), 7.06(2H, d, J=8.6 Hz), 7.21-7.33(5H, m), 7.43(2H, d, J=8.6 Hz)

To a solution of diastereopure 3-((R)-1-phenylethylamino)-2-(4-bromophenyl)propyl acetate (2.85 g, 7.57 mmol) in methanol (30.3 ml) was added 1.0N-sodium hydroxide (30.3 ml, 30.3 mmol) at 0° C. The mixture was stirred at room temperature for 3 hours. The mixture was partitioned between saturated ammonium chloride solution and chloroform, and the organic layer was dried over sodium sulfate. The solvent was evaporated under reduced pressure to afford diastereopure 3-((R)-1-phenylethylamino)-2-(4-bromophenyl)propan-1-ol as white solid (2.40 g, 95%).

To a solution of diastereopure 3-((R)-1-phenylethylamino)-2-(4-bromophenyl)propan-1-ol (2.40 g, 7.18 mmol) in dichloromethane (22.0 ml) was added triethylamine (0.799 g, 7.90 mmol) and chloroacetyl chloride (0.892 g, 7.90 mmol) at 0° C. The mixture was stirred at 0° C. for one hour. The reaction mixture was partitioned between 0.5N—HCl and dichloromethane, and the organic layer was washed with brine, dried over sodium sulfate and concentrated in vacuo. To the residue dissolved into 2-propanol (48 ml) was added potassium hydroxide (805 mg, 14.4 mmol) at 0° C. The mixture was stirred at 0° C. for 3 hours and partitioned between saturated ammonium chloride solution and ethyl acetate. The organic layer was washed with brine, dried over sodium sulfate and concentrated in vacuo. The residue was purified by silica gel column chromatography (eluant: hexane/ethyl acetate=7/3) to afford (S)-6-(4-bromophenyl)-4-((R)-1-phenylethyl)-1,4-oxazepan-3-one as white solid (2.42 g, 90 W. An analytical sample for X-ray was obtained by crystallization from dichloromethane-hexane and the absolute configuration of 6-position was found to be the (S)-configuration.

To a solution of (S)-6-(4-bromophenyl)-4-((R)-1-phenylethyl)-1,4-oxazepan-3-one (1.09 g, 2.91 mmol) in tetrahydrofuran (14.0 ml) was added 1.0M-borane-tetrahydrofuran complex in tetrahydrofuran (6.40 ml, 6.40 mmol) at 0° C. The mixture was stirred at room temperature for 5 hours. After the reaction mixture was cooled to 0° C., methanol (15 ml) and 6.0N-sodium hydroxide (10 ml) was added carefully. The resulting mixture was refluxed for 2 hours and cooled to room temperature. The organic solvent was removed under reduced pressure. The residue was partitioned between saturated ammonium chloride solution and ethyl acetate. The organic layer was washed with brine, dried over sodium sulfate and concentrated in vacuo. The residue was purified by silica gel column chromatography (eluant; hexane/ethyl acetate=7/3) to afford (S)-6-(4-bromophenyl)-4-((R)-1-phenylethyl)-[1,4] oxazepane as white solid (1.00 g, 95%).

To a solution of (S)-6-(4-bromophenyl)-4-((R)-1-phenylethyl)-[1,4]oxazepane (0.610 g, 1.69 mmol) in 1,2-dichloroethane (2.83 ml) was added 1-chloroethyl chloroformate (0.605 g, 4.23 mmol) at room temperature. The mixture was refluxed for 4 hours and cooled to room temperature. After addition of methanol (5.0 ml), the mixture was refluxed for 3 hours and concentrated under reduced pressure to afford the crude product. This crude product was washed with ether, dried under reduced pressure to afford (S)-6-(4-bromophenyl)-1,4-oxazepane hydrochloride as white solid (0.424 g, 86%).

To a slurry of 2-chloro-3-methyl-6-(pyrimidin-4-yl)-3H-pyrimidin-4-one (43.5 mg, 0.195 mmol) and (S)-6-(4-bromophenyl)-1,4-oxazepane hydrochloride (60.0 mg, 0.205 mmol) was added triethylamine (59.2 mg, 0.586 mmol) at room temperature. The mixture was stirred at room temperature for 16 hours and partitioned between water and chloroform. The organic layer was washed with brine, dried over sodium sulfate and concentrated in vacuo. The residue was purified by silica gel column chromatography (eluant: chloroform/methanol=98/2) to afford (S)-2-(6-(4-bromophenyl)-[1,4-oxazepan-4-yl)-3-methyl-6-(pyrimidin-4-yl)pyrimidin-4(3H)-one (A074) as white solid (41.7 mg, 48%).

Example 5

(S)-4-(4-(1,6-Dihydro-1-methyl-6-oxo-4-(pyrimidin-4-yl)pyrimidin-2-yl)-[1,4]oxazepan-6-yl)benzonitrile (A076)

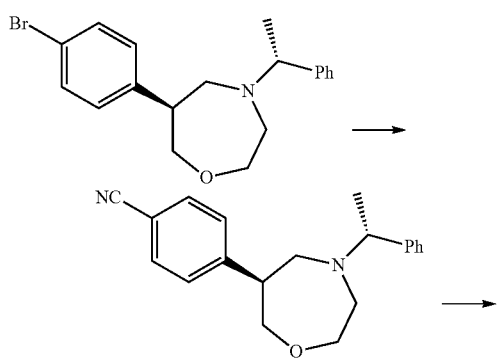

-continued

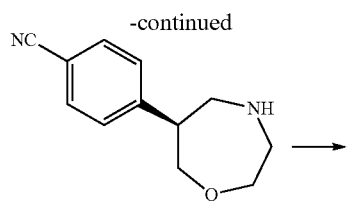

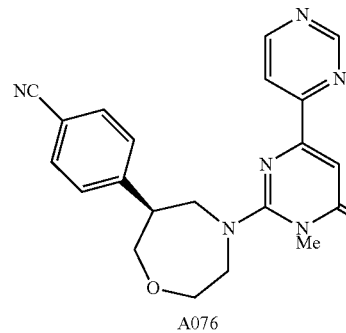

A076

To a solution of (S)-6-(4-bromophenyl)-4-((R)-1-phenylethyl)-[1,4]oxazepane (1.48 g, 4.11 mmol) in N,N-dimethylacetamide (6.9 ml) was added sodium carbonate (0.436 g, 4.11 mmol), palladium acetate (18.4 mg, 0.082 mmol), 2-dicyclohexylphosphino-2',4',6'-triisopropylbiphenyl (78.4 mg, 0.164 mmol), potassium hexacyanoferrate(II) trihydrate (0.521 g, 1.23 mmol) at room temperature under nitrogen atmosphere. The mixture was heated to 120° C. Additional palladium acetate (18.4 mg, 0.082 mmol) and 2-dicyclohexylphosphino-2',4',6'-triisopropylbiphenyl (78.4 mg, 0.164 mmol) was added twice to the reaction mixture every one hour. After one hour from last addition of the catalyst, the mixture was filtered through a pad of Celite to remove solid materials and partitioned between water and ethyl acetate. The organic layer was washed with water, dried over sodium sulfate and concentrated in vacuo. The residue was purified by silica gel column chromatography (eluant: hexane/ethyl acetate=7/3) to afford (S)-4-(4-((R)-1-phenylethyl)-[1,4]oxazepan-6-yl)benzonitrile as pale yellow solid (662 mg, 53%).

To a solution of (S)-4-(4-((R)-1-phenylethyl)-[1,4]oxazepan-6-yl)benzonitrile (0.662 g, 2.16 mmol) in 1,2-dichloroethane (3.60 ml) was added 1-chloroethyl chloroformate (0.772 g, 5.40 mmol) at room temperature. The mixture was refluxed for 8 hours. Methanol (15 ml) was added to the mixture cooled to room temperature. The mixture was refluxed again for 2 hours. The mixture was concentrated in vacuo. The residue was partitioned between aqueous sodium hydrogen carbonate and chloroform. The organic layer was dried over sodium sulfate and concentrated in vacuo. The residue was purified by silica gel column chromatography (eluent: chloroform/methanol=96/4) to afford (S)-4-([1,4]oxazepan-6-yl)benzonitrile as pale yellow solid (312 mg, 70%).

To a solution of 2-chloro-3-methyl-6-(pyrimidin-4-yl)-3H-pyrimidin-4-one (73.4 mg, 0.330 mmol) and (S)-4-([1,4]oxazepan-6-yl)benzonitrile (70.0 mg, 0.346 mmol) was added triethylamine (100 mg, 0.989 mmol) at room temperature. The mixture was stirred at room temperature for 5 hours and partitioned between water and ethyl acetate. The organic layer was washed with brine, dried over sodium sulfate and concentrated in vacuo. The residue was purified by silica gel column chromatography (eluent: hexane/ethyl acetate=1/9) to afford (S)-4-(4-(1,6-dihydro-1-methyl-6-oxo-4-(pyrimidin-4-yl)pyrimidin-2-yl)-[1,4]oxazepan-6-yl)benzonitrile (A076) as white solid (93.8 mg, 70%).

Example 6

(S)-3-Methyl-2-(6-(4-(5-methyl-1,2,4-oxadiazol-3-yl)phenyl)-[1,4]oxazepan-4-yl)-6-(pyrimidin-4-yl)pyrimidin-4(3H)-one (A085)

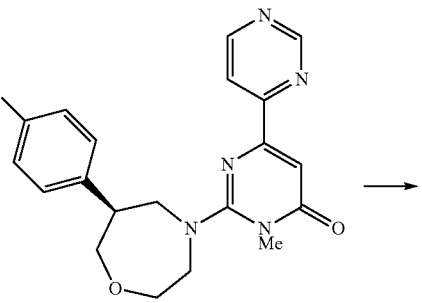

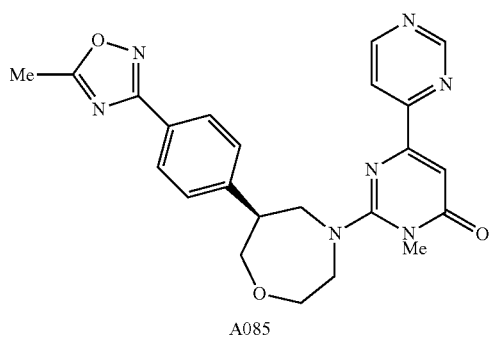

A085

To a solution of (S)-4-(4-(1,6-dihydro-1-methyl-6-oxo-4-(pyrimidin-4-yl)pyrimidin-2-yl)-[1,4]oxazepan-6-yl)benzonitrile (183 mg, 0.471 mmol) in ethanol (0.95 ml) was added 50 wt. %—hydroxylamine aqueous solution (96.4 mg, 1.46 mmol) at room temperature. The mixture was stirred at 80° C. for 2 hours and concentrated. The residue was partitioned between water and ethyl acetate. The organic layer was dried over sodium sulfate and concentrated in vacuo. N,N-dimethylformamide (0.95 ml), triethylamine (143 mg, 1.41 mmol) and acetic anhydride (62.5 mg, 0.612 mmol) was added to the residue at 0° C. The mixture was stirred at room temperature. After 2 hours, the mixture was heated to 135° C. and stirred for 2 hours. The resulting mixture cooled to room temperature was partitioned between water and chloroform. The organic layer was washed with brine, dried over sodium sulfate and concentrated in vacuo. The residue was purified by silica gel column chromatography (eluent: chloroform/methanol=97/3) to afford (S)-3-methyl-2-(6-(4-(5-methyl-1,2,4-oxadiazol-3-yl)phenyl)-[1,4]oxazepan-4-yl)-6-(pyrimidin-4-yl)pyrimidin-4(3H)-one (A085) as white solid (126 mg, 60%).

Example 7

1-Methyl-2-[6-(4-[1,2,4]oxadiazol-3-yl-phenyl)-[1,4]oxazepan-4-yl]-1H-[4,4']bipyrimidinyl-6-one (A086)

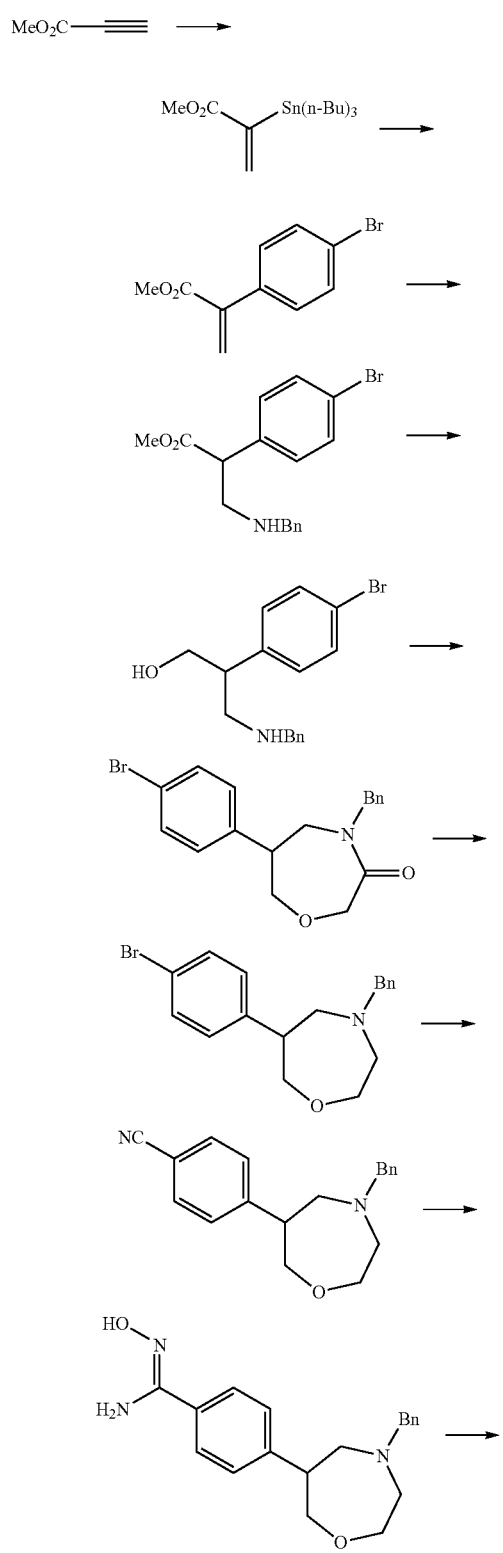

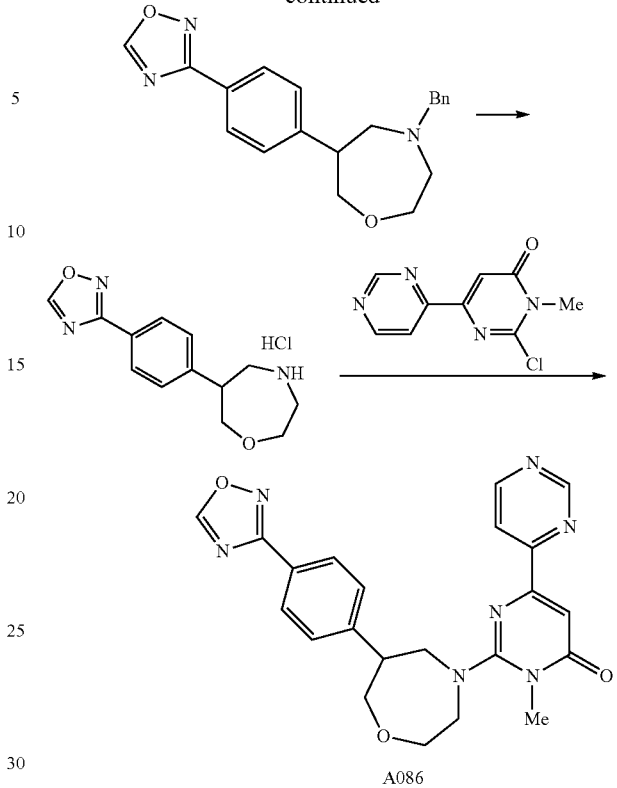

A086

To a solution of methyl propiolate (10 g, 119 mmol) and dichlorobis (triphenylphosphine)palladium(II) (1.7 g, 2.4 mmol) in tetrahydrofuran (500 mL) at room temperature under nitrogen atmosphere was added n-tributyltin hydride (20 g, 69 mmol) dropwise and stirred over night. The resulting mixture was concentrated. The residual oil was purified by flash column chromatography on silica gel (hexane/ethyl acetate=95/5 as an eluant) to afford methyl 2-tributylstannanylacrylate (15.6 g, 41.7 mmol, 60%) as colorless oil.

In a round bottom flask, a mixture of methyl 2-tributylstananylacrylate (15.6 g, 41.7 mmol), 1-bromo-4-iodobenzene (4.7 g, 16.70 mmol), copper(I) iodide (2.4 g, 12.8 mmol) and tetrakis(triphenylphosphine)palladium(0) (2 g, 1.7 mmol) in N,N'-dimethylformamide (170 mL) under nitrogen atmosphere at room temperature was prepared and stirred over night. The resulting reaction mixture was diluted with diisopropyl ether and filtered to remove solid materials. The organic solution was washed by brine and water and dried over anhydrous sodium sulfate. After concentration, the residue was passed through flash column chromatography on silica gel (hexane/ethyl acetate=90/10 as an eluant) to yield methyl 2-(4-bromophenyl)acrylate (4.0 g, 16.7 mmol, 100%) as colorless oil.

To a solution of methyl 2-(4-bromophenyl)acrylate (8.2 g, 34 mmol) in methanol (100 mL) at room temperature was added benzylamine (3.7 mL, 34 mmol). The resulting mixture was stirred for 2 days and concentrated. The residue was purified by flash column chromatography on silica gel (chloroform/methanol=90/10 as an eluant) to yield methyl 3-benzylamino-2-(4-bromophenyl)propionate (7.1 g, 20.5 mmol, 60%) as a colorless oil.

To a solution of methyl 3-benzylamino-2-(4-bromophenyl)propionate (7.1 g, 20.5 mmol) in toluene (40 mL) at 0° C. under nitrogen atmosphere was added a 1M solution of diisobutylalminium hydride (DIBAH) in toluene (65 mL, 65 mmol) and the resulting mixture was stirred for 3 hours. After cooling to 0° C., sodium fluoride (10.9 g, 260 mmol) and water (3.5 mL, 195 mmol) was added to quench aluminum reagents. The white slurry was stirred for 30 minutes and filtered to remove solid materials. The organic solution was concentrated. The resulting residue was diluted with dichloromethane (80 mL) and cooled to 0° C. To the solution was added triethylamine (4.2 mL, 30 mmol) and chloroacetyl chloride (1.6 mL, 20 mmol) and stirred for one hour. The reaction mixture was poured into 1N hydrochloric acid aqueous solution and extracted with ethyl acetate. The organic layer was dried over anhydrous sodium sulfate and concentrated. The viscous residual oil was dissolved in 2-propanol (50 mL) and then potassium hydroxide pellet (2 g, 30 mmol) was added at room temperature. After vigorous stirring over night, the reaction solution was diluted with water and extracted with ethyl acetate. The organic solution was dried over anhydrous sodium sulfate and concentrated. The residual material was purified by flash column chromatography on silica gel (hexane/ethyl acetate=3/1 as an eluant) to afford 4-benzyl-6-(4-bromo-phenyl)-[1,4]oxazepan-3-one (3.0 g, 8.3 mmol, 41%) as brown oil.

Preparation of 4-benzyl-6-(4-bromo-phenyl)-[1,4]oxazepane was performed by the same procedure as that of 4-benzyl-5-methyl-[1,4]oxazepane except for utilizing 4-benzyl-6-(4-bromo-phenyl)-[1,4]oxazepan-3-one instead of 4-benzyl-5-methyl-[1,4]oxazepan-3-one. 4-Benzyl-6-(4-bromo-phenyl)-[1,4]oxazepane was obtained as colorless oil (2.4 g, 6.9 mmol, 83%).

A mixture of 4-benzyl-6-(4-bromo-phenyl)-[1,4]oxazepane (2.4 g, 6.9 mmol), potassium hexacyanoferrate(II) trihydrate (1.48 g, 3.5 mmol), palladium(II) acetate (1.6 mg, 0.007 mmol), diphenylphosphinoferrocene (7.8 mg, 0.014 mmol) and sodium carbonate (0.74 g, 7.0 mmol) in N-methylpyrrolidone (NMP) (7 mL) was prepared in a round bottom flask at room temperature under nitrogen atmosphere and the mixture was heated to 120° C. After stirring for 10 hours, the reaction mixture was cooled to room temperature and poured into water. The organic materials were extracted with ethyl acetate and wash with brine. The organic layer was separated and dried over anhydrous sodium sulfate. After concentration, the residual oil was passed through flash column chromatography on silica gel (hexane/ethyl acetate=90/10 to 50/50 as an eluant) to obtain pure 4-(4-benzyl-[1,4]oxazepan-6-yl)-benzonitrile (1.6 g, 5.5 mmol, 79%) as light yellow oil.

Preparation of 4-benzyl-6-(4-[1,2,4]oxadiazol-3-yl-phenyl)-[1,4]oxazepane was performed by the same procedure as that of 7-[4-(5-methyl-[1,2,4]oxadiazol-3-yl) phenyl]-4-(1-phenyl-ethyl)-[1,4]oxazepane except for utilizing 4-(4-benzyl-[1,4]oxazepan-6-yl)-benzonitrile instead of 4-[4-(1-phenyl-ethyl)-[1,4]oxazepan-7-yl]-benzonitrile. 4-Benzyl-6-(4-[1,2,4]oxadiazol-3-yl-phenyl)-[1,4]oxazepane was obtained as colorless oil (0.18 g, 0.53 mmol, 53%).

Preparation of 6-(4-[1,2,4]oxadiazol-3-yl-phenyl) -[1,4]oxazepane was performed by the same procedure as that of 5-methyl-[1,4]oxazepane hydrochloride except for utilizing 4-benzyl-6-(4-[1,2,4]oxadiazol-3-yl-phenyl)-[1,4]oxazepane instead of 4-benzyl-5-methyl-[1,4]oxazepane. 6-(4-[1,2,4]Oxadiazol-3-yl-phenyl)-[1,4]oxazepane hydrochloride was obtained as white solid (0.13 g, 0.45 mmol, 86%).

1-Methyl-2-[6-(4-[1,2,4]oxadiazol-3-yl-phenyl)-[1,4]oxazepan-4-yl]-1H-[4,4']bipyrimidinyl-6-one was prepared the same procedure as that of 2-{7-[4-(3-methyl-[1,2,4]-oxadiazole-5-yl)phenyl]-[1,4]-oxazepane-4-yl}-3-methyl-6-pyrimidin-4-yl-3H-pyrimidin-4-one except for utilizing 6-(4-[1,2,4]oxadiazol-3-yl-phenyl)-[1,4]oxazepane hydrochloride instead of 7-[4-(3-Methyl-[1,2,4]oxadiazol-5-yl)-phenyl]-[1,4]oxazepane hydrochloride. 1-Methyl-2-[6-(4-[1,2,4]oxadiazol-3-yl-phenyl)-[1,4]oxazepan-4-yl]-1H-[4,4']bipyrimidinyl-6-one (A086) was obtained as white solid (0.05 g, 0.12 mmol, 59%).

Example 8

1-Methyl-2-[6-(4-[1,2,4]oxadiazol-5-yl-phenyl)-[1,4]oxazepan-4-yl]-1H-[4,4']bipyrimidinyl-6-one (A080)

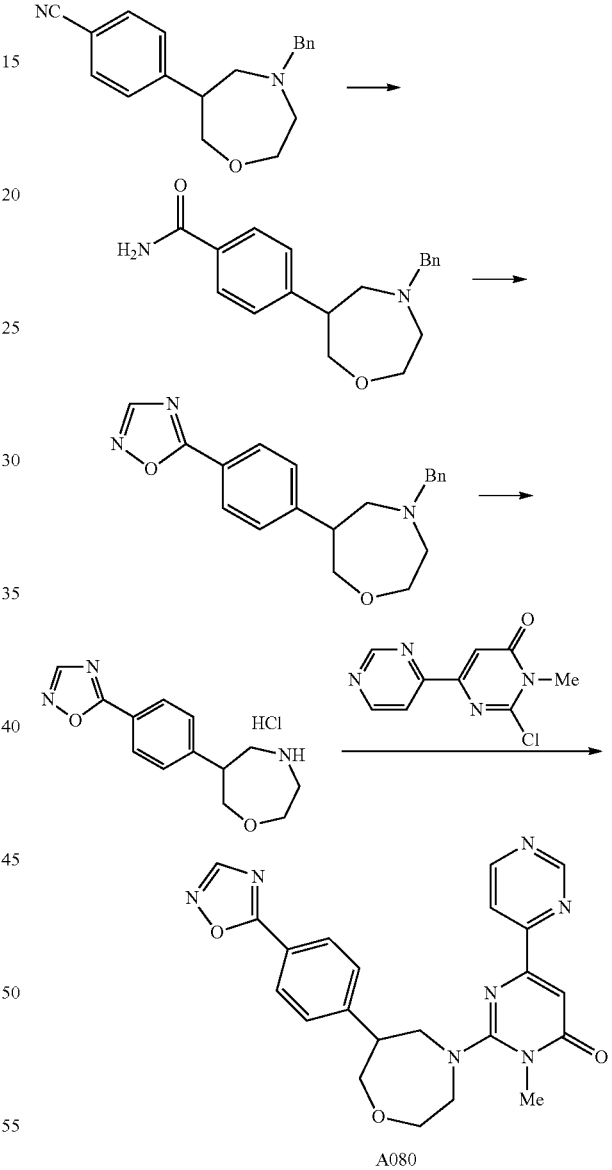

To a mixture of 4-(4-benzyl-[1,4]oxazepan-6-yl)-benzonitrile (1.0 g, 3.4 mmol) in tert-butyl alcohol (10 mL) at room temperature was added finely powdered potassium hydroxide (2.0 g, 30 mmol) and the resulting mixture was refluxed for 3 hours with vigorous stirring. After cooling to room temperature, the reaction mixture was diluted with water and extracted with chloroform. The organic layer was dried over anhydrous sodium sulfate and concentrated. The resulting residue was dissolved in dimethylformamide dimethylacetal (3 mL) at room temperature. The solution was heated to 110° C. and stirred for one hour. After removal of excess dimethylformamide dimethylacetal under reduced pressure, the residual oil was dissolved in 1,4-dioxane (3 mL). To the resulting mixture at room temperature was added hydroxylamine hydrochloride (0.09 g, 1.3 mmol), acetic acid (3 mL) and 1M aqueous solution of sodium hydroxide (1.5 mL) and the mixture was refluxed for 2 hours. After cooling to room temperature, the reaction mixture was poured into water and extracted with ethyl acetate. The organic extracts were dried over anhydrous sodium sulfate and concentrated. Purification of the residue by flash column chromatography on silica gel (hexane/ethyl acetate=80/20 to 50/50 as an eluant) was performed to yield 4-benzyl-6-(4-[1,2,4]oxadiazol-5-yl-phenyl)-[1,4]oxazepane as colorless oil (0.03 g, 0.11 mmol, 8%).

6-(4-[1,2,4]Oxadiazol-5-yl-phenyl)-[1,4]oxazepane hydrochloride was prepared by the same procedure as that of 7-[4-(5-methyl-[1,2,4]oxadiazol-3-yl)-phenyl]-[1,4]oxazepane hydrochloride except for utilizing 4-benzyl-6-(4-[1,2,4]oxadiazol-5-yl-phenyl)-[1,4]oxazepane instead of 7-[4-(5-methyl-[1,2,4]oxadiazol-3-yl)-phenyl]-4-(1-phenyl-ethyl)-[1,4]oxazepane 6-(4-[1,2,4]Oxadiazol-5-yl-phenyl)-[1,4]oxazepane hydrochloride was obtained as white solid (0.03 g, 0.09 mmol, 90%).

1-Methyl-2-[6-(4-[1,2,4]oxadiazol-5-yl-phenyl)-[1,4]oxazepan-4-yl]-1H-[4,4']bipyrimidinyl-6-one was prepared by the same procedure as that of 2-{7-[4-(3-Methyl-[1,2,4]-oxadiazole-5-yl)phenyl]-[1,4]-oxazepane-4-yl}-3-methyl-6-pyrimidin-4-yl-3H-pyrimidin-4-one except for utilizing 6-(4-[1,2,4]Oxadiazol-5-yl-phenyl)-[1,4]oxazepane hydrochloride instead of 7-[4-(3-Methyl-[1,2,4]oxadiazol-5-yl)-phenyl]-[1,4]oxazepane hydrochloride. 1-Methyl-2-[6-(4-[1,2,4]oxadiazol-5-yl-phenyl)-[1,4]oxazepan-4-yl]-1H-[4,4']bipyrimidinyl-6-one (A080) was obtained as white solid (0.02 g, 0.04 mmol, 50%).

Example 9

(+)-2-[7-(4-Bromophenyl)-[1,4]-oxazepane-4-yl]-3-methyl-6-pyrimidin-4-yl-3H-pyrimidin-4-one (A096)

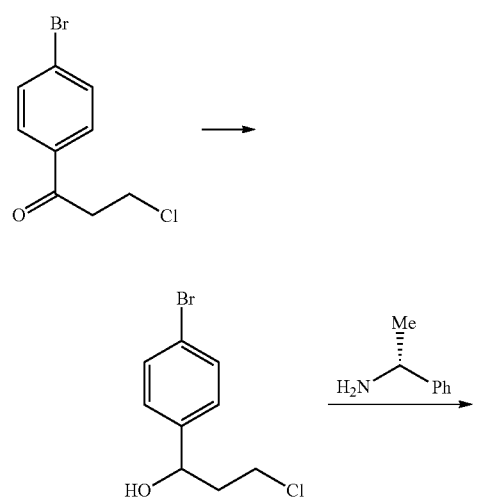

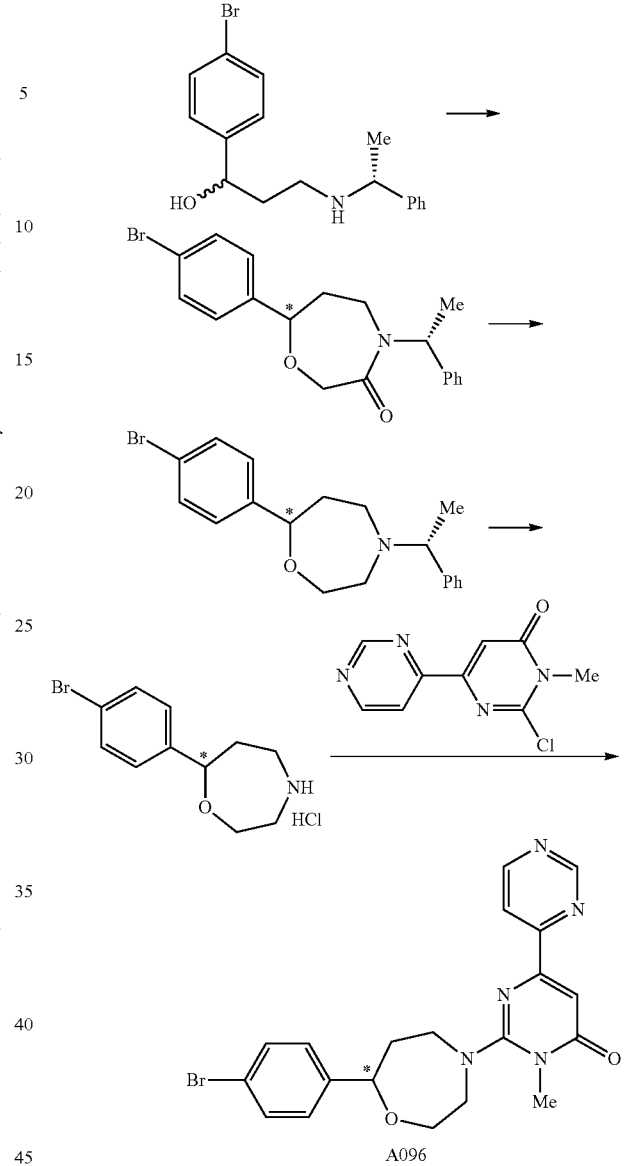

A096

To a solution of sodium borohydride (3.8 g, 100 mmol) in tetrahydrofuran (100 mL) was added a solution of 1-(4-bromo-phenyl)-3-chloro-propan-1-one (25 g, 100 mmol) dropwise at 0° C. under nitrogen atmosphere. The mixture was warmed to room temperature and stirred for 2 hours. The reaction mixture was concentrated to about 50 mL under reduced pressure and diluted with water. Extractive workup was performed with ethyl acetate and the extracts were dried over anhydrous sodium sulfate. After concentration, the residue was purified by flash column chromatography on silica gel (hexane/ethyl acetate=3/1 as an eluant) to yield 1-(4-bromo-phenyl)-3-chloro-propan-1-ol (25 g, 100 mmol, 100%) as yellow oil.

A mixture of 1-(4-bromo-phenyl)-3-chloro-propan-1-ol (25 g, 100 mmol), (R)-1-phenylethylamine (25 mL, 200 mmol), potassium iodide (33 g, 200 mmol) and potassium carbonate (27.6 g, 200 mmol) in acetonitrile (600 mL) was prepared at room temperature and warmed to 75° C. After stirring for 40 hours, solvent was evaporated. And then distillable removal of excess (R)-1-phenylethylamine was performed at 120° C. under reduced pressure. The obtained residue was dissolved in dichloromethane (200 mL) and to the resulting solution was added triethylamine (16.7 mL, 120 mmol) and chloroacetylchloride (10 mL, 120 mmol) at 0° C. After stirring for one hour, the reaction solution was poured into 1N hydrochloric acid aqueous solution and extracted with chloroform. The extracts were dried over anhydrous sodium sulfate and concentrated. The resulting residue was diluted with 2-propanol (100 mL) and to the mixture was added potassium hydroxide (9.9 g, 150 mmol) at room temperature. After stirring for 5 hours, the reaction mixture was diluted with water and extracted with ethyl acetate. The organic phase was dried over anhydrous sodium hydroxide and concentrated. Purification of the residue and separation of each diastereomer were performed by flash column chromatography on silica gel (hexane/ethyl acetate=2/1 to 1/1 as eluants) to yield 7-(4-bromo-phenyl)-4-((R)-1-phenyl-ethyl)-[1,4]oxazepan-3-one (diastereomer A; 13.1 g, 35 mmol, 35% in 3 steps) as brown oil and 7-(4-bromo-phenyl)-4-((R)-1-phenyl-ethyl)-[1,4]oxazepan-3-one (diastereomer B; 11.0 g, 29.4 mmol, 29% in 3 steps) as white solid. 7-(4-Bromo-phenyl)-4-((R)-1-phenyl-ethyl)-[1,4]oxazepan-3-one (diastereomer A):

Rf value=0.25 (eluant: hexane/ethyl acetate=2/1), 1H NMR (400 MHz, CDCl$_3$) δ ppm 1.49-1.57 (3H, m), 1.75-1.86 (1H, m), 1.96-2.04 (1H, m), 3.10-3.19 (1H, m), 3.30 (1H, ddd, J=15.1, 7.5, 2.0 Hz), 4.35 (1H, d, J=15.2 Hz), 4.51 (1H, dd, J=9.4, 3.9 Hz), 4.59 (1H, d, J=15.2 Hz), 6.05 (1H, q, J=7.3 Hz), 7.18 (2H, d, J=8.2 Hz), 7.28-7.37 (5H, m), 7.44-7.48 (2H, m). 7-(4-bromo-phenyl)-4-((R)-1-phenyl-ethyl)-[1,4] oxazepan-3-one (diastereomer B): Rf value=0.10 (eluant: hexane/ethyl acetate=2/1), 1H NMR (400 MHz, CDCl$_3$) δ ppm 1.44-1.51 (1H, m), 1.53 (3H, d, J=7.0 Hz), 1.84-1.92 (1H, m), 3.19-3.26 (1H, m), 3.29-3.37 (1H, m), 4.33 (1H, d, J=15.2 Hz), 4.50 (1H, dd, J=10.0, 3.7 Hz), 4.58 (1H, d, J=15.2 Hz), 6.00 (1H, q, J=7.0 Hz), 7.12 (2H, d, J=8.6 Hz), 7.24-7.29 (1H, m), 7.32-7.37 (4H, m), 7.41-7.45 (2H, m).

7-(4-Bromo-phenyl)-4-((R)-1-phenyl-ethyl)-[1,4]oxazepane (diastereomer type A) was prepared the same procedure as that of 4-benzyl-5-methyl-[1,4]oxazepane except for utilizing 7-(4-bromo-phenyl)-4-((R)-1-phenyl-ethyl)-[1,4] oxazepan-3-one (diastereomer type A) instead of 4-benzyl-5-methyl-[1,4]oxazepan-3-one. 7-(4-Bromo-phenyl)-4-((R)-1-phenyl-ethyl)-[1,4]oxazepane (diastereomer type A) was obtained as colorless oil (9.5 g, 26.4 mmol, 75%).

A solution of 7-(4-bromo-phenyl)-4-((R)-1-phenyl-ethyl)-[1,4]oxazepane ((diastereomer type A) (0.50 g, 1.4 mmol) and chloroethyl chloroformate (0.54 mL, 5.0 mmol) in 1,2-dichloroethane (3 mL) was prepared in a sealed tube at room temperature. The mixture was heated to 130° C. and stirred for 5 hours. After cooling to room temperature, diisopropylethylamine (0.10 mL, 0.57 mmol) was added and the resulting solution was heated to 130° C. again and stirred for additional 3 hours. And then the reaction mixture was concentrated under reduced pressure and dissolved in methanol (5 mL). The brown solution was refluxed for one hour and concentrated. The residual material was triturated, washed with ethyl acetate and collected by filtration to afford optically active 7-(4-bromo-phenyl)-[1,4]oxazepane hydrochloride (0.32 g, 1.1 mmol, 79%) as white solid. The solid was used in the subsequent step without further purification.

To a suspension of optically active 7-(4-bromo-phenyl)-[1,4]oxazepane hydrochloride (0.10 g, 0.34 mmol) and 2-chloro-3-methyl-6-(pyrimidin-4-yl)-3H-pyrimidin-4-one (0.07 g, 0.30 mmol) in tetrahydrofuran (2 mL) was added triethylamine (0.08 mL), 0.60 mmol) at room temperature. The resulting mixture was stirred over night and poured into water. Extractive workup with chloroform was performed and the organic layer was dried over anhydrous sodium sulfate and concentrated. The residue was purified by recrystallization from ethyl acetate and diisopropyl ether to yield (+)-2-[7-(4-bromophenyl)-[1,4]-oxazepane-4-yl]-3-methyl-6-pyrimidin-4-yl-3H-pyrimidin-4-one (A096) (0.10 g, 0.23 mmol, 75%) as a white solid.

Example 10

(+)-2-{7-[4-(5-Methyl-[1,2,4]-oxadiazole-3-yl)phenyl]-[1,4]-oxazepane-4-yl}-3-methyl-6-pyrimidin-4-yl-3H-pyrimidin-4-one (A100)

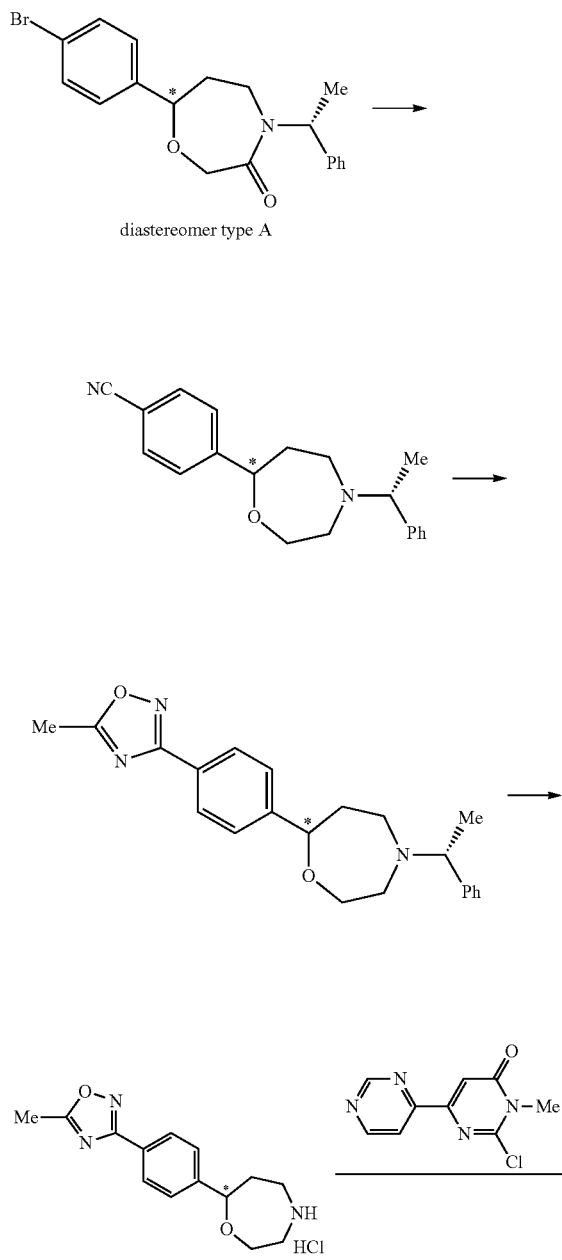

-continued

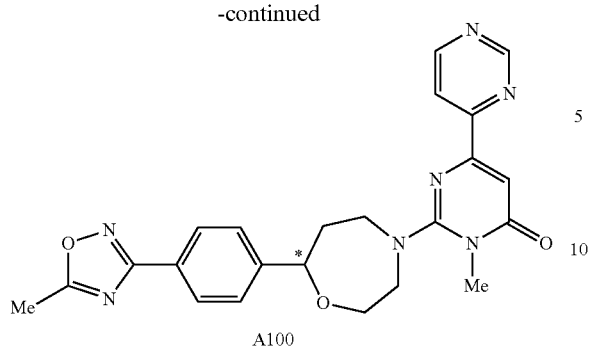

A100

A mixture of diastereopure 7-(4-bromo-phenyl)-4-((R)-1-phenyl-ethyl)-[1,4]oxazepane (diastereomer type A) (2.0 g, 5.6 mmol), zinc(II) cyanide (0.40 g, 3.4 mmol), tris(dibenzylideneacetane)dipalladium (0.46 g, 0.50 mmol), diphenylphosphinoferrocene (0.67 g, 1.2 mmol) and water (0.02 mL, 1.0 mmol) in dimethylformamide (10 mL) was prepared at room temperature under nitrogen atmosphere. The mixture was heated to 120° C. and stirred for 8 hours. After cooling to room temperature, the reaction was quenched by the addition of 2N ammonia aqueous solution and diluted with ethyl acetate. The organic layer was separated and dried over anhydrous sodium sulfate. Concentration of the solution followed by purification of the residue by flash column chromatography on silica gel (hexane/ethyl acetate=90/10 to 60/40 as eluants) was yield 4-[4-((R)-1-phenyl-ethyl)-[1,4]oxazepan-7-yl]-benzonitrile (diastereomer type A) (0.68 g, 2.2 mmol, 40%) as brown oil.

To a mixture of 4-[4-((R)-1-phenyl-ethyl)-[1,4]oxazepan-7-yl]-benzonitrile (diastereomer type A) (0.68 g, 2.2 mmol) in ethanol (5 mL) and water (3 mL) was added hydroxylamine hydrochloride (0.46 g, 6.6 mmol) and sodium bicarbonate (1.20 g, 11 mmol) at room temperature and the resulting mixture was heated to 80° C. After stirring for 2 hours, the reaction mixture was evaporated for removal of ethanol and diluted with water and chloroform. The organic phase was separated from aqueous phase and dried over anhydrous sodium sulfate. After concentration, half of the residue (0.39 g) was dissolved in xylene (3 mL) and dimethylacetamide dimethylacetal was added at room temperature. The mixture was refluxed for 3 hours and concentrated. The residual material was purified by flash column chromatography on silica gel to yield 7-[4-(5-methyl-[1,2,4]oxadiazol-3-yl)-phenyl]-4-((R)-1-phenyl-ethyl)-[1,4]oxazepane (diastereomer type A) (0.33 g, 0.92 mmol, 83%).

A solution of 7-[4-(5-methyl-[1,2,4]oxadiazol-3-yl)-phenyl]-4-((R)-1-phenyl-ethyl)-[1,4]oxazepane (diastereomer type A) (0.33 g, 0.92 mmol) and chloroethyl chloroformate (0.32 mL, 3.0 mmol) in 1,2-dichloroethane (3 mL) was prepared in a sealed tube at room temperature. The mixture was refluxed for 4 hours. After cooling to room temperature, diisopropylethylamine (0.17 mL, 1.0 mmol) was added and the resulting solution was refluxed for additional 3 hours. Then the reaction mixture was concentrated under reduced pressure and dissolved in methanol (5 mL). The brown solution was refluxed for one hour and concentrated. The residual material was triturated, washed with ethyl acetate and collected by filtration to afford 7-[4-(5-Methyl-[1,2,4]oxadiazol-3-yl)-phenyl]-[1,4]oxazepane hydrochloride (23a) (0.25 g, 0.83 mmol, 91%) as a white solid. The solid was used in the subsequent step without further purification.

To a slurry of optically active 7-[4-(5-methyl-[1,2,4]oxadiazol-3-yl)-phenyl]-[1,4]oxazepane hydrochloride (0.12 g, 0.41 mmol) and 2-chloro-3-methyl-6-(pyrimidin-4-yl)-3H-pyrimidin-4-one (0.09 g, 0.38 mmol) was added triethylamine (0.21 mL, 1.5 mmol) at room temperature. The mixture was stirred for 20 hours and poured into water. Extractive workup with chloroform was performed and the organic phase was dried over sodium sulfate. Concentration followed by purification of the residue by flash column chromatography on silica gel (chloroform/methanol=100/0 to 90/10 as eluants) yielded (+)-2-{7-[4-(5-methyl-[1,2,4]-oxadiazole-3-yl)phenyl]-[1,4]-oxazepane-4-yl}-3-methyl-6-pyrimidin-4-yl-3H-pyrimidin-4-one (A100) (0.09 g, 0.19 mmol, 50%) as yellowish solid.

Example 11

(+)-2-{7-[4-(3-Methyl-[1,2,4]-oxadiazole-5-yl)phenyl]-[1,4]-oxazepane-4-yl}-3-methyl-6-pyrimidin-4-yl-3H-pyrimidin-4-one (A103)

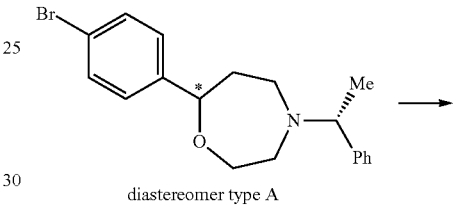

diastereomer type A

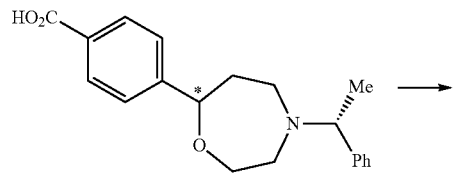

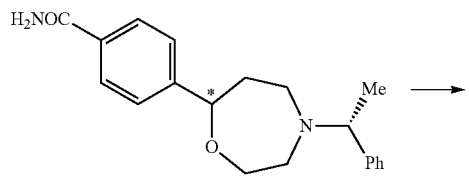

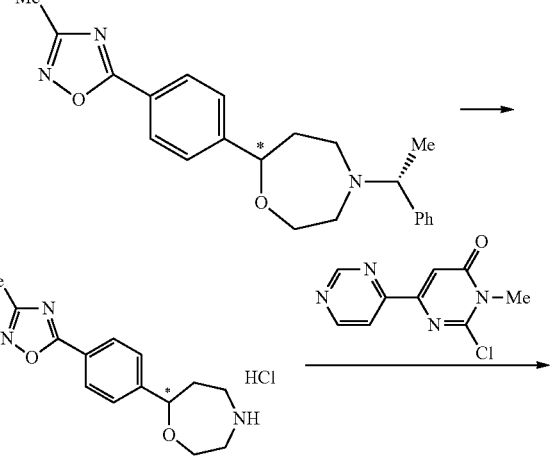

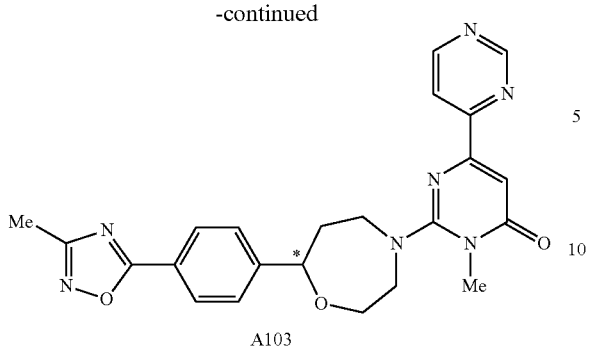

A103

To a solution of 7-(4-bromo-phenyl)-4-((R)-1-phenyl-ethyl)-[1,4]oxazepane (diastereomer type A) (2.0 g, 5.6 mmol) in tetrahydrofuran (20 mL) was added 1.60 mol/L hexane solution of n-butyllithium (4.2 mL, 6.7 mmol) at −78° C. under nitrogen atmosphere and the mixture was stirred for 15 minutes. Then carbon dioxide gas was bubbled into the reaction mixture for 30 minutes and warmed to room temperature. After the mixture was stirred for 3 hours, the reaction was quenched by the addition of water. The aqueous phase was washed with ethyl acetate and acidified by 1N hydrochloric acid aqueous solution. Extraction of organic materials from the acidic water phase was performed by tetrahydrofuran and the extracts were dried over magnesium sulfate. After concentration, 4-[4-((R)-1-phenyl-ethyl)-[1,4]oxazepan-7-yl]-benzoic acid (diastereomer type A) (0.96 g, 2.9 mmol, 53%) was isolated as colorless amorphous. The amorphous was used in the subsequent step without further purification.

To a solution of 4-[4-((R)-1-phenyl-ethyl)-[1,4]oxazepan-7-yl]-benzoic acid (diastereomer type A) (0.96 g, 2.9 mmol) and 7 mol/L methanol solution of ammonia (2 mL, 14 mmol) in N,N-dimethylformamide (10 mL) was added 4-(4,6-dimethoxy-1,3,5-triazin-2-yl)-4-methylmorpholinium chloride (1.25 g, 4.5 mmol) at room temperature and the mixture was stirred for one day. The reaction mixture was poured into water. The resulting white solid material was collected by filtration and dried under reduced pressure at 50° C. for 5 hours to yield 4-[4-((R)-1-phenyl-ethyl)-[1,4]oxazepan-7-yl]-benzamide (diastereomer type A) (0.58 g, 1.78 mmol, 61%).

4-[4-((R)-1-Phenyl-ethyl)-[1,4]oxazepan-7-yl]-benzamide (diastereomer type A) (0.28 g, 0.86 mmol) was dissolved in N,N-dimethylacetamide dimethyl acetal (1 mL) and the solution was stirred for one hour at 110° C. The mixture was concentrated and then the residue was dissolved in 1,4-dioxane (2 mL). To the solution was added 1N sodium hydroxide aqueous solution (1 mL), hydroxylamine hydrochloride (0.06 g, 0.86 mmol) and acetic acid (2 mL) and the mixture was refluxed for one hour. After cooling to room temperature, the reaction mixture was diluted with water and extracted with ethyl acetate. The organic extracts were dried over anhydrous sodium sulfate and concentrated under reduced pressure. The resulting residue was purified by flash column chromatography on silica gel (hexane/ethyl acetate=5/1 to 1/1 as eluants) to yield 7-[4-(3-methyl-[1,2,4]oxadiazol-5-yl)-phenyl]-4-((R)-1-phenyl-ethyl)-[1,4]oxazepane (diastereomer type A) (0.27 g, 0.75 mmol, 88%) as white solid.

Optically active 7-[4-(3-Methyl-[1,2,4]oxadiazol-5-yl)-phenyl]-[1,4]oxazepane hydrochloride was prepared by the same procedure as that of optically active 7-[4-(5-Methyl-[1,2,4]oxadiazol-3-yl)-phenyl]-[1,4]oxazepane hydrochloride except for utilizing 7-[4-(3-methyl-[1,2,4]oxadiazol-5-yl)-phenyl]-4-((R)-1-phenyl-ethyl)-[1,4]oxazepane instead of 7-[4-(5-methyl-[1,2,4]oxadiazol-3-yl)-phenyl]-4-(1-phenyl-ethyl)-[1,4]oxazepane. Optically active 7-[4-(3-Methyl-[1,2,4]oxadiazol-5-yl)-phenyl]-[1,4]oxazepane hydrochloride was obtained as white solid (0.16 g, 0.54 mmol, 72%).

(+)-2-{7-[4-(3-Methyl-[1,2,4]-oxadiazole-5-yl)phenyl]-[1,4]-oxazepane-4-yl}-3-methyl-6-pyrimidin-4-yl-3H-pyrimidin-4-one (A121) was prepared by the same procedure as that of 2-{7-[4-(5-methyl-[1,2,4]-oxadiazole-3-yl)phenyl]-[1,4]-oxazepane-4-yl}-3-methyl-6-pyrimidin-4-yl-3H-pyrimidin-4-one (A100) except for utilizing optically active 7-[4-(3-Methyl-[1,2,4]oxadiazol-5-yl)-phenyl]-[1,4]oxazepane hydrochloride instead of optically active 7-[4-(5-methyl-[1,2,4]oxadiazol-3-yl)-phenyl]-[1,4]oxazepane hydrochloride. (+)-2-{7-[4-(3-Methyl-[1,2,4]-oxadiazole-5-yl)phenyl]-[1,4]-oxazepane-4-yl}-3-methyl-6-pyrimidin-4-yl-3H-pyrimidin-4-one (A103) was obtained as white solid (0.07 g, 0.16 mmol, 63%).

Example 12

1-Methyl-2-(2-methyl-[1,4]oxazepan-4-yl)-1H-[4,4']bipyrimidinyl-6-one (A051)

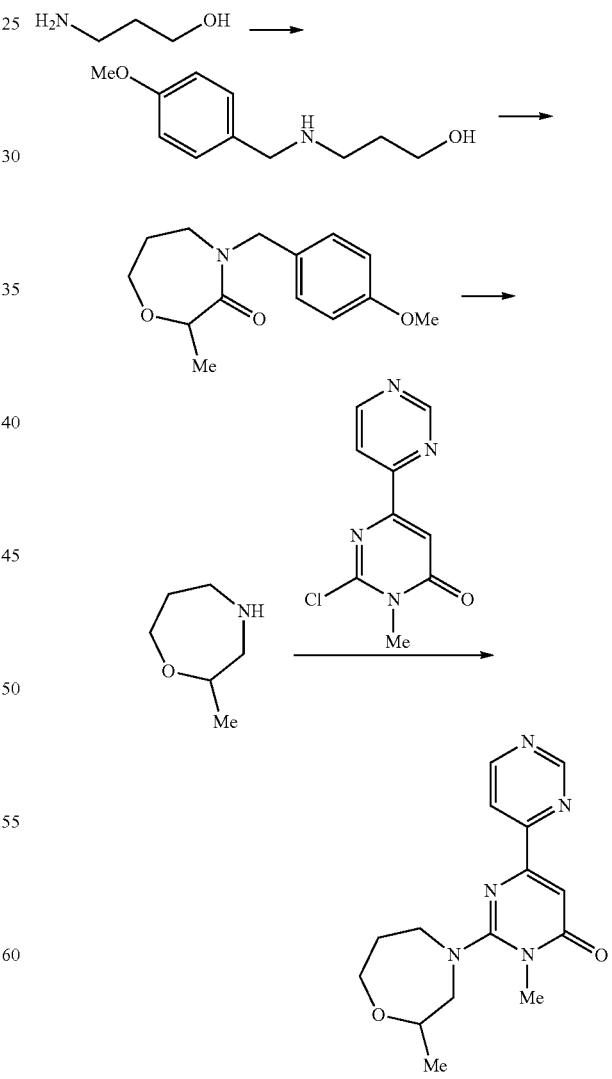

A051

To a solution of 3-amino-propan-1-ol (15.0 g, 200 mmol) in methanol (300 ml) was added para-methoxybenzaldehyde (28.6 g, 210 mmol) and a few drops of acetic acid at room temperature. The mixture was stirred at room temperature for 2 hours and cooled to 0° C. After the addition of sodium borohydride (11.4 g, 300 mmol), the mixture was stirred at room temperature for another 2 hours and acidified with 3N hydrochloric acid. The biphasic mixture was stirred at room temperature for 10 minutes. The organic solvent was evaporated under reduced pressure and the residue was partitioned between water and ethyl acetate. The aqueous phase was washed with ethyl acetate and basified with 6N sodium hydroxide. Extraction with chloroform was performed and the organic phase was dried over sodium sulfate followed by concentration in vacuo to afford 3-(4-methoxy-benzylamino)-propan-1-ol as pale yellow oil (16.4 g, 42%).

To a solution of 3-(4-methoxy-benzylamino)-propan-1-ol (2.00 g, 10.2 mmol) in dichloromethane (30 ml) was added triethylamine (1.09 g, 10.8 mmol) and 2-chloropropionyl chloride (1.37 g, 10.8 mmol) at 0° C. The mixture was stirred at 0° C. for one hour and partitioned between 0.5N hydrochloric acid and dichloromethane. The organic layer was washed with brine, dried over sodium sulfate and concentrated in vacuo. The residue was dissolved into 2-propanol (50 ml) and potassium hydroxide (1.15 g, 20.5 mmol) was added at 0° C. The resulting mixture was stirred at 0° C. for 4 hours and partitioned between saturated ammonium chloride solution and ethyl acetate. The organic layer was washed with brine, dried over sodium sulfate and concentrated in vacuo. The residue was purified by silica gel column chromatography (eluant: hexane/ethyl acetate=3/1) to afford 4-(4-methoxybenzyl)-2-methyl-[1,4]oxazepan-3-one as colorless oil (2.00 g, 78%).

To a solution of 4-(4-methoxy-benzyl)-2-methyl-[1,4]oxazepan-3-one (2.00 g, 8.02 mmol) in tetrahydrofuran (24 ml) was added 1M borane-tetrahydrofuran complex in tetrahydrofuran (27.3 ml, 27.3 mmol) at 0° C. The mixture was stirred at room temperature for 3 hours. After cooling to 0° C., methanol (20 ml) and 6N sodium hydroxide (20 ml) was added carefully. The resulting mixture was refluxed for 2 hours and cooled to room temperature. The solvent was removed under reduced pressure. The residue was partitioned between saturated ammonium chloride solution and ethyl acetate. The organic layer was washed with brine, dried over sodium sulfate and concentrated in vacuo. The residue was purified by silica gel column chromatography (eluant: hexane/ethyl acetate=1/1) to afford 4-(4-methoxybenzyl)-2-methyl-[1,4]oxazepane as colorless oil (1.66 g, 88%).

To a solution of 4-(4-methoxy-benzyl)-2-methyl-[1,4]oxazepane (1.66 g, 7.05 mmol) in 1,2-dichloroethane (12 ml) was added 1-chloroethyl chloroformate (2.52 g, 17.6 mmol) at room temperature. The mixture was refluxed for 5 hours and cooled to room temperature. After the addition of methanol (15 ml), the mixture was refluxed for 3 hours and concentrated in vacuo to afford the crude product. This crude product was partitioned between ether and 1N hydrochloric acid, and washed with ether. The water phase was basified with saturated aqueous sodium hydrogen carbonate. The product was extracted with dichloromethane. The organic layer was dried over sodium sulfate and the solvent was removed under reduced pressure carefully to avoid evaporating the product. To the resulting solution was added 4N hydrochloric acid in ethyl acetate. The solution was concentrated in vacuo to afford 2-methyl-[1,4]oxazepane hydrochloride as pale yellow oil (964 mg, 90%).

To a slurry of 2-Chloro-1-methyl-1H-[4,4']bipyrimidinyl-6-one (126 mg, 0.565 mmol) and 2-methyl-[1,4]oxazepane hydrochloride (100 mg, 0.660 mmol) was added triethylamine (172 mg, 1.70 mmol) at room temperature. The resulting mixture was stirred at room temperature for 10 hours and partitioned between water and ethyl acetate. The organic layer was washed with brine, dried over sodium sulfate and concentrated in vacuo. The residue was purified by silica gel column chromatography (eluant; ethyl acetate) to afford 1-methyl-2-(2-methyl-[1,4]oxazepan-4-yl)-1H-[4,4']bipyrimidinyl-6-one as white solid (A051) (103 mg, 61%).

Example 13

(R)-2-[2-(3-Bromo-phenyl)-[1,4]oxazepan-4-yl]-1-methyl-1H-[4,4']bipyrimidinyl-6-one (A079)

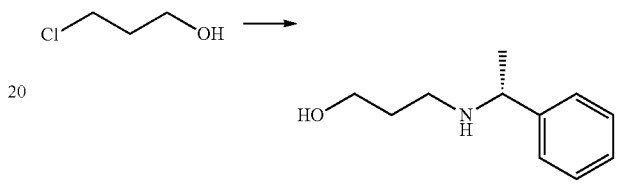

To a solution of (R)-1-phenylethanamine (364 g, 3.00 mol) in water (43.7 ml) was added 3-chloropropan-1-ol (142 g, 1.50 mol) at room temperature. The mixture was stirred at 100° C. for 5 hours. The resulting mixture was cooled to 0° C. and basified with saturated aqueous potassium carbonate. The organic layer was extracted with dichloromethane, dried over sodium sulfate, and concentrated in vacuo. The crude product was distilled under reduced pressure to remove excess (R)-1-phenylethanamine. The residue was diluted with chloroform and activated carbon was added to the solution. The mixture was refluxed for one hour and filtered through a pad of Celite. The filtrate was concentrated in vacuo to afford (R)-3-(1-phenylethylamino)propan-1-ol as pale yellow oil (224 g, 83%).

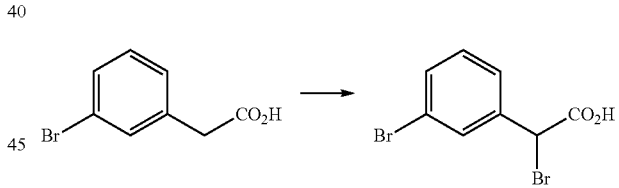

To a solution of 3-bromophenylacetic acid (25.0 g, 116 mmol) in carbon tetrachloride (200 ml) was added N-bromosuccinimide (22.8 g, 128 mmol) at room temperature. The mixture was refluxed for 3 hours and cooled to room temperature. The resulting precipitate was filtered off. The filtrate was concentrated in vacuo. The residue was purified by silica gel column chromatography (eluant: hexane/ethyl acetate=4/1) to afford bromo-(3-bromo-phenyl)-acetic acid as yellow liquid (27.8 g, 81%).

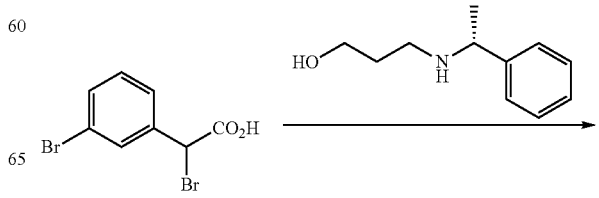

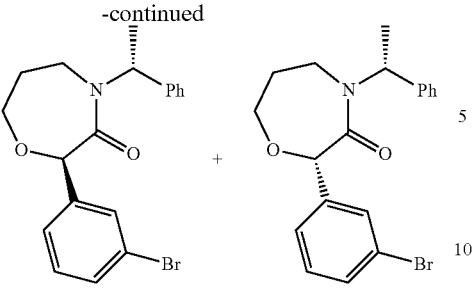

To a solution of bromo-(3-bromo-phenyl)-acetic acid (27.8 g, 94.6 mmol) in dichloromethane (200 ml) was added oxalyl-chloride (19.8 g, 156 mmol) and a few drops of N,N-dimethylformamide at room temperature. After the mixture was stirred at 40° C. for one hour, the solvent was removed under reduced pressure. The residue was dissolved in dichloromethane (30 ml) and the solution was added to a solution of (R)-3-(1-phenylethyl amino)propan-1-ol (18.6 g, 104 mmol) and triethylamine (11.6 g, 114 mmol) in dichloromethane (312 ml) at 0° C. The mixture was stirred for 1.5 hours at 0° C. and partitioned between 0.5 N hydrochloric acid and dichloromethane. The organic layer was washed with brine, dried over sodium sulfate and concentrated in vacuo. The residue was dissolved into 2-propanol (312 ml) and then potassium hydroxide (11.7 g, 208 mmol) was added at 0° C. The mixture was stirred at 0° C. for 3 hours and partitioned between saturated ammonium chloride solution and dichloromethane. The organic layer was washed with brine, dried over sodium sulfate and concentrated in vacuo. The crude mixture was triturated with ether. The resulting solid materials were collected by filtration and dried under reduced pressure to afford diastereomerically pure 2-(3-bromo-phenyl)-4-((R)-1-phenyl-ethyl)-[1,4]oxazepan-3-one (diastereomer 1) as white solid (9.71 g, 25%).

Rf value=0.43 (eluant: hexane/ethyl acetate=2/1)

$^1$H-NMR(400 MHz, CDCl$_3$) δ:1.26-1.35(1H, m), 1.50(3H, d, J=7.0 Hz), 1.73-1.84(1H, m), 3.13(1H, ddd, J=3.9, 6.3, 14.9 Hz), 3.48(1H, ddd, J=3.1, 10.2, 14.9 Hz), 3.67(1H, ddd, J=4.7, 11.0, 15.7 Hz), 4.15(1H, ddd, J=2.4, 7.0, 12.5 Hz), 5.26(1H, s), 6.06(1H, q, J=7.0 Hz), 7.23-7.33(2H, m), 7.35-7.37(4H, m), 7.39-7.42(1H, m), 7.44-7.46(1H, m), 7.63-7.64 (1H, m)

The mother liquid was concentrated in vacuo, and the residue was purified by silica gel column chromatography (eluant: hexane/ethyl acetate=4/1) to afford another diastereomer of 2-(3-bromo-phenyl)-4-((R)-1-phenyl-ethyl)-[1,4] oxazepan-3-one (diastereomer 2) as a colorless oil (10.3 g, 27%).

Rf value=0.35(eluant: hexane/ethyl acetate=2/1)

$^1$H-NMR (400 MHz, CDCl$_3$) δ: 1.54(3H, d, J=7.0 Hz), 1.63-1.79(2H, m), 3.17(1H, ddd, J=3.9, 6.3, 14.9 Hz), 3.42 (1H, ddd, J=3.9, 9.4, 14.9 Hz), 3.74(1H, ddd, J=5.5, 11.0, 15.7 Hz), 4.18(1H, ddd, J=2.4, 6.3, 12.5 Hz), 5.28(1H, s), 6.06(1H, q, J=7.0 Hz), 7.22-7.29(4H, m), 7.31-7.35(2H, m), 7.39-7.42(1H, m), 7.44-7.46(1H, m), 7.63-7.64(1H, m)

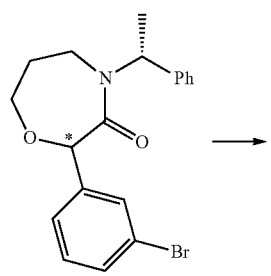

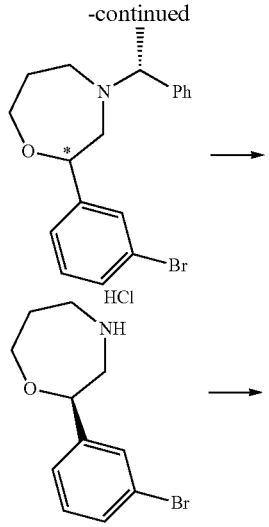

To a solution of 2-(3-bromo-phenyl)-4-((R)-1-phenyl-ethyl) -[1,4]oxazepan-3-one (diastereomer 1) (9.39 g, 25.1 mmol) in tetrahydrofuran (75 ml) was added 1.0M-borane-tetrahydrofuran complex in tetrahydrofuran (75.0 ml, 75.0 mmol) at 0° C. The mixture was refluxed for 4 hours. The mixture was cooled to 0° C. and methanol (100 ml) and 6.0 N aqueous sodium hydroxide (100 ml) was added carefully. The mixture was refluxed for 2 hours and cooled to room temperature. The solvent was removed under reduced pressure. The residue was partitioned between water and chloroform. The organic layer was washed with brine, dried over sodium sulfate, concentrated in vacuo. The residue was purified by silica gel column chromatography (eluant; hexane/ethyl acetate=4/1) to afford diastereomerically pure 2-(3-bromophenyl)-4-((R)-1-phenyl-ethyl)-[1,4]oxazepane as colorless oil (8.92 g, 99%).

To a solution of diastereomerically pure 2-(3-bromophenyl)-4-((R)-1-phenylethyl)-[1,4]oxazepane (8.92 g, 24.8 mmol) in 1,2-dichloroethane (42 ml) was added 1-chloroethyl chloroformate (8.85 g, 61.9 mmol) at room temperature. The mixture was refluxed for 5 hours and cooled to room temperature. After methanol (20 ml) was added, the solution was refluxed for another 5 hours. The mixture was concentrated under reduced pressure to afford the crude product. This crude product was washed with ether, dried under reduced pressure to yield 2-(3-bromophenyl)-[1,4]oxazepane as white solid (7.05 g, 97%). An analytical sample for X-ray was obtained by crystallization from ethanol, and the absolute configuration of this compound was found to be the (R)- configuration by a method using a Flack parameter. The absolute configuration was determined by X-ray crystallography of a sample crystallized from ethanol.

To a solution of 2-chloro-3-methyl-6-(pyrimidin-4-yl)-3H-pyrimidin-4-one (1.00 g, 4.49 mmol) and (R)-2-(3-bromophenyl)-[1,4]oxazepane (1.58 g, 5.39 mmol) was added triethylamine (1.36 g, 13.5 mmol) at room temperature. The mixture was stirred at room temperature for 9 hours. The mixture was partitioned between water and chloroform. The organic layer was washed with brine, dried over sodium sulfate and concentrated in vacuo. The residue was purified by silica gel column chromatography (eluant: ethyl acetate) to afford (R)-2-[2-(3-bromo-phenyl)-[1,4]oxazepan-4-yl]-1-methyl-1H-[4,4']bipyrimidinyl-6-one (A079) as white solid (1.65 g, 83%).

Example 14

(S)-2-[2-(3-Cyanophenyl)-[1,4]oxazepan-4-yl]-1-methyl-1H-[4,4']bipyrimidinyl-6-one (A039)

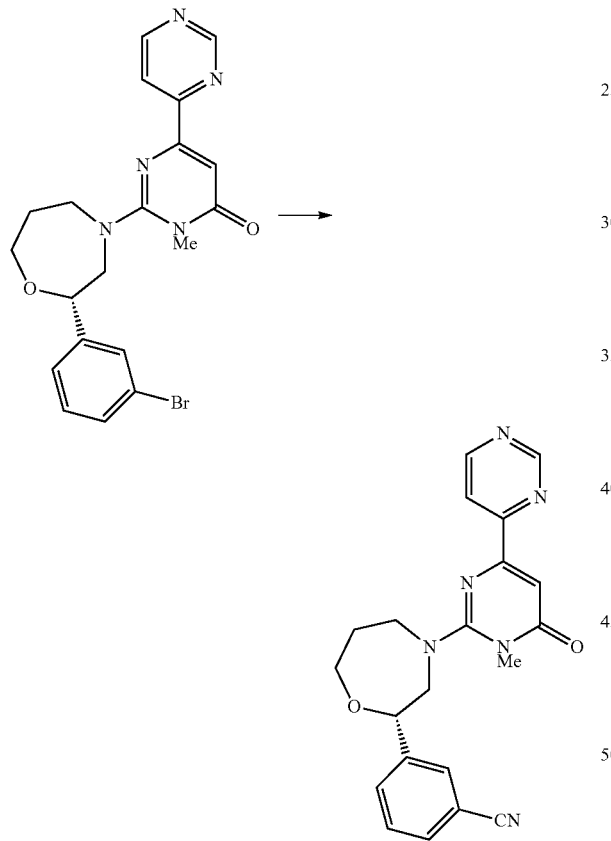

To a solution of (S)-2-[2-(3-bromophenyl)-[1,4]oxazepan-4-yl]-1-methyl-1H-[4,4']bipyrimidinyl-6-one (A079) (1.0 g, 2.26 mmol) in N,N-dimethylacetamide (7.5 ml) was added zinc cyanide (0.292 g, 2.49 mmol) and tetrakis(triphenylphosphine) palladium(0) (523 mg, 0.452 mmol) at room temperature under nitrogen atmosphere. The mixture was stirred at 110° C. for 8 hours. The resulting mixture was filtered through a pad of Celite and partitioned between aqueous sodium hydrogen carbonate and chloroform. The organic layer was washed with water, dried over sodium sulfate and concentrated in vacuo. The residue was purified by silica gel column chromatography (eluant: chloroform/acetone=4/1) to afford (R)-2-[2-(3-cyanophenyl)-[1,4]oxazepan-4-yl]-1-methyl-1H-[4,4']bipyrimidinyl-6-one (A039) as pale yellow solid (745 mg, 85%).

Example 15

(S)-1-Methyl-2-{2-[3-(5-methyl-[1,2,4]oxadiazol-3-yl)-phenyl]-[1,4]oxazepan-4-yl}-1H-[4,4']bipyrimidinyl-6-one (A030)

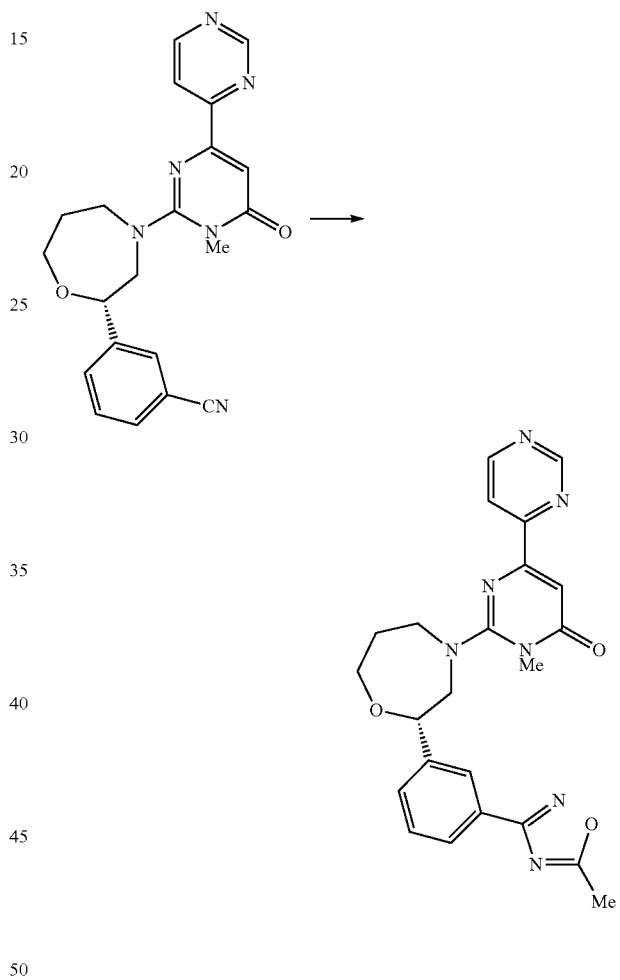

To a solution of (S)-2-[2-(3-cyano-phenyl)-[1,4]oxazepan-4-yl]-1-methyl-1H-[4,4']bipyrimidinyl-6-one (A039) (250 mg, 0.644 mmol) in ethanol (1.29 ml) was added 50 wt. %—hydroxylamine aqueous solution (128 mg, 1.93 mmol) at room temperature. The mixture was stirred at 80° C. for 2 hours and concentrated. The residue was partitioned between water and chloroform. The organic layer was dried over sodium sulfate and concentrated in vacuo. To the residue was added toluene (1.29 ml) and N,N-dimethylformamide dimethylacetal (190 mg, 1.29 mmol) at room temperature. After the mixture was refluxed for 2 hours, the solvent was evaporated. The residue was purified by silica gel column chromatography (eluant: chloroform/methanol=98/2) to afford (S)-1-Methyl-2-{2-[3-(5-methyl-[1,2,4]oxadiazol-3-yl)phenyl]-[1,4]oxazepan-4-yl}-1H-[4,4']bipyrimidinyl-6-one (A030) as white solid (254 mg, 89%).

Example 16

(S)-3-[4-(1-Methyl-6-oxo-1,6-dihydro-[4,4']bipyrimidinyl-2-yl)-[1,4]oxazepan-2-yl]-benzamide (A015)

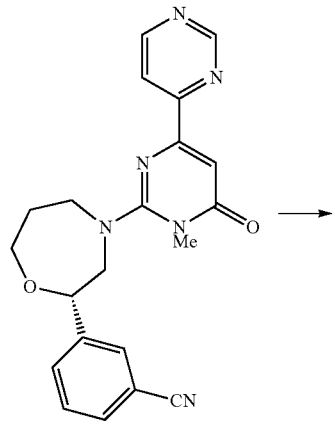

↓

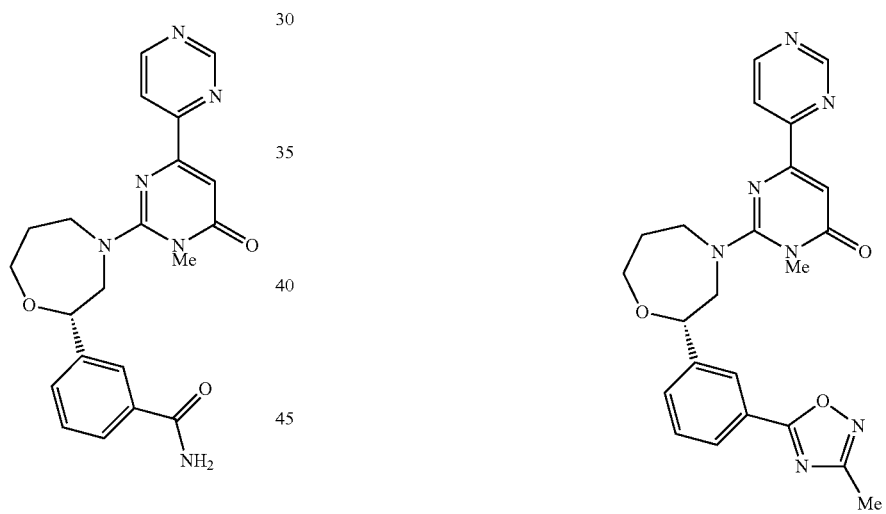

To a solution of (S)-2-[2-(3-cyano-phenyl)-[1,4]oxazepan-4-yl]-1-methyl-1H-[4,4']bipyrimidinyl-6-one (A039) (300 mg, 0.772 mmol), tetrahydrofuran (1.90 ml) and 3.0N-sodium carbonate (1.90 ml) in ethanol (1.90 ml) was added 30%-hydrogen peroxide (1.90 ml) at room temperature. The mixture was stirred at room temperature for 2 hours and partitioned between water and chloroform. The organic layer was dried over sodium sulfate and concentrated in vacuo. The residue was washed with diethyl ether to afford (S)-3-[4-(1-Methyl-6-oxo-1,6-dihydro-[4,4']bipyrimidinyl-2-yl)-[1,4]oxazepan-2-yl]-benzamide (A015) as pale yellow solid (293 mg, 93%).

Example 17

(S)-1-Methyl-2-{2-[3-(3-methyl-[1,2,4]oxadiazol-5-yl)-phenyl]-[1,4]oxazepan-4-yl}-1H-[4,4']bipyrimidinyl-6-one (A045)

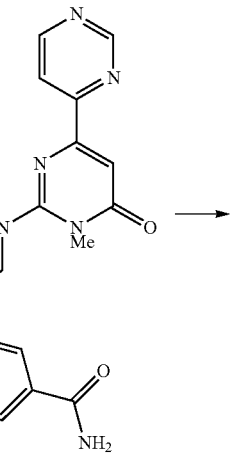

↓

A solution of (S)-3-[4-(1-Methyl-6-oxo-1,6-dihydro-[4,4'] bipyrimidinyl-2-yl)-[1,4]oxazepan-2-yl]-benzamide (A015) (200 mg, 0.492 mmol) in N,N-dimethylacetamide dimethyl acetal (0.760 ml) was stirred at 110° C. for one hour. The mixture was concentrated under reduced pressure, and then 1,4-dioxane (0.820 ml), acetic acid (0.820 ml), 1N-sodium hydroxide (0.490 ml) and hydroxylamine hydrochloride (43.1 mg 0.491 mmol) was added. The mixture was stirred at 100° C. for 3 hours and partitioned between water and chloroform. The organic layer was washed with brine and aqueous sodium hydrogen carbonate, dried over sodium sulfate, and concentrated under reduced pressure. The residue was purified by silica gel column chromatography (eluant; chloroform/methanol=98/2) to afford (S)-1-Methyl-2-{2-[3-(3-methyl-[1,2,4]oxadiazol-5-yl)-phenyl]-[1,4]oxazepan-4-yl}-1H-[4,4']bipyrimidinyl-6-one (A045) as pale yellow solid (116 mg, 53%).

Example 18

(R)-1-Methyl-2-(3-methyl-[1,4]oxazepan-4-yl)-1H-[4,4']bipyrimidinyl-6-one (A064)

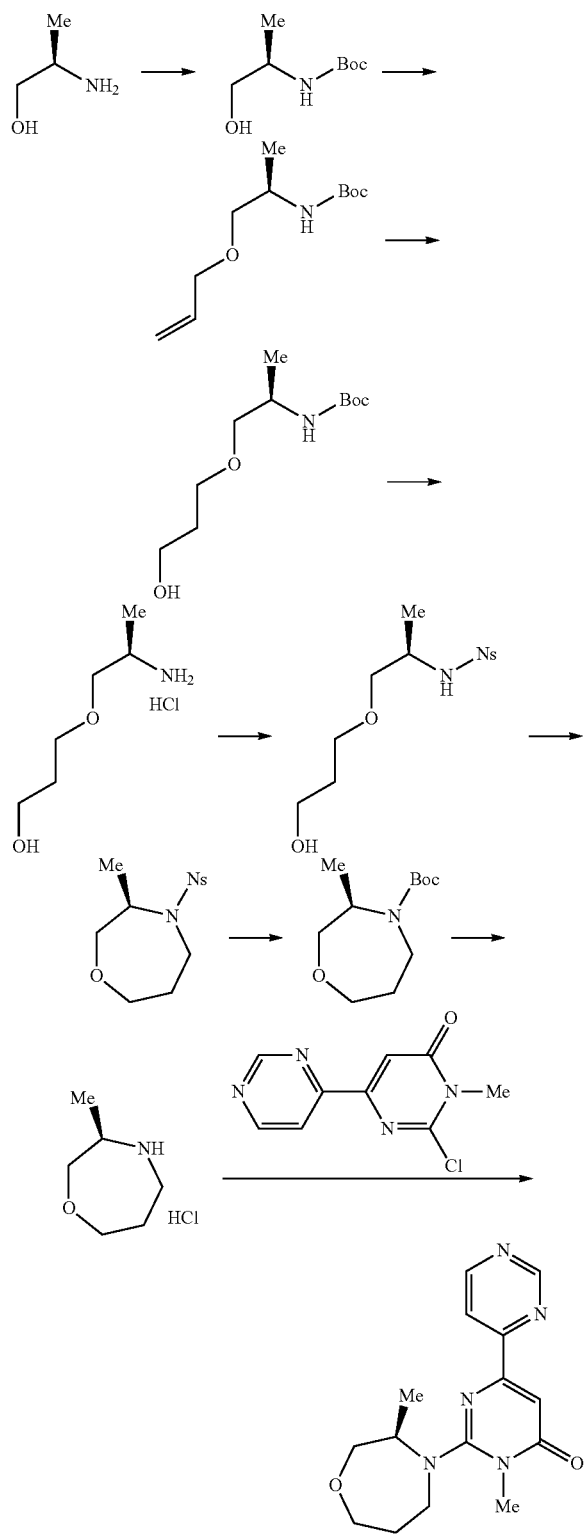

To a solution of (R)-2-amino-1-propanol (5 g, 67 mmol) in tetrahydrofuran (THF) (50 mL) was added 1M sodium hydroxide aqueous solution (150 mL, 150 mmol) and a solution of di-tert-butyl dicarbonate (14.5 g, 67 mmol) in THF (50 mL) at 0° C. and stirred for 15 hours. The reaction mixture was diluted with ethyl acetate. The organic phase was separated from the aqueous phase and dried over anhydrous sodium sulfate. After the solvent was removed under reduced pressure, the crude material was purified by flash column chromatography on silica gel (hexane/ethyl acetate=1/1 as an eluant) to afford (R)-(2-hydroxy-1-methyl-ethyl)-carbamic acid tert-butyl ester (9.0 g, 51.4 mmol, 77%) as colorless oil.

(R)-(2-Hydroxy-1-methyl-ethyl)-carbamic acid tert-butyl ester (4.0 g, 22.8 mmol) was dissolved in 50% aqueous sodium hydroxide solution (15 mL) at 0° C. and to the resulting solution was added allylbromide (2.2 mL, 25 mmol) and catalytic amount of tetrabutylammonium hydrogensulfate (0.85 g, 2.5 mmol) at room temperature and stirred for 4 hours. The resulting solution was diluted with water and extracted with ethyl acetate. The organic extracts were dried over anhydrous sodium sulfate and concentrated. The resulting crude allyl ether was dissolved in THF (75 mL) at room temperature and to the resulting solution was added a solution of 9-borabicyclo[3,3,1]nonane in THF (0.5 M, 100 mL, 50 mmol). After 5 hour-stirring, to the resulting solution was added water (8 mL), 3N aqueous sodium hydroxide solution (8.1 mL) and 30% aqueous hydrogen peroxide solution (8.2 mL) at room temperature and warmed to 40° C. followed by stirring for 30 minutes. The organic solvent was removed under reduced pressure and the residue was diluted with brine. Extraction was performed with ethyl acetate and the extracts were dried over magnesium sulfate. After concentration, the residual materials were purified by flash column chromatography on silica gel to afford (R)-[2-(3-hydroxypropoxy)-1-methyl-ethyl]carbamic acid tert-butyl ester (3.0 g, 12.9 mmol, 56%) as a colorless oil.

(R)-[2-(3-Hydroxy-propoxy)-1-methyl-ethyl]-carbamic acid tert-butyl ester was dissolved in 4N solution of hydrogen chloride in ethyl acetate (20 ml, 80 mmol) at room temperature. After stirring for 3 hours, the resulting mixture was concentrated. The viscous oil was mixed with dichloromethane (50 mL) and to the resulting mixture was added triethylamine (5.0 mL, 36 mmol) and 2-nitrobenzenesulfonylchloride (2.7 g, 12 mmol) at 0° C. The reaction mixture was stirred for one hour and diluted with water. Extractive workup with chloroform was performed and the organic solution was dried over sodium sulfate. Concentration followed by purification by flash column chromatography on silica gel (ethyl acetate only as an eluant) led to (R)—N-[2-(3-Hydroxy-propoxy)-1-methyl-ethyl]-2-nitro-benzenesulfonamide (1.3 g, 4.1 mmol, 34%) as yellow solid.

To a solution of (R)—N-[2-(3-hydroxy-propoxy)-1-methyl-ethyl]-2-nitro benzene sulfonamide (1.3 g, 4.1 mmol) in THF (50 mL) was added triphenylphosphine (1.7 g, 6.6 mmol) and a 40% wt solution of diethyl azodicarboxylate (DEAD) in toluene (3 mL, 6.6 mmol) at room temperature. The resulting mixture was stirred for 18 hours and concentrated. The residue was passed through flash column chromatography on silica gel (hexane/ethyl acetate=1/1 as an eluant) to remove triphenylphosphine oxide. The resulting brown viscous material containing (R)-3-methyl-4-(2-nitro-benzenesulfonyl)-[1,4]oxazepane was dissolved in dimethylformamide (DMF) (10 mL) and thioglycolic acid (0.72 mL, 10 mmol) and lithium hydroxide monohydrate (1 g, 24 mmol) was added to the mixture at room temperature. After stirring for 18 hours, the reaction mixture was diluted with water and extracted with ethyl acetate. The organic extracts were dried over sodium sulfate and concentrated. The residue was dissolved in THF (10 mL) and 1M aqueous sodium hydroxide solution (10 mL) and di-tert-butyl dicarbonate (1.0 g, 4.5 mmol) were added to the solution at room temperature. After stirring for 5 hours, the reaction mixture was evaporated to remove organic solvent and extracted with ethyl acetate. The organic solution was dried over sodium sulfate and concentrated. The residue was purified by flash column chromatography on silica gel (hexane/ethyl acetate=3/1 as an eluant) to yield (R)-3-methyl-[1,4]oxazepane-4-carboxylic acid tert-butyl ester (0.48 g, 2.2 mmol, 56%) as colorless oil.

(R)-3-Methyl-[1,4]oxazepane-4-carboxylic acid tert-butyl ester (0.48 g, 2.2 mmol) was dissolved in a 4N solution of hydrogen chloride in ethyl acetate (5 mL) at room temperature and the mixture was stirred for 3 hours. After concentration of the reaction mixture, the residue was triturated by diisopropyl ether and filtered to collect (R)-3-methyl-[1,4] oxazepane hydrochloride (0.23 g, 1.5 mmol, 67%) as white solid.

To a mixture of (R)-3-methyl-[1,4]oxazepane hydrochloride (0.10 g, 0.66 mmol) and 2-chloro-3-methyl-6-(pyrimidin-4-O-3H-pyrimidin-4-one (0.13 g, 0.6 mmol) in N-methylpyrrolidone (3 mL) was added triethylamine (0.25 mL, 1.8 mmol) at room temperature and the resulting mixture was warmed to 80° C. After stirring for 4 hours, the reaction mixture was cooled to room temperature and treated with water. The resulting organic materials were extracted with chloroform and dried over sodium sulfate. Concentration of the organic solution and purification of the residue by flash column chromatography on silica gel followed by crystallization from ethanol/hexane afforded (R)-1-methyl-2-(3-methyl-[1,4]oxazepan-4-O-1H-[4,4']bipyrimidinyl-6-one (A064) (0.06 g, 0.19 mmol, 31%) as colorless crystalline.

The compounds in the following table were prepared in the same manner as the methods described above. The compound numbers in the following table correspond to those shown in the above described table of preferred compounds.

TABLE 2

| Comp No. | $^1$H-NMR (solvent) δ: | [M + H] | [alpha]D |
|---|---|---|---|
| A001 | (CDCl3) 2.08-2.14(2H, m), 3.53(3H, s), 3.61-3.66(4H, m), 3.89(2H, t, J = 5.5 Hz), 3.92-3.94(2H, m), 6.79(1H, s), 7.93(1H, dd, J = 4.7, 6.3 Hz), 8.51(1H, d, J = 4.7 Hz), 8.55(1H, d, J = 3.1 Hz) | 305 | |
| A002 | (CDCl3) 2.09-2.15(2H, m), 3.54(3H, s), 3.62-3.68(4H, m), 3.89(2H, t, J = 5.5 Hz), 3.93-3.96(2H, m), 7.26(1H, s), 8.13(1H, dd, J = 1.6, 5.5 Hz), 8.87(1H, d, J = 4.7 Hz), 9.28(1H, s) | 288 | |
| A003 | (CDCl3) 2.15(2H, m), 3.42(2H, t, J = 5.7 Hz), 3.50(3H, s), 3.63(2H, t, J = 6.3 Hz), 7.73(4H, dtd, J = 24.6, 3.1, 3.3 Hz), 6.68(2H, dd, J = 5.4, 3.4 Hz), 6.77(1H, s), 6.96(2H, t, J = 8.5 Hz), 7.90(1H, dd, J = 6.6, 5.1 Hz), 8.51(1H, d, J = 5.1 Hz), 8.55(1H, d, J = 3.0 Hz) | 398 | |
| A004 | (CDCl3) 2.16(2H, m), 3.43(2H, t, J = 5.7 Hz), 3.51(3H, s), 3.71(2H, t, J = 6.3 Hz), 3.75(4H, dtd, J = 24.6, 3.1, 3.3 Hz), 6.68(2H, dd, J = 5.4, 3.4 Hz), 6.97(2H, t, J = 8.5 Hz), 8.11(1H, dd, J = 1.5, 6.3 Hz), 8.87(1H, d, J = 5.4 Hz), 9.28(1H, d, J = 1.5 Hz) | 381 | |
| A005 | (CDCl3) 2.16(2H, m), 3.44(2H, t, J = 5.7 Hz), 3.50(3H, s), 3.61(2H, t, J = 6.3 Hz), 3.76(4H, dtd, J = 24.6, 3.1, 3.3 Hz), 6.60(1H, s), 6.68(2H, dd, J = 5.4, 3.4 Hz), 6.93(2H, t, J = 8.5 Hz), 7.72(2H, d, J = 6.3 Hz), 8.71(2H, d, J = 6.0 Hz) | 380 | |
| A006 | (CDCl3) 2.12-2.22(1H, m), 2.24-2.34(1H, m), 3.42(1H, dd, J = 9.4, 14.1 Hz), 3.54(3H, s), 3.61-3.68(1H, m), 3.76(1H, dt, J = 5.5, 14.1 Hz), 3.83-3.89(1H, m), 4.03(1H, d, J = 14.1 Hz), 4.25(1H, dt, J = 5.5, 12.5 Hz), 4.92(1H, dd, J = 2.4, 9.4 Hz), 6.78(1H, s), 7.29-7.38(5H, m), 7.89(1H, dd, J = 4.7, 6.3 Hz), 8.51(1H, d, J = 4.7 Hz), 8.56(1H, d, J = 3.1 Hz) | 381 | |
| A007 | (CDCl3) 2.12-2.22(1H, m), 2.27-2.37(1H, m), 3.40(1H, dd, J = 8.6, 14.1 Hz), 3.53(3H, s), 3.62-3.74(2H, m), 3.84-3.90(1H, m), 4.05(1H, dd, J = 1.6, 14.9 Hz), 4.26(1H, dt, J = 5.5, 13.3 Hz), 5.01(1H, dd, J = 2.4, 8.6 Hz), 5.51-5.67(1H, brs), 6.00-6.16(1H, brs), 6.76(1H, s), 7.47(2H, d, J = 8.6 Hz), 7.81(2H, d, J = 8.6 Hz), 7.85(1H, dd, J = 5.5, 7.0 Hz), 8.51(1H, d, J = 4.7 Hz), 8.57(1H, d, J = 3.1 Hz) | 424 | |
| A008 | (CDCl3) 2.10-2.20(1H, m), 2.23-2.33(1H, m), 3.38(1H, dd, J = 8.6, 14.1 Hz), 3.54(3H, s), 3.60-3.74(2H, m), 3.80-3.86(1H, m), 4.03(1H, dd, J = 1.6, 14.1 Hz), 4.23(1H, dt, J = 4.7, 12.5 Hz), 4.93(1H, dd, J = 2.4, 9.4 Hz), 6.77(1H, s), 7.23(1H, t, J = 7.8 Hz), 7.27-7.30(1H, m), 7.43-7.46(1H, m), 7.56-7.57(1H, m), 7.86(1H, dd, J = 4.7, 6.3 Hz), 8.54(1H, d, J = 4.7 Hz), 8.57(1H, d, J = 3.1 Hz) | 459 | |
| A009 | (CDCl3) 2.14-2.34(2H, m), 3.38(1H, dd, J = 9.4, 14.1 Hz), 3.56(3H, s), 3.57-3.64(1H, m), 3.75(1H, dt, J = 5.5, 14.1 Hz), 3.83-3.90(1H, m), 4.04(1H, dd, J = 1.6, 14.1 Hz), 4.24(1H, dt, J = 5.5, 12.5 Hz), 4.88(1H, dd, J = 2.4, 9.4 Hz), 7.27-7.30(3H, m), 7.52(2H, d, J = 8.6 Hz), 8.06(1H, dd, J = 1.6, 5.5 Hz), 8.86(1H, d, J = 5.5 Hz), 9.28(1H, d, J = 1.6 Hz) | 442 | |
| A010 | (CDCl3) 2.12-2.21(1H, m), 2.22-2.32(1H, m), 3.35(1H, dd, J = 9.4, 14.9 Hz), 3.54(3H, s), 3.58-3.65(1H, m), 3.72(1H, dt, J = 5.5, 14.9 Hz), 3.81-3.87(1H, m), 4.01(1H, dd, J = 2.4, 14.1 Hz), 4.23(1H, dt, J = 5.5, 12.5 Hz), 4.90(1H, dd, J = 1.6, 9.4 Hz), 6.77(1H, s), 7.26(2H, d, J = 8.6 Hz), 7.50(2H, d, J = 8.6 Hz), 7.84(1H, dd, J = 4.7, 6.3 Hz), 8.51(1H, d, J = 4.7 Hz), 8.57(1H, d, J = 3.1 Hz) | 459 | |
| A011 | (CDCl3) 2.12-2.22(1H, m), 2.23-2.33(1H, m), 3.38(1H, dd, J = 9.4, 14.9 Hz), 3.54(3H, s), 3.60-3.67 (1H, m), 3.74(1H, dt, J = 5.5, 14.1 Hz), 3.81-3.88(1H, m), 4.00(1H, dd, J = 14.9 Hz), 4.24(1H, dt, J = 5.5, 12.5 Hz), 4.91(1H, dd, J = 2.4, 9.4 Hz), 6.77(1H, s), 7.06(2H, t, J = 8.6 Hz), 7.35(2H, dd, J = 5.5, 8.6 Hz), 7.86(1H, dd, J = 5.5, 7.0 Hz), 8.51(1H, d, J = 4.7 Hz), 8.57(1H, d, J = 3.1 Hz) | 399 | |
| A012 | (CDCl3) 2.12-2.21(1H, m), 2.26-2.36(1H, m), 3.43(1H, dd, J = 8.6, 14.1 Hz), 3.53(3H, s), 3.62-3.76(2H, m), 3.83-3.90(1H, m), 4.05(1H, dd, J = 1.6, | 424 | |

TABLE 2-continued

| Comp No. | ¹H-NMR (solvent) δ: | [M + H] | [alpha]D |
|---|---|---|---|
| | 14.1 Hz), 4.25(1H, dt, J = 5.5, 12.5 Hz), 5.01(1H, dd, J = 2.4, 9.4 Hz), 5.50-5.69(1H, brs), 5.99-6.18(1H, brs), 6.76(1H, s), 7.45(1H, t, J = 7.8 Hz), 7.52-7.55(1H, m), 7.71-7.74(1H, m), 7.87(1H, dd, J = 4.7, 6.3 Hz), 7.89-7.91(1H, m), 8.53(1H, d, J = 5.5 Hz), 8.57(1H, d, J = 3.1 Hz) | | |
| A013 | (CDCl3) 2.12-2.21(1H, m), 2.23-2.33(1H, m), 3.34(1H, dd, J = 9.4, 14.9 Hz), 3.55(3H, s), 3.59-3.66(1H, m), 3.72(1H, dt, J = 5.5, 14.9 Hz), 3.82-3.89(1H, m), 4.05(1H, dd, J = 1.6, 14.1 Hz), 4.25(1H, dt, J = 4.7, 12.5 Hz), 5.04(1H, dd, J = 2.4, 9.4 Hz), 6.76(1H, s), 7.51(2H, d, J = 7.8 Hz), 7.66(2H, d, J = 7.8 Hz), 7.81(1H, dd, J = 5.5, 7.0 Hz), 8.51(1H, d, J = 4.7 Hz), 8.58(1H, d, J = 3.1 Hz) | 406 | |
| A014 | (CDCl3) 2.15-2.29(2H, m), 3.44(3H, s), 3.65(1H, ddd, J = 3.0, 9.2, 14.3 Hz), 3.72-3.76(2H, m), 3.82-3.86(1H, m), 3.96(1H, ddd, J = 2.2, 9.4, 13.2 Hz), 4.10(1H, dt, J = 3.4, 13.3 Hz), 4.99(1H, dd, J = 3.4, 9.6 Hz), 6.50(1H, s), 7.15-7.22(2H, m), 7.31-7.36(1H, m), 7.51(1H, dt, J = 1.4, 7.7 Hz), 8.00(1H, dd, J = 4.9, 6.8), 8.56(1H, d, J = 4.8 Hz), 8.70(1H, d, J = 3.1 Hz) | 399 | |
| A015 | (CDCl3) 2.14-2.23(1H, m), 2.27-2.37(1H, m), 3.46(1H, dd, J = 9.4, 14.1 Hz), 3.55(3H, s), 3.62-3.68(1H, m), 3.74(1H, dt, J = 5.5, 14.1 Hz), 3.85-3.92(1H, m), 4.08(1H, dd, J = 1.6, 14.1 Hz), 4.26(1H, dt, J = 5.5, 12.5 Hz), 5.00(1H, dd, J = 2.4, 9.4 Hz), 5.55-5.72(1H, brs), 6.05-6.22(1H, brs), 7.26(1H, s), 7.47(1H, t, J = 7.8 Hz), 7.57(1H, d, J = 7.8 Hz), 7.73(1H, dt, J = 1.6, 7.8 Hz), 7.94(1H, t, J = 1.6 Hz), 8.10(1H, dd, J = 1.6, 5.5 Hz), 8.89(1H, d, J = 5.5 Hz), 9.28(1H, d, J = 1.6 Hz) | 407 | |
| A016 | (CDCl3) 2.11-2.21(1H, m), 2.25-2.36(1H, m), 2.66(3H, s), 3.47(1H, dd, J = 8.6, 14.1 Hz), 3.55(3H, s), 3.63-3.76(2H, m), 3.83-3.90(1H, m), 4.07(1H, dd, J = 1.6, 12.5 Hz), 4.26(1H, dt, J = 4.7, 12.5 Hz), 5.04(1H, dd, J = 2.4, 9.4 Hz), 6.77(1H, s), 7.49(1H, t, J = 7.8 Hz), 7.53(1H, dt, J = 1.6, 7.8 Hz), 7.91(1H, dd, J = 4.7, 6.3 Hz), 8.01(1H, dt, J = 1.6, 7.0 Hz), 8.11-8.12(1H, m), 8.53(1H, d, J = 5.5 Hz), 8.56(1H, d, J = 3.1 Hz) | 463 | |
| A017 | (CDCl3) 2.13-2.23(1H, m), 2.28-2.38(1H, m), 3.42(1H, dd, J = 9.4, 14.9 Hz), 3.53(3H, s), 3.63-3.77(2H, m), 3.85-3.91(1H, m), 4.08(1H, dd, J = 2.4, 14.9 Hz), 4.27(1H, dt, J = 4.7, 12.5 Hz), 5.03(1H, dd, J = 2.4, 9.4 Hz), 5.52-5.71(1H, brs), 6.02-6.19(1H, brs), 6.61(1H, s), 7.49(2H, d, J = 8.6 Hz), 7.76-7.77(2H, m), 7.82(2H, d, J = 8.6 Hz), 8.71-8.73(2H, m) | 406 | |
| A018 | (CDCl3) 2.15-2.24(1H, m), 2.29-2.39(1H, m), 3.44(1H, dd, J = 8.6, 14.1 Hz), 3.53(3H, s), 3.61-3.68(1H, m), 3.73(1H, dt, J = 5.5, 14.9 Hz), 3.87-3.93(1H, m), 4.07(1H, dd, J = 1.6, 14.9 Hz), 4.27(1H, dt, J = 5.5, 12.5 Hz), 4.99(1H, dd, J = 2.4, 9.4 Hz), 5.50-5.69(1H, brs), 6.02-6.19(1H, brs), 7.27(1H, s), 7.49(2H, d, J = 8.6 Hz), 7.83(2H, d, J = 8.6 Hz), 8.06-8.08(1H, m), 8.87(1H, d, J = 4.7 Hz), 9.29(1H, d, J = 1.6 Hz) | 407 | |
| A019 | (CDCl3) 2.13-2.23(1H, m), 2.25-2.35(1H, m), 2.48(3H, s), 3.41(1H, dd, J = 9.4, 14.9 Hz), 3.56(3H, s), 3.61-3.68(1H, m), 3.74(1H, dt, J = 5.5, 14.1 Hz), 3.85-3.92(1H, m), 4.08(1H, dd, J = 1.6, 14.1 Hz), 4.27(1H, dt, J = 5.5, 12.5 Hz), 5.04(1H, dd, J = 2.4, 9.4 Hz), 6.77(1H, s), 7.55(2H, d, J = 8.6 Hz), 7.85(1H, dd, J = 4.7, 6.3 Hz), 8.12(2H, d, J = 8.6 Hz), 8.51(1H, d, J = 4.7 Hz), 8.58(1H, d, J = 3.1 Hz) | 463 | |
| A020 | (CDCl3) 2.12-2.21(1H, m), 2.24-2.35(1H, m), 3.36(1H, dd, J = 8.6, 14.1 Hz), 3.55(3H, s), 3.60-3.74(2H, m), 3.83-3.89(1H, m), 4.05(1H, dd, J = 1.6, 14.1 Hz), 4.25(1H, dt, J = 4.7, 12.5 Hz), 5.01(1H, dd, J = 2.4, 8.6 Hz), 6.77(1H, s), 7.47(1H, t, J = 7.8 Hz), 7.58-7.62(2H, m), 7.74-7.75(1H, m), 7.82(1H, dd, J = 4.7, 6.3 Hz), 8.53(1H, d, J = 5.5 Hz), 8.58(1H, d, J = 3.1 Hz) | 406 | |
| A021 | (CDCl3) 2.13-2.22(1H, m), 2.23-2.33(1H, m), 3.37(1H, dd, J = 9.4, 14.1 Hz), 3.54(3H, s), 3.59-3.66(1H, m), 3.75(1H, dt, J = 5.5, 14.1 Hz), 3.82-3.88(1H, m), 4.05(1H, dd, J = 1.6, 15.7 Hz), 4.24(1H, dt, J = 5.5, 12.5 Hz), 4.92(1H, dd, J = 2.4, 9.4 Hz), 6.62(1H, s), 7.28(2H, d, J = 8.6 Hz), 7.51(2H, d, J = 8.6 Hz), 7.75-7.77(2H, m), 8.71-8.73(2H, m) | 441 | |
| A022 | (CDCl3) 2.13-2.23(1H, m), 2.24-2.34(1H, m), 3.40(1H, dd, J = 9.4, 14.1 Hz), 3.54(3H, s), 3.61-3.68 (1H, m), 3.76(1H, dt, J = 5.5, 14.9 Hz), 3.82-3.89(1H, m), 4.04(1H, d, J = 14.1 Hz), 4.24(1H, dt, J = 5.5, 12.5 Hz), 4.93(1H, dd, J = 2.4, 9.4 Hz), 6.62(1H, s), 7.07(2H, t, J = 8.6 Hz), 7.37(2H, dd, J = 5.5, 8.6 Hz), 7.75-7.77(2H, m), 8.71-8.72(2H, m) | 381 | |
| A023 | (CDCl3) 2.12-2.21(1H, m), 2.25-2.35(1H, m), 3.40(1H, dd, J = 9.4, 14.9 Hz), 3.54(3H, s), 3.61-3.76(2H, m), 3.81-3.87(1H, m), 4.06(1H, dd, J = 1.6, 14.9 Hz), 4.24(1H, dt, J = 5.5, 13.3 Hz), 4.95(1H, dd, J = 2.4, 9.4 Hz), 6.62(1H, s), 7.23-7.27(1H, m), 7.29-7.32(1H, m), 7.44-7.47(1H, m), 7.59-7.60(1H, m), 7.76-7.78(2H, m), 8.73-8.74(2H, m) | 441 | |
| A024 | (CDCl3) 2.12-2.21(1H, m), 2.25-2.35(1H, m), 3.40(1H, dd, J = 9.4, 14.9 Hz), 3.54(3H, s), 3.61-3.76(2H, m), 3.81-3.87(1H, m), 4.06(1H, dd, J = 2.4, 14.1 Hz), 4.24(1H, dt, J = 5.5, 13.3 Hz), 4.95(1H, dd, J = 2.4, 9.4 Hz), 6.62(1H, s), 7.23-7.27(1H, m), 7.29-7.32(1H, m), 7.44-7.47(1H, m), 7.59-7.60(1H, m), 7.76-7.78(2H, m), 8.73-8.74(2H, m) | 441 | |
| A025 | (CDCl3) 2.10-2.20(1H, m), 2.23-2.33(1H, m), 3.38(1H, dd, J = 8.6, 14.1 Hz), 3.54(3H, s), 3.60-3.74(2H, m), 3.80-3.86(1H, m), 4.03(1H, dd, J = 1.6, 14.1 Hz), 4.23(1H, dt, J = 4.7, 12.5 Hz), 4.93(1H, dd, J = 1.6, 8.6 Hz), 6.77(1H, s), 7.23(1H, t, J = 7.8 Hz), 7.27-7.30(1H, m), 7.43-7.46(1H, m), 7.56-7.57(1H, m), 7.86(1H, dd, J = 4.7, 6.3 Hz), 8.53(1H, d, J = 5.5 Hz), 8.57(1H, d, J = 3.1 Hz) | 459 | |
| A026 | (CDCl3) 2.14-2.35(2H, m), 3.45(1H, dd, J = 9.4, 14.9 Hz), 3.55(3H, s), 3.61-3.68(1H, m), 3.78(1H, dt, J = 5.5, 14.1 Hz), 3.84-3.91(1H, m), 4.06(1H, d, | 364 | |

TABLE 2-continued

| Comp No. | ¹H-NMR (solvent) δ: | [M + H] | [alpha]D |
|---|---|---|---|
| | J = 14.1 Hz), 4.26(1H, dt, J = 5.5, 12.5 Hz), 4.91(1H, dd, J = 2.4, 9.4 Hz), 7.26(1H, s), 7.31-7.40(5H, m), 8.09-8.11(1H, m), 8.86(1H, d, J = 4.7 Hz), 9.28(1H, d, J = 1.6 Hz) | | |
| A027 | (CDCl3) 2.14-2.23(1H, m), 2.25-2.35(1H, m), 2.67(3H, s), 3.42(1H, dd, J = 9.4, 14.1 Hz), 3.56(3H, s), 3.61-3.68(1H, m), 3.74(1H, dt, J = 6.3, 14.1 Hz), 3.84-3.91(1H, m), 4.07(1H, dd, J = 1.6, 14.9 Hz), 4.27(1H, dt, J = 5.5, 12.5 Hz), 5.01(1H, dd, J = 2.4, 9.4 Hz), 6.78(1H, s), 7.50(2H, d, J = 7.8 Hz), 7.87(1H, dd, J = 4.7, 6.3 Hz), 8.07(2H, d, J = 7.8 Hz), 8.51(1H, d, J = 4.7 Hz), 8.57(1H, d, J = 3.1 Hz) | 463 | |
| A028 | (CDCl3) 2.15-2.34(2H, m), 3.38(1H, dd, J = 9.4, 14.9 Hz), 3.55-3.64(4H, m), 3.74(1H, dt, J = 5.5, 14.9 Hz), 3.85-3.92(1H, m), 4.07(1H, dd, J = 1.6, 14.1 Hz), 4.26(1H, dt, J = 5.5, 13.3 Hz), 5.00(1H, dd, J = 2.4, 9.4 Hz), 7.27(1H, s), 7.54(2H, d, J = 8.6 Hz), 7.69(2H, d, J = 8.6 Hz), 8.03-8.05(1H, m), 8.87(1H, d, J = 5.5 Hz), 9.29(1H, d, J = 1.6 Hz) | 389 | |
| A029 | (CDCl3) 2.12-2.21(1H, m), 2.26-2.36(1H, m), 3.43(1H, dd, J = 8.6, 14.1 Hz), 3.53(3H, s), 3.62-3.76(2H, m), 3.83-3.90(1H, m), 4.05(1H, dd, J = 1.6, 14.1 Hz), 4.25(1H, dt, J = 5.5, 12.5 Hz), 5.01(1H, dd, J = 2.4, 9.4 Hz), 5.50-5.69(1H, brs), 5.99-6.18(1H, brs), 6.76(1H, s), 7.45(1H, t, J = 7.8 Hz), 7.52-7.55(1H, m), 7.71-7.74(1H, m), 7.87(1H, dd, J = 4.7, 6.3 Hz), 7.89-7.91(1H, m), 8.53(1H, d, J = 5.5 Hz), 8.57(1H, d, J = 3.1 Hz) | 424 | |
| A030 | (CDCl3) 2.13-2.22(1H, m), 2.26-2.36(1H, m), 2.67(3H, s), 3.49(1H, dd, J = 9.4, 14.1 Hz), 3.56(3H, s), 3.63-3.70(1H, m), 3.74(1H, dt, J = 5.5, 14.1 Hz), 3.84-3.91(1H, m), 4.11(1H, dd, J = 1.6, 14.9 Hz), 4.26(1H, dt, J = 4.7, 12.5), 5.04(1H, dd, J = 2.4, 9.4 Hz), 7.26(1H, s), 7.51(1H, t, J = 7.8 Hz), 7.55-7.58(1H, m), 8.01-8.04(1H, m), 8.12-8.15(2H, m), 8.89(1H, d, J = 5.5 Hz), 9.28(1H, d, J = 1.6 Hz) | 446 | |
| A031 | (CDCl3) 2.16-2.36(2H, m), 2.49(3H, s), 3.44(1H, dd, J = 9.4, 14.1 Hz), 3.57(3H, s), 3.60-3.67(1H, m), 3.76(1H, dt, J = 5.5, 14.1 Hz), 3.87-3.94(1H, m), 4.11(1H, dd, J = 1.6, 14.1 Hz), 4.28(1H, dt, J = 5.5, 12.5 Hz), 5.02(1H, dd, J = 2.4, 9.4 Hz), 7.28(1H, s), 7.58(2H, d, J = 8.6 Hz), 8.07(1H, dd, J = 1.6, 5.5 Hz), 8.14(2H, d, J = 8.6 Hz), 8.86(1H, d, J = 4.7 Hz), 9.29(1H, d, J = 1.6 Hz) | 446 | |
| A032 | (CDCl3) 2.12-2.21(1H, m), 2.27-2.37(1H, m), 2.48(3H, s), 3.45(1H, dd, J = 8.6, 14.1 Hz), 3.55(3H, s), 3.63-3.76(2H, m), 3.84-3.92(1H, m), 4.08(1H, dd, J = 2.4, 14.9 Hz), 4.27(1H, dt, J = 5.5, 12.5 Hz), 5.07(1H, dd, J = 2.4, 8.6 Hz), 6.76(1H, s), 7.53(1H, t, J = 7.8 Hz), 7.60(1H, dt, J = 1.6, 6.3 Hz), 7.88(1H, dd, J = 4.7, 6.3 Hz), 8.06(1H, dt, J = 1.6, 7.8 Hz), 8.19(1H, t, J = 1.6 Hz), 8.53(1H, d, J = 5.5 Hz), 8.57(1H, d, J = 3.1 Hz) | 463 | |
| A033 | (CDCl3) 2.13-2.23(1H, m), 2.28-2.38(1H, m), 3.44(1H, dd, J = 9.4, 14.9 Hz), 3.53(3H, s), 3.63-3.77(2H, m), 3.84-3.90(1H, m), 4.08(1H, d, J = 14.9 Hz), 4.26(1H, dt, J = 5.5, 12.5 Hz), 5.02(1H, dd, J = 1.6, 8.6 Hz), 5.58-5.84(1H, brs), 6.01-6.25(1H, brs), 6.61(1H, s), 7.46(1H, t, J = 7.8 Hz), 7.55(1H, d, J = 7.8 Hz), 7.73-7.78(3H, m), 7.92(1H, s), 8.72(2H, d, J = 5.5 Hz) | 406 | |
| A034 | (CDCl3) 2.16-2.35(2H, m), 2.67(3H, s), 3.44(1H, dd, J = 9.4, 14.1 Hz), 3.57(3H, s), 3.60-3.67(1H, m), 3.77(1H, dt, J = 5.5, 14.1 Hz), 3.87-3.93(1H, m), 4.10(1H, dd, J = 1.6, 14.1 Hz), 4.28(1H, dt, J = 4.7, 12.5 Hz), 4.99(1H, dd, J = 2.4, 9.4 Hz), 7.27(1H, s), 7.53(2H, d, J = 8.6 Hz), 8.07-8.10(3H, m), 8.86(1H, d, J = 5.5 Hz), 9.29(1H, d, J = 1.6 Hz) | 446 | |
| A035 | (CDCl3) 2.14-2.34 (3H, m), 3.40 (1H, dd, J = 12.4, 19.2 Hz), 3.55 (3H, s), 3.60-3.90 (3H, m), 4.04 (1H, d, J = 18.4 Hz), 4.22-4.26 (1H, m), 4.93 (1H, dd, J = 2.4, 12.4 Hz), .6.62 (1H, s), 7.04-7.10 (2H, m), 7.34-7.39 (2H, m), 7.77 (2H, dd, J = 2.0, 6.0 Hz), 8.71 (2H, dd, J = 1.6, 6.0 Hz) | 381 | |
| A036 | (CDCl3) 2.15-2.24(1H, m), 2.26-2.36(1H, m), 2.49(3H, s), 3.43(1H, dd, J = 9.4, 14.1 Hz), 3.56(3H, s), 3.62-3.69(1H, m), 3.76(1H, dt, J = 6.3, 14.1 Hz), 3.86-3.93(1H, m), 4.12(1H, dd, J = 1.6, 14.9 Hz), 4.28(1H, dt, J = 4.7, 12.5 Hz), 5.06(1H, dd, J = 2.4, 9.4 Hz), 6.62(1H, s), 7.57(2H, d, J = 8.6 Hz), 7.76-7.77(2H, m), 8.13(2H, d, J = 8.6 Hz), 8.71-8.72(2H, m) | 445 | |
| A037 | (CDCl3) 2.13-2.23(1H, m), 2.24-2.34(1H, m), 3.37(1H, dd, J = 9.4, 14.9 Hz), 3.55(3H, s), 3.60-3.66(1H, m), 3.74(1H, dt, J = 6.3, 14.9 Hz), 3.83-3.90(1H, m), 4.09(1H, d, J = 14.1 Hz), 4.26(1H, dt, J = 5.5, 12.5 Hz), 5.05(1H, dd, J = 2.4, 8.6 Hz), 6.63(1H, s), 7.53(2H, d, J = 8.6 Hz), 7.68(2H, d, J = 8.6 Hz), 7.75(2H, d, J = 5.5 Hz), 8.73(2H, d, J = 5.5 Hz) | 388 | |
| A038 | (CDCl3) 2.12-2.22(1H, m), 2.27-2.37(1H, m), 3.40(1H, dd, J = 8.6, 14.1 Hz), 3.53(3H, s), 3.62-3.74(2H, m), 3.84-3.90(1H, m), 4.05(1H, dd, J = 1.6, 14.9 Hz), 4.26(1H, dt, J = 5.5, 13.3 Hz), 5.01(1H, dd, J = 2.4, 8.6 Hz), 5.51-5.67(1H, brs), 6.00-6.16(1H, brs), 6.76(1H, s), 7.47(2H, d, J = 8.6 Hz), 7.81(2H, d, J = 8.6 Hz), 7.85(1H, dd, J = 5.5, 7.0 Hz), 8.51(1H, d, J = 4.7 Hz), 8.57(1H, d, J = 3.1 Hz) | 424 | |
| A039 | (CDCl3) 2.15-2.24(1H, m), 2.25-2.36(1H, m), 3.39(1H, dd, J = 9.4, 14.9 Hz), 3.56(3H, s), 3.58-3.65(1H, m), 3.73(1H, dt, J = 5.5, 14.9 Hz), 3.85-3.92(1H, m), 4.08(1H, dd, J = 1.6, 14.1 Hz), 4.26(1H, dt, J = 5.5, 12.5 Hz), 4.98(1H, dd, J = 2.4, 9.4 Hz), 7.27(1H, s), 7.50(1H, t, J = 7.8 Hz), 7.61-7.65(2H, m), 7.76-7.78(1H, m), 8.05(1H, dd, J = 1.6, 4.7 Hz), 8.88(1H, d, J = 5.5 Hz), 9.30(1H, s) | 389 | |
| A040 | (CDCl3) 2.14-2.23(1H, m), 2.25-2.36(1H, m), 3.44(1H, dd, J = 9.4, 14.1 Hz), 3.54(3H, s), 3.63-3.81(2H, m), 3.83-3.90(1H, m), 4.07(1H, d, J = 14.1 | 363 | |

TABLE 2-continued

| Comp No. | ¹H-NMR (solvent) δ: | [M + H] | [alpha]D |
|---|---|---|---|
| | Hz), 4.25(1H, dt, J = 4.7, 12.5 Hz), 4.94(1H, dd, J = 2.4, 9.4 Hz), 6.62(1H, s), 7.30-7.40(5H, m), 7.77-7.79(2H, m), 8.70-8.72(2H, m) | | |
| A041 | (CDCl3) 1.24(3H, d, J = 6.3 Hz), 2.02-2.20(2H, m), 3.18(1H, dd, J = 9.4, 14.1 Hz), 3.48-3.55(4H, m), 3.65-3.74(2H, m), 3.80(1H, d, J = 14.1 Hz), 3.92-4.00(1H, m), 4.09(1H, dt, J = 5.5, 12.5 Hz), 6.77(1H, s), 7.91(1H, dd, J = 4.7, 6.3 Hz), 8.52(1H, d, J = 4.7 Hz), 8.55(1H, d, J = 2.4 Hz) | 319 | |
| A042 | (CDCl3) 2.13-2.22(1H, m), 2.27-2.36(1H, m), 2.66(3H, s), 3.48(1H, dd, J = 9.4, 14.9 Hz), 3.55(3H, s), 3.64-3.78(2H, m), 3.84-3.90(1H, m), 4.11(1H, dd, J = 1.6, 14.1 Hz), 4.26(1H, dt, J = 4.7, 12.5 Hz), 5.06(1H, dd, J = 2.4, 9.4 Hz), 6.61(1H, s), 7.50(1H, t, J = 7.8 Hz), 7.55(1H, dt, J = 1.6, 7.8 Hz), 7.78-7.80(2H, m), 8.01-8.04(1H, m), 8.14-8.15(1H, m), 8.72-8.73(2H, m) | 445 | |
| A043 | (CDCl3) 2.12-2.22(1H, m), 2.24-2.35(1H, m), 3.42(1H, dd, J = 9.4, 14.9 Hz) 3.56(3H, s), 3.59-3.67(1H, m), 3.73(1H, dt, J = 5.5, 14.1 Hz), 3.82-3.89(1H, m), 4.05(1H, d, J = 14.9 Hz), 4.24(1H, dt, J = 5.5, 12.5 Hz), 4.91(1H, dd, J = 2.4 Hz), 7.24-7.28(2H, m), 7.30-7.33(1H, m), 7.45-7.47(1H, m), 7.60-7.61(1H, m), 8.07-8.09(1H, m), 8.88(1H, d, J = 5.5 Hz), 9.29(1H, d, J = 1.6 Hz) | 442 | |
| A044 | (CDCl3) 2.12-2.21(1H, m), 2.22-2.32(1H, m), 3.35(1H, dd, J = 9.4, 14.9 Hz), 3.54(3H, s), 3.58-3.65(1H, m), 3.72(1H, dt, J = 5.5, 14.9 Hz), 3.81-3.87(1H, m), 4.01(1H, dd, J = 2.4, 14.1 Hz), 4.23(1H, dt, J = 5.5, 12.5 Hz), 4.90(1H, dd, J = 1.6, 9.4 Hz), 6.77(1H, s), 7.26(2H, d, J = 8.6 Hz), 7.50(2H, d, J = 8.6 Hz), 7.84(1H, dd, J = 4.7, 6.3 Hz), 8.51(1H, d, J = 4.7 Hz), 8.57(1H, d, J = 3.1 Hz) | 459 | |
| A045 | (CDCl3) 2.14-2.24(1H, m), 2.27-2.38(1H, m), 2.49(3H, s), 3.48(1H, dd, J = 9.4, 14.9 Hz), 3.56(3H, s), 3.63-3.69(1H, m), 3.74(1H, dt, J = 6.3, 14.1 Hz), 3.86-3.93(1H, m), 4.11(1H, dd, J = 1.6, 14.9 Hz), 4.27(1H, dt, J = 5.5, 12.5 Hz), 5.06(1H, dd, J = 2.4, 9.4 Hz), 7.27(1H, s), 7.56(1H, t, J = 7.8 Hz), 7.64(1H, dt, J = 1.6, 7.8 Hz), 8.08(1H, dt, J = 1.6, 7.8 Hz), 8.11(1H, dd, J = 1.6, 5.5 Hz), 8.22(1H, t, J = 1.6 Hz), 8.89(1H, d, J = 4.7 Hz), 9.29(1H, d, J = 1.6 Hz) | 446 | |
| A046 | (CDCl3) 2.13-2.23(1H, m), 2.26-2.36(1H, m), 3.39(1H, dd, J = 8.6, 14.1 Hz), 3.54(3H, s), 3.61-3.76(2H, m), 3.84-3.90(1H, m), 4.08(1H, dd, J = 1.6, 14.9 Hz), 4.26(1H, dt, J = 5.5, 12.5 Hz), 5.02(1H, dd, J = 2.4, 8.6 Hz), 6.62(1H, s), 7.48(1H, t, J = 7.8 Hz), 7.60-7.63(2H, m), 7.74-7.77(3H, m), 8.73(2H, dd, J = 1.6, 3.9 Hz) | 388 | |
| A047 | (CDCl3) 2.12-2.21(1H, m), 2.24-2.35(1H, m), 3.36(1H, dd, J = 8.6, 14.1 Hz), 3.55(3H, s), 3.60-3.74(2H, m), 3.83-3.89(1H, m), 4.05(1H, dd, J = 1.6, 14.1 Hz), 4.25(1H, dt, J = 4.7, 12.5 Hz), 5.01(1H, dd, J = 2.4, 8.6 Hz), 6.76(1H, s), 7.47(1H, t, J = 7.8 Hz), 7.58-7.62(2H, m), 7.74-7.75(1H, m), 7.82(1H, dd, J = 4.7, 6.3 Hz), 8.53(1H, d, J = 5.5 Hz), 8.58(1H, d, J = 3.1 Hz) | 406 | |
| A048 | (CDCl3) 2.13-2.23(1H, m), 2.28-2.38(1H, m), 3.44(1H, dd, J = 9.4, 14.9 Hz), 3.53(3H, s), 3.63-3.77(2H, m), 3.84-3.90(1H, m), 4.09(1H, dd, J = 1.6, 14.1 Hz), 4.26(1H, dt, J = 5.5, 12.5 Hz), 5.02(1H, dd, J = 2.4, 9.4 Hz), 5.52-5.70(1H, brs), 6.02-6.16(1H, brs), 6.61(1H, s), 7.46(1H, t, J = 7.8 Hz), 7.55(1H, d, J = 7.8 Hz), 7.72-7.75(1H, m), 7.76-7.78(2H, m), 7.91-7.92(1H, m), 8.72-8.73(2H, m) | 446 | |
| A049 | (CDCl3) 2.14-2.23(1H, m), 2.27-2.37(1H, m), 3.46(1H, dd, J = 9.4, 14.7 Hz), 3.55(3H, s), 3.62-3.68(1H, m), 3.74(1H, dt, J = 5.5, 14.1 Hz), 3.85-3.92(1H, m), 4.08(1H, dd, J = 1.6, 14.1 Hz), 4.26(1H, dt, J = 5.5, 12.5 Hz), 5.00(1H, dd, J = 2.4, 9.4 Hz), 5.55-5.72(1H, brs), 6.05-6.22(1H, brs), 7.26(1H, s), 7.47(1H, t, J = 7.8 Hz), 7.57(1H, d, J = 7.8 Hz), 7.73(1H, dt, J = 1.6, 7.8 Hz), 7.94(1H, t, J = 1.6 Hz), 8.10(1H, dt, J = 1.6, 5.5 Hz), 8.89(1H, d, J = 5.5 Hz), 9.28(1H, d, J = 1.6 Hz) | 407 | |
| A050 | (DMSO-d6) 2.12-2.20(1H, m), 2.27-2.33(1H, m), 3.44(3H, s), 3.69(1H, ddd, J = 3.0, 9.2, 14.2 Hz), 3.76(2H, t, J = 6..0 Hz), 3.83-3.87(1H, m), 3.92-3.97(1H, m), 4.09(1H, dt, J = 3.6, 13.2 Hz), 4.77(1H, dd, J = 3.1, 9.8 Hz), 6.91(1H, s), 7.13-7.18(2H, m), 7.39-7.42(2H, m), 8.22-8.23(1H, m), 9.00(1H, d, J = 5.0 Hz), 9.29(1H, s) | 382 | |
| A051 | (CDCl3) 1.26(3H, d, J = 6.3 Hz), 2.03-2.21(2H, m), 3.20(1H, dd, J = 8.6, 14.1 Hz), 3.49-3.56(4H, m), 3.67-3.75(2H, m), 3.82(1H, dd, J = 1.6, 14.1 Hz), 3.94-4.02(1H, m), 4.10(1H, dt, J = 5.5, 12.5 Hz), 7.25(1H, s), 8.11(1H, dd, J = 1.6, 5.5 Hz), 8.88(1H, d, J = 5.5 Hz), 9.28(1H, d, J = 1.6 Hz) | 302 | |
| A052 | (CDCl3) 2.14-2.23(1H, m), 2.25-2.35(1H, m), 2.67(3H, s), 3.42(1H, dd, J = 9.4, 14.1 Hz), 3.56(3H, s), 3.61-3.68(1H, m), 3.74(1H, dt, J = 6.3, 14.1 Hz), 3.84-3.91(1H, m), 4.07(1H, dd, J = 1.6, 14.9 Hz), 4.27(1H, dt, J = 5.5, 12.5 Hz), 5.01(1H, dd, J = 2.4, 9.4 Hz), 6.78(1H, s), 7.50(2H, d, J = 7.8 Hz), 7.87(1H, dd, J = 4.7, 6.3 Hz), 8.07(2H, d, J = 7.8 Hz), 8.51(1H, d, J = 4.7 Hz), 8.57(1H, d, J = 3.1 Hz) | 463 | |
| A053 | (CDCl3) 2.13-2.23(1H, m), 2.25-2.35(1H, m), 2.48(3H, s), 3.41(1H, dd, J = 9.4, 14.9 Hz), 3.56(3H, s), 3.61-3.68(1H, m), 3.74(1H, dt, J = 5.5, 14.1 Hz), 3.85-3.92(1H, m), 4.08(1H, dd, J = 1.6, 14.9 Hz), 4.27(1H, dt, J = 5.5, 12.5 Hz), 5.04(1H, dd, J = 2.4, 9.4 Hz), 6.77(1H, s), 7.55(2H, d, J = 8.6 Hz), 7.85(1H, dd, J = 4.7, 6.3 Hz), 8.12(2H, d, J = 8.6 Hz), 8.51(1H, d, J = 4.7 Hz), 8.58(1H, d, J = 3.1 Hz) | 463 | |
| A054 | (CDCl3) 2.12-2.22(1H, m), 2.23-2.33(1H, m), 3.38(1H, dd, J = 9.4, 14.9 Hz), 3.54(3H, s), 3.60-3.67(1H, m), 3.74(1H, dt, J = 5.5, 14.1 Hz), 3.81-3.88(1H, m), 4.00(1H, d, J = 14.1 Hz), 4.24(1H, dt, J = 5.5, 12.5 Hz), 4.91(1H, dd, J = 2.4, 9.4 Hz), 6.77(1H, s), 7.06(2H, t, J = 8.6 Hz), 7.35(2H, | 399 | |

TABLE 2-continued

| Comp No. | ¹H-NMR (solvent) δ: | [M + H] | [alpha]D |
|---|---|---|---|
| | dd, J = 5.5, 8.6 Hz), 7.86(1H, dd, J = 4.7, 6.3 Hz), 8.50(1H, d, J = 4.7 Hz), 8.56(1H, d, J = 3.1 Hz) | | |
| A055 | (CDCl3) 2.11-2.21(1H, m), 2.25-2.36(1H, m), 2.66(3H, s), 3.47(1H, dd, J = 8.6, 14.1 Hz), 3.55(3H, s), 3.63-3.76(2H, m), 3.83-3.90(1H, m), 4.07(1H, dd, J = 1.6, 12.5 Hz), 4.26(1H, dt, J = 4.7, 12.5 Hz), 5.04(1H, dd, J = 2.4, 9.4 Hz), 6.77(1H, s), 7.49(1H, t, J = 7.8 Hz), 7.53(1H, dt, J = 1.6, 7.8 Hz), 7.91(1H, dd, J = 4.7, 6.3 Hz), 8.00-8.03(1H, m), 8.11-8.12(1H, m), 8.53(1H, d, J = 5.5 Hz), 8.56(1H, d, J = 3.3 Hz) | 463 | |
| A056 | (CDCl3) 2.13-2.23(1H, m), 2.28-2.38(1H, m), 2.48(3H, s), 3.47(1H, dd, J = 8.6, 14.1 Hz), 3.55(3H, s), 3.64-3.77(2H, m), 3.85-3.91(1H, m), 4.12(1H, dd, J = 2.4, 14.1 Hz), 4.27(1H, dt, J = 4.7, 12.5 Hz), 5.08(1H, dd, J = 2.4, 8.6 Hz), 6.61(1H, s), 7.54(1H, t, J = 7.8 Hz), 7.62(1H, dt, J = 1.6, 7.8 Hz), 7.77-7.78(2H, m), 8.06(1H, dt, J = 1.6, 7.8 Hz), 8.21(1H, t, J = 1.6 Hz), 8.72-8.74(2H, m) | 445 | |
| A057 | (CDCl3) 2.13-2.23(1H, m), 2.24-2.34(1H, m), 3.40(1H, dd, J = 9.4, 14.9 Hz), 3.54(3H, s), 3.61-3.68 (1H, m), 3.76(1H, dt, J = 5.5, 14.9 Hz), 3.82-3.89(1H, m), 4.04(1H, d, J = 14.1 Hz), 4.24(1H, dt, J = 5.5, 12.5 Hz), 4.93(1H, dd, J = 1.6, 9.4 Hz), 6.62(1H, s), 7.07(2H, t, J = 8.6 Hz), 7.37(2H, dd, J = 5.5, 8.6 Hz), 7.76(2H, d, J = 5.5 Hz), 8.72(2H, d, J = 5.5 Hz) | 381 | |
| A058 | (CDCl3) 2.14-2.34(2H, m), 3.38(1H, dd, J = 9.4, 14.1 Hz), 3.56(3H, s), 3.57-3.64(1H, m), 3.75(1H, dt, J = 5.5, 14.1 Hz), 3.83-3.90(1H, m), 4.04(1H, dd, J = 1.6, 14.1 Hz), 4.24(1H, dt, J = 5.5, 12.5 Hz), 4.88(1H, dd, J = 2.4, 9.4 Hz), 7.27-7.30(3H, m), 7.52(2H, d, J = 8.6 Hz), 8.06(1H, dd, J = 1.6, 5.5 Hz), 8.86(1H, d, J = 5.5 Hz), 9.29(1H, d, J = 1.6 Hz) | 442 | |
| A059 | (CDCl3) 2.12-2.21(1H, m), 2.27-2.37(1H, m), 2.48(3H, s), 3.45(1H, dd, J = 9.4, 14.9 Hz), 3.55(3H, s), 3.63-3.76(2H, m), 3.84-3.92(1H, m), 4.08(1H, dd, J = 2.4, 14.9 Hz), 4.27(1H, dt, J = 5.5, 12.5 Hz), 5.07(1H, dd, J = 2.4, 8.6 Hz), 6.76(1H, s), 7.53(1H, t, J = 7.8 Hz), 7.60(1H, dt, J = 1.6, 6.3 Hz), 7.88(1H, dd, J = 4.7, 6.3 Hz), 8.06(1H, dt, J = 1.6, 7.8 Hz), 8.19(1H, t, J = 1.6 Hz), 8.53(1H, d, J = 5.5 Hz), 8.57(1H, d, J = 3.1 Hz) | 463 | |
| A060 | (CDCl3) 2.15-2.24(1H, m), 2.29-2.39(1H, m), 3.44(1H, dd, J = 8.6, 14.1 Hz), 3.53(3H, s), 3.61-3.68(1H, m), 3.73(1H, dt, J = 5.5, 14.9 Hz), 3.87-3.93(1H, m), 4.07(1H, dd, J = 1.6, 14.9 Hz), 4.27(1H, dt, J = 5.5, 12.5 Hz), 4.99(1H, dd, J = 2.4, 9.4 Hz), 5.50-5.69(1H, brs), 6.02-6.19(1H, brs), 7.27(1H, s), 7.49(2H, d, J = 8.6 Hz), 7.83(2H, d, J = 8.6 Hz), 8.06-8.08(1H, m), 8.87(1H, d, J = 4.7 Hz), 9.29(1H, d, J = 1.6 Hz) | 407 | |
| A061 | (CDCl3) 1.26(3H, d, J = 6.3 Hz), 2.03-2.21(2H, m), 3.19(1H, dd, J = 9.4, 14.9 Hz), 3.50-3.57(4H, m), 3.67-3.74(2H, m), 3.84(1H, dt, J = 1.6, 14.1 Hz), 3.94-4.02(1H, m), 4.09(1H, dt, J = 4.7, 12.5 Hz), 6.61(1H, s), 7.77-7.79(2H, m), 8.71-8.72(2H,,m) | 301 | |
| A062 | (CDCl3) 2.13-2.23(1H, m), 2.28-2.38(1H, m), 3.42(1H, dd, J = 9.4, 14.9 Hz), 3.53(3H, s), 3.63-3.77(2H, m), 3.85-3.91(1H, m), 4.08(1H, dd, J = 2.4, 14.9 Hz), 4.27(1H, dt, J = 4.7, 12.5 Hz), 5.03(1H, dd, J = 2.4, 9.4 Hz), 5.52-5.71(1H, brs), 6.02-6.19(1H, brs), 6.61(1H, s), 7.49(2H, d, J = 8.6 Hz), 7.76-7.77(2H, m), 7.82(2H, d, J = 8.6 Hz), 8.71-8.73(2H, m) | 406 | |
| A063 | (CDCl3) 2.12-2.21(1H, m), 2.23-2.33(1H, m), 3.34(1H, dd, J = 9.4, 14.9 Hz), 3.55(3H, s), 3.59-3.66(1H, m), 3.72(1H, dt, J = 5.5, 14.9 Hz), 3.82-3.89(1H, m), 4.05(1H, dd, J = 1.6, 14.1 Hz), 4.25(1H, dt, J = 4.7, 12.5 Hz), 5.04(1H, dd, J = 2.4, 9.4 Hz), 6.76(1H, s), 7.51(2H, d, J = 7.8 Hz), 7.66(2H, d, J = 7.8 Hz), 7.81(1H, dd, J = 5.5, 7.0 Hz), 8.51(1H, d, J = 4.7 Hz), 8.58(1H, d, J = 3.1 Hz) | 406 | |
| A064 | (DMSO-d6) 1.20 (3H, d, J = 1.2 Hz), 1.86-1.92 (1H, m), 1.99-2.05 (1H, m), 3.42 (3H, s), 3.47 (1H, ddd, J = 2.6, 9.0, 14.9 Hz), 3.63-3.76 (4H, m), 3.89 (1H, dd, J = 2.9, 13.2 Hz), 4.22-4.25 (1H, m), 6.92 (1H, s), 8.19 (1H, dd, J = 1.3, 5.1 Hz), 9.01 (1H, d, J = 5.1 Hz), 9.30 (1H, d, J = 1.2 Hz) | 302 | |
| A065 | (DMSO-d6) 1.81-2.21 (5H, m), 3.47 (7H, s), 3.67-3.87 (9H, m), 4.00 (5H, d, J = 4.7 Hz), 5.44 (2H, t, J = 4.7 Hz), 6.86 (2H, s), 7.07-7.20 (2H, m), 7.26 (5H, t, J = 7.4 Hz), 7.38-7.53 (5H, m), 8.19 (2H, dd, J = 1.2, 5.1 Hz), 9.01 (2H, d, J = 5.1 Hz), 9.25 (2H, d, J = 1.2 Hz) | 364 | |
| A066 | (DMSO-d6) 2.14 (1 H, d, J = 6.3 Hz), 2.21-2.39 (1 H, m), 3.43 (3 H, s), 3.57-3.87 (4 H, m), 3.87-4.00 (1 H, m), 4.00-4.16 (1 H, m), 4.75 (1 H, d, J = 7.0 Hz), 6.49 (1 H, s), 7.14-7.48 (5 H, m), 7.99 (1 H, t, J = 5.9 Hz), 8.56 (1 H, d, J = 4.7 Hz), 8.69 (1 H, br. s.) | 381 | |
| A067 | (DMSO-d6) 1.20 (3 H, d), 1.88 (1 H, qd, J = 7.7, 4.3 Hz), 2.11-2.26 (1 H, m), 3.40 (3 H, s), 3.43-3.56 (1 H, m), 3.56-3.77 (4 H, m), 3.78-3.93 (1 H, m), 4.17-4.34 (1 H, m), 6.53 (1 H, s), 7.85-8.00 (1 H, m), 8.57 (1 H, d, J = 4.7 Hz), 8.70 (1 H, d, J = 3.1 Hz) | 319 | |
| A068 | (DMSO-d6) 1.18 (3H, d, J = 6.6 Hz), 1.84-1.89 (1H, m), 1.96-2.03 (1H, m), 3.41 (3H, s), 3.44 (1H, ddd, J = 2.7, 9.0, 14.9 Hz), 3.59-3.75 (4H, m), 3.86 (1H, dd, J = 2.9, 13.2 Hz), 4.16-4.20 (1H, m), 6.51 (1H, d, J = 1.2 Hz), 7.95 (1H, dd, J = 5.0, 6.8 Hz), 8.57 (1H, dd, J = 0.8, 5.0 Hz), 8.70 (1H, d, J = 3.2 Hz) | 319 | |
| A069 | (DMSO-d6) 1.83-2.21 (2H, m), 3.46 (3H, s), 3.65-3.86 (4H, m), 3.90-4.07 (2H, m), 5.37 (1H, t, J = 4.9 Hz), 6.46 (1H, d, J = 1.2 Hz), 7.12-7.23 (1H, m), 7.28 (2H, t, J = 7.6 Hz), 7.38-7.48 (2H, m), 7.85 (1H, dd, J = 5.1, 7.0 Hz), 8.57 (1H, dd, J = 0.8, 5.1 Hz), 8.67 (1H, d, J = 3.1 Hz) | 381 | |
| A070 | (DMSO-d6) 1.22(3H, d, J = 6.7 Hz), 1.88-1.96(1H, m), 2.18-2.25(1H, m), 3.41(3H, s), 3.48-3.54(1H, m), 3.62-3.75(4H, m), 3.82-3.88(1H, m), 4.28- | 302 | |

TABLE 2-continued

| Comp No. | ¹H-NMR (solvent) δ: | [M + H] | [alpha]D |
|---|---|---|---|
| | 4.32(1H, m), 6.95(1H, s), 8.19-8.20(1H, m), 9.01(1H, d, J = 5.0 Hz), 9.30(1H, d, J = 1.2 Hz) | | |
| A071 | (DMSO-d6) 2.13-2.21(1H, m), 2.27-2.33(1H, m), 3.45(3H, s), 3.69(1H, ddd, J = 2.9, 9.1, 12.5 Hz), 3.77(2H, t, J = 6.0 Hz), 3.84-3.87(1H, m), 3.92-3.98(1H, m), 4.10(1H, dt, J = 3.4, 13.3 Hz), 4.76(1H, dd, J = 0.8, 9.8 Hz), 6.91(1H, s), 7.23-7.27(1H, m), 7.31-7.38(4H, m), 8.22-8.23(1H, m), 9.00(1H, d, J = 5.0 Hz), 9.29(1H, s) | 364 | |
| A072 | (DMSO-d6) 0.81-0.97 (3 H, m), 1.34-1.55 (2 H, m), 1.74-1.90(1 H, m), 1.97-2.10 (1 H, m), 3.38-3.44 (3 H, m), 3.46-3.58 (2 H, m), 3.63 (2 H, br. s.), 3.68-3.81 (2 H, m), 3.92-4.04 (1 H, m), 6.89 (1 H, s), 8.21 (1 H, d, J = 6.3 Hz), 9.00 (1 H, d, J = 4.7 Hz), 9.29 (1 H, s) | 333 | |
| A073 | (DMSO-d6) 0.89(3H, t, J = 7.3 Hz), 1.41-1.49(2H, m), 1.79-1.85(1H, m), 1.98-2.05(1H, m), 3.39(3H, s), 3.44-3.52(2H, m), 3.58-3.61(2H, m), 3.69-3.74(2H, m), 3.95(1H, dt, J = 3.3, 12.6 Hz), 6.47(1H, d, J = 1.0 Hz), 7.97(1H, dd, J = 5.3, 6.6 Hz), 8.57(1H, d, J = 4.7 Hz), 8.70(1H, d, J = 3.1 Hz) | 316 | |
| A074 | (CDCl3) 3.44-3.51(1H, m), 3.55(3H, s), 3.56-3.65(2H, m), 3.82(1H, dt, J = 3.1, 14.1 Hz), 3.92-4.13(5H, m), 7.16(2H, d, J = 8.6 Hz), 7.27(1H, s), 7.48(2H, d, J = 8.6 Hz), 8.04(1H, dd, J = 1.6, 4.7 Hz), 8.84(1H, d, J = 4.7 Hz), 9.28(1H, s) | 442 | |
| A075 | (CDCl3) 3.47-3.55(4H, m), 3.58-3.72(2H, m), 3.83(1H, dt, J = 3.9, 14.1 Hz), 3.94-4.01(2H, m), 4.05-4.11(3H, m), 7.24-7.27(3H, m), 7.29-7.31(1H, m), 7.34-7.38(2H, m), 8.06(1H, dd, J = 1.6, 5.5 Hz), 8.83(1H, d, J = 5.5 Hz), 9.27(1H, d, J = 1.6 Hz) | 364 | |
| A076 | (CDCl3) 3.51-3.65(6H, m), 3.84(1H, dt, J = 3.9, 14.9 Hz), 4.00-4.09(4H, m), 4.14(1H, dt, J = 3.9, 13.3 Hz), 7.29(1H, s), 7.42(2H, d, J = 8.6 Hz), 7.66(2H, d, J = 8.6 Hz), 8.02(1H, d, J = 5.5 Hz), 8.85(1H, d, J = 5.5 Hz), 9.29(1H, s) | 389 | |
| A077 | (DMSO-d6) 2.42 (3H, s), 3.43 (3H, s), 3.63 (1H, m), 3.70-3.85 (3H, m), 3.89-4.09 (5H, m), 6.48 (1H, d, J = 1.2 Hz), 7.61 (2H, d, J = 8.2 Hz), 7.91 (1H, dd, J = 5.1, 7.0 Hz), 8.06 (2H, d, J = 8.6 Hz), 8.54 (1H, dd, J = 0.8, 5.1 Hz), 8.69 (1H, d, J = 3.1 Hz) | 463 | |
| A078 | (DMSO-d6) 3.43 (3H, s), 3.58-4.06 (9H, m), 7.56 (2H, d, J = 8.6 Hz), 6.48 (1H, d, J = 1.2 Hz), 7.92 (1H, dd, J = 5.1, 7.0 Hz), 8.01 (2H, d, J = 8.6 Hz), 8.53 (1H, d, J = 5.1 Hz), 8.70 (1H, d, J = 3.1 Hz), 9.71 (1H, s) | 449 | |
| A079 | (CDCl3) 2.12-2.22(1H, m), 2.24-2.35(1H, m), 3.41(1H, dd, J = 9.4, 14.9 Hz) 3.56(3H, s), 3.59-3.66(1H, m), 3.73(1H, dt, J = 5.5, 14.1 Hz), 3.82-3.89(1H, m), 4.05(1H, d, J = 14.9 Hz), 4.24(1H, dt, J = 5.5, 12.5 Hz), 4.91(1H, dd, J = 2.4 Hz), 7.24-7.28(2H, m), 7.30-7.33(1H, m), 7.45-7.47(1H, m), 7.60-7.61(1H, m), 8.07-8.09(1H, m), 8.88(1H, d, J = 5.5 Hz), 9.29(1H, d, J = 1.6 Hz) | 442 | |
| A080 | (DMSO-d6) 3.44 (3H, s), 3.66 (1H, m), 3.73-3.89 (3H, m), 3.92-4.11 (5H, m), 6.90 (1H, s), 7.67 (2H, d, J = 8.6 Hz), 8.07-8.18 (3H, m), 8.98 (1H, d, J = 5.1 Hz), 9.11 (1H, s), 9.29 (1H, d, J = 1.2 Hz) | 432 | |
| A081 | (DMSO-d6) 2.42 (3H, s), 3.44 (3H, s), 3.62-3.68 (1H, m), 3.70-3.87 (3H, m), 3.91-4.12 (5H, m), 6.90 (1H, s), 7.65 (2H, d, J = 8.2 Hz), 8.08 (2H, d, J = 8.2 Hz), 8.11 (1H, dd, J = 1.2, 5.1 Hz), 8.97 (1H, d, J = 5.1 Hz), 9.29 (1H, d, J = 1.2 Hz) | 446 | |
| A082 | (DMSO-d6) 3.44 (3H, s), 3.55-4.14 (9H, m), 6.90 (1H, s), 7.60 (2H, d, J = 8.2 Hz), 8.03 (2H, d, J = 8.2 Hz), 8.12 (1H, dd, J = 1.4, 5.3 Hz), 8.97 (1H, d, J = 5.5 Hz), 9.29 (1H, d, J = 1.2 Hz), 9.71 (1H, s) | 432 | |
| A083 | (DMSO-d6) 2.66 (3H, s), 3.43 (3H, s), 3.57-3.85 (4H, m), 3.86-4.07 (5H, m), 6.48 (1H, d, J = 1.2 Hz), 7.54 (2H, d, J = 8.6 Hz), 7.92 (1H, dd, J = 4.9, 6.8 Hz), 7.96 (2H, d, J = 8.2 Hz), 8.53 (1H, dd, J = 0.8, 5.1 Hz), 8.69 (1H, d, J = 3.1 Hz) | 463 | |
| A084 | (CDCl3) 0.96(3H, d, J = 7.0 Hz), 2.36-2.45(1H, m), 3.22(1H, dd, J = 9.4, 14.1 Hz), 3.45-3.53(5H, m), 3.66(1H, dd, J = 4.7, 14.1 Hz), 3.74(1H, dt, J = 3.9, 14.1 Hz), 3.88-3.96(3H, m), 6.78(1H, s), 7.92(1H, dd, J = 4.7, 6.3 Hz), 8.52(1H, d, J = 4.7 Hz), 8.55(1H, d, J = 3.1 Hz) | 319 | |
| A085 | (CDCl3) 2.67(3H, s), 3.55-3.63(5H, m), 3.70(1H, dd, J = 10.2, 14.1 Hz), 3.84(1H, dt, J = 3.1, 14.1 Hz), 3.93-4.16(5H, m), 7.28(1H, s), 7.40(2H, d, J = 7.8 Hz), 8.04-8.07(3H, m), 8.83(1H, d, J = 5.5 Hz), 9.28(1H, d, J = 1.6 Hz) | 446 | |
| A086 | (DMSO-d6) 2.67 (3H, s), 3.44 (3H, s), 3.59-4.09 (9H, m), 6.90 (1H, s), 7.58 (2H, d, J = 8.6 Hz), 7.98 (2H, d, J = 8.2 Hz), 8.12 (1H, dd, J = 1.4, 5.3 Hz), 8.97 (1H, d, J = 5.5 Hz), 9.29 (1H, d, J = 1.2 Hz) | 446 | |
| A087 | (CDCl3) 0.97(3H, d, J = 7.0 Hz), 2.36-2.47(1H, m), 3.24(1H, dd, J = 9.4, 14.1 Hz), 3.45-3.55(5H, m), 3.68(1H, dd, J = 3.9, 14.1 Hz), 3.76(1H, dt, J = 4.7, 14.1 Hz), 3.91(1H, dd, J = 4.7, 12.5 Hz), 3.95-3.97(2H, m), 7.25(1H, s), 8.12(1H, dd, J = 1.6, 5.5 Hz), 8.87(1H, d, J = 4.7 Hz), 9.28(1H, d, J = 1.6 Hz) | 302 | |
| A088 | (CDCl3) 0.97(3H, d, J = 7.0 Hz), 2.38-2.48(1H, m), 3.24(1H, dd, J = 9.4, 14.1 Hz), 3.45-3.56(5H, m), 3.69(1H, dd, J = 3.9, 14.1 Hz), 3.77(1H, dt, J = 4.7, 14.1 Hz), 3.91(1H, dd, J = 4.7, 12.5 Hz), 3.94-3.98(2H, m), 6.61(1H, s), 7.78-7.79(2H, m), 8.71-8.72(2H, m) | 301 | |
| A089 | (DMSO-d6) 2.10-2.19(1H, m), 2.32-2.37(1H, m), 3.45(3H, s), 3.67(1H, ddd, J = 3.2, 9.4, 14.2 Hz), 3.72-3.77(2H, m), 3.80-3.86(1H, m), 3.98(1H, ddd, J = 2.5, 9.5, 13.2 Hz), 4.12(1H, dt, J = 3.5, 13.2 Hz), 4.87(1H, dd, J = 3.2, 9.8 Hz), 6.50(1H, d, J = 1.1 Hz), 7.58(2H, d, J = 8.3 Hz), 8.02(2H, d, J = 8.4 Hz), 8.57(1H, dd, J = 0.6, 5.0 Hz), 8.70(1H, d, J = 3.1 Hz), 9.71(1H, s) | 449 | +10.98 (c = 0.225, CH2Cl2) |
| A090 | (DMSO-d6) 2.09-2.18(1H, m), 2.33-2.39(1H, m), 2.41(3H, s), 3.44(3H, s), 3.67(1H, ddd, J = 3.3, 9.3, 14.2 Hz), 3.73-3.77(2H, m), 3.82-3.86(1H, m), | 463 | +9.43 (c = 0.420, CH2Cl2) |

TABLE 2-continued

| Comp No. | ¹H-NMR (solvent) δ: | [M + H] | [alpha]D |
|---|---|---|---|
|  | 3.98(1H, ddd, J = 2.2, 9.4, 13.2 Hz), 4.12(1H, dt, J = 3.2, 13.5 Hz), 4.90(1H, dd, J = 3.2, 9.9 Hz), 6.50(1H, d, J = 1.0 Hz), 7.62(2H, d, J = 8.3 Hz), 7.99(1H, dd, J = 5.0, 6.8 Hz), 8.07(2H, d, J = 8.4 Hz), 8.56(1H, d, J = 5.0 Hz), 8.70(1H, d, J = 3.1 Hz) | | |
| A091 | (DMSO-d6) 2.10-2.19(1H, m), 2.32-2.37(1H, m), 2.66(3H, s), 3.44(3H, s), 3.67(1H, ddd, J = 3.1, 9.2, 14.2 Hz), 3.73-3.77(2H, m), 3.80-3.86(1H, m), 3.97(1H, ddd, J = 2.2, 9.3, 13.3 Hz), 4.11(1H, dt, J = 3.5, 13.2 Hz), 4.86(1H, dd, J = 3.2, 9.8 Hz), 6.50(1H, d, J = 1.2 Hz), 7.55(2H, d, J = 8.2 Hz), 7.97(2H, d, J = 8.2 Hz), 7.99-8.01(1H, m), 8.57(1H, dd, J = 0.9, 5.0 Hz), 8.70(1H, d, J = 3.1 Hz) | 463 | +8.61 (c = 0.575, CH2Cl2) |
| A092 | (CDCl3) 2.14-2.35(2H, m), 3.41(1H, dd, J = 9.4, 14.1 Hz), 3.56(3H, s), 3.59-3.66 (1H, m), 3.77(1H, dt, J = 5.5, 14.1 Hz), 3.84-3.90(1H, m), 4.03(1H, d, J = 14.9 Hz), 4.25(1H, dt, J = 5.5, 12.5 Hz), 4.89(1H, dd, J = 1.6, 9.4 Hz), 7.08(2H, t, J = 8.6 Hz), 7.26(1H, s), 7.38(2H, dd, J = 5.5, 8.6 Hz), 8.07(1H, d, J = 4.7 Hz), 8.86(1H, d, J = 5.5 Hz), 9.29(1H, s) | 382 | |
| A093 | (DMSO-d6) 2.08-2.17(1H, m), 2.24-2.31(1H, m), 3.43(3H, s), 3.65(1H, ddd, J = 3.0, 9.2, 14.2 Hz), 3.72-3.74(2H, m), 3.74(3H, s), 3.79-3.83(1H, m), 3.92(1H, ddd, J = 2.0, 9.4, 13.3 Hz), 4.08(1H, dt, J = 3.4, 13.3 Hz), 4.72(1H, dd, J = 3.2, 9.7 Hz), 6.49(1H, s), 6.80-6.83(1H, m), 6.91(1H, s), 6.92(1H, d, J = 7.4 Hz), 7.24(1H, t, J = 8.3 Hz), 7.99(1H, dd, J = 5.3, 6.5 Hz), 8.56(1H, d, J = 4.7 Hz), 8.69(1H, d, J = 3.1 Hz) | 411 | |
| A094 | (DMSO-d6) 1.98-2.04(1H, m), 2.23-2.30(1H, m), 3.44(3H, s), 3.61-3.71(3H, m), 3.77(3H, s), 3.82-3.86(1H, m), 3.92(1H, ddd, J = 2.0, 9.5, 13.0 Hz), 4.08(1H, dt, J = 3.3, 13.2 Hz), 4.96(1H, dd, J = 3.1, 9.4 Hz), 6.50(1H, d, J = 1.1 Hz), 6.94(1H, t, J = 7.7 Hz), 6.98(1H, d, J = 8.1 Hz), 7.24(1H, dt, J = 5.0, 6.5 Hz), 7.40(1H, dd, J = 1.2, 7.8 Hz), 8.00(1H, dd, J = 5.0, 6.5 Hz), 8.56(1H, d, J = 5.3 Hz), 8.69(1H, d, J = 3.1 Hz) | 411 | |
| A095 | (DMSO-d6) 2.09-2.25(2H, m), 3.43(3H, s), 3.61-3.68(1H, m), 3.72(2H, t, J = 5.4 Hz), 3.73(3H, s), 3.78-3.82(1H, m), 3.88-3.93(1H, m), 4.05(1H, dt, J = 3.4, 13.4 Hz), 4.68(1H, dd, J = 3.4, 9.6 Hz), 6.49(1H, d, J = 1.0 Hz), 6.88(2H, d, J = 8.8 Hz), 7.27(2H, d, J = 8.6 Hz), 7.99(1H, dd, J = 4.9, 6.6 Hz), 8.57(1H, d, J = 5.1 Hz), 8.70(1H, d, J = 3.1 Hz) | 411 | |
| A096 | (DMSO-d6) 2.09-2.17(1H, m), 2.27-2.33(1H, m), 3.44(3H, s), 3.68(1H, ddd, J = 3.0, 9.2, 13.6 Hz), 3.74-3.75(2H, m), 3.83-3.87(1H, m), 3.95(1H, ddd, J = 2.1, 9.1, 13.4 Hz), 4.09(1H, dt, J = 4.0, 13.4 Hz), 4.77(1H, dd, J = 3.2, 9.7 Hz), 6.91(1H, s), 7.33(2H, d, J = 8.5 Hz), 7.53(2H, d, J = 8.5 Hz), 8.22(1H, dd, J = 1.4, 5.2 Hz), 9.00(1H, d, J = 5.2 Hz), 9.29(1H, d, J = 1.2 Hz) | 442 | +8.10 (c = 0.300, CH2Cl2) |
| A097 | (DMSO-d6) 2.10-2.19(1H, m), 2.32-2.38(1H, m), 2.66(3H, s), 3.44(3H, s), 3.66(1H, ddd, J = 3.1, 9.3, 14.2 Hz), 3.73-3.77(2H, m), 3.82-3.86(1H, m), 3.97(1H, ddd, J = 2.2, 9.4, 13.2 Hz), 4.11(1H, dt, J = 3.3, 13.4 Hz), 4.86(1H, dd, J = 3.2, 9.8 Hz), 6.50(1H, d, J = 1.2 Hz), 7.55(2H, d, J = 8.3 Hz), 7.97(2H, d, J = 8.2 Hz), 7.99(1H, dd, J = 5.0, 6.8 Hz), 8.57(1H, d, J = 4.9 Hz), 8.70(1H, d, J = 3.1 Hz) | 463 | −7.70 (c = 0.435, CH2Cl2) |
| A098 | (DMSO-d6) 2.12-2.20(1H, m), 2.27-2.33(1H, m), 3.44(3H, s), 3.69(1H, ddd, J = 3.0, 9.2, 14.2 Hz), 3.76(2H, t, J = 6..0 Hz), 3.83-3.87(1H, m), 3.92-3.97(1H, m), 4.09(1H, dt, J = 3.6, 13.2 Hz), 4.77(1H, dd, J = 3.1, 9.8 Hz), 6.91(1H, s), 7.13-7.18(2H, m), 7.39-7.42(2H, m), 8.22-8.23(1H, m), 9.00(1H, d, J = 5.0 Hz), 9.29(1H, s) | 382 | |
| A099 | (DMSO-d6) 2.13-2.22(1H, m), 2.33-2.4(1H, m), 3.71(1H, ddd, J = 2.9, 9.2 14.3 Hz), 3.77-3.81(2H, m), 3.86-3.90(1H, m), 3.97-4.04(1H, m), 4.14(1H, dt, J = 3.6, 13.2 Hz), 4.88(1H, dd, J = 3.2, 9.8 Hz), 6.92(1H, s), 7.58(2H, d, J = 8.3 Hz), 8.02(2H, d, J = 8.3 Hz), 8.23(1H, dd, J = 1.3, 5.2 Hz), 9.00(1H, d, J = 5.2 Hz), 9.30(1H, d, J = 1.1 Hz), 9.71(1H, s) | 432 | +9.94 (c = 0.450, CH2Cl2) |
| A100 | (DMSO-d6) 2.14-2.21(1H, m), 2.33-2.39(1H, m), 2.66(3H, s), 3.45(3H, s), 3.67-3.73(1H, m), 3.78-3.80(2H, m), 3.86-3.90(1H, m), 3.97-4.02(1H, m), 4.13(1H, dt, J = 4.1, 13.4 Hz), 4.87(1H, dd, J = 3.3, 9.8 Hz), 6.92(1H, s), 7.56(2H, d, J = 8.3 Hz), 7.97(2H, d, J = 8.3 Hz), 8.23(1H, dd, J = 1.2, 5.1 Hz), 9.00(1H, d, J = 1.2 Hz), 9.30(1H, d, J = 1.3 Hz) | 446 | +9.81 (c = 0.360, CH2Cl2) |
| A101 | (DMSO-d6) 2.12-2.19(1H, m), 2.27-2.33(1H, m), 3.44(3H, s), 3.68(1H, ddd, J = 2.7, 9.0, 14.4 Hz), 3.74(3H, s), 3.74-3.80(2H, m), 3.83-3.87(1H, m), 3.94(1H, ddd, J = 2.3, 9.6, 13.3 Hz), 4.10(1H, dt, J = 3.3, 13.4 Hz), 4.74(1H, dd, J = 3.2, 9.8 Hz), 6.80-6.83(1H, m), 6.91-6.93(3H, m), 7.24(1H, t, J = 8.1 Hz), 8.23(1H, dd, J = 1.2, 5.4 Hz), 9.00(1H, d, J = 4.9 Hz), 9.29(1H, d, J = 1.2 Hz) | 394 | |
| A102 | (DMSO-d6) 1.99-2.05(1H, m), 2.27-2.33(1H, m), 3.44(3H, s), 3.64-3.73(3H, m), 3.77(3H, s), 3.86-3.96(2H, m), 4.11(1H, dt, J = 3.6, 13.2 Hz), 4.97(1H, dd, J = 3.2, 9.4 Hz), 6.91(1H, s), 6.93(1H, t, J = 9.8 Hz), 6.98(1H, d, J = 7.9 Hz), 7.24(2H, dt, J = 1.4, 8.2 Hz), 7.40(1H, dd, J = 1.3, 7.3 Hz), 8.23(1H, dd, J = 0.9, 5.0 Hz), 8.99(1H, d, J = 4.9 Hz), 9.29(1H, d, J = 1.1 Hz) | 394 | |
| A103 | (DMSO-d6) 2.13-2.20(1H, m), 2.33-2.41(1H, m), 2.41(3H, s), 3.45(3H, s), 3.70(1H, ddd, J = 2.8, 9.0, 14.4 Hz), 3.77-3.81(2H, m), 3.83-3.90(1H, m), 4.00(1H, ddd, J = 2.4, 6.9, 13.2 HZ), 4.14(1H, dt, J = 3.7, 13.1 Hz), 4.91(1H, dd, J = 3.3, 9.8 Hz), 6.92(1H, s), 7.62(2H, d, J = 8.3 Hz), 8.07(2H, d, J = 8.3 Hz), 8.23(1H, dd, J = 1.3, 5.2 Hz), 9.00(1H, d, J = 5.2 Hz), 9.29(1H, d, J = 1.2 Hz) | 446 | +11.00 (c = 0.475, CH2Cl2) |
| A104 | (DMSO-d6) 2.09-2.18(1H, m), 2.32-2.36(1H, m), 3.45(3H, s), 3.67(1H, ddd, J = 3.2, 9.2, 14.4 Hz), 3.72-3.77(2H, m), 3.80-3.86(1H, m), 3.94-4.00(1H, m), 4.12(1H, dt, J = 3.2, 13.4 Hz), 4.87(1H, dd, J = 3.1, 9.8 Hz), | 449 | −8.63 (c = 0.295, CH2Cl2) |

TABLE 2-continued

| Comp No. | ¹H-NMR (solvent) δ: | [M + H] | [alpha]D |
|---|---|---|---|
| | 6.50(1H, d, J = 1.1 Hz), 7.58(2H, d, J = 8.3 Hz), 7.98-8.03(3H, m), 8.57(1H, dd, J = 0.7, 4.9 Hz), 8.70(1H, d, J = 3.1 Hz), 9.71(1H, s) | | |
| A105 | (DMSO-d6) 2.19-2.24(1H, m), 2.27-2.32(1H, m), 3.45(3H, s), 3.69(1H, ddd, J = 3.1, 9.4, 14.4 Hz), 3.76-3.80(2H, m), 3.86-3.89(1H, m), 3.97(1H, ddd, J = 2.0, 9.3, 13.2 Hz), 4.12(1H, dt, J = 3.6, 9.5 Hz), 5.00(1H, dd, J = 3.4, 9.6 Hz), 6.92(1H, s), 7.15-7.22(2H, m), 7.30-7.35(1H, m), 7.49-7.53(1H, m), 8.23(1H, dd, J = 1.2, 5.4 Hz), 9.00(1H, d, 4.9 Hz), 9.29(1H, s) | 382 | |
| A106 | (DMSO-d6) 2.11-2.18(1H, m),, 2.31-2.36(11-1, m), 3.45(3H, s), 3.68(1H, ddd, J = 2.7, 8.9, 14.2 Hz), 3.75-3.77(2H, m), 3.83-3.87(1H, m), 3.96(1H, ddd, J = 2.1, 9.2, 13.3 Hz), 4.11(1H, dt, J = 3.7, 13.3 Hz), 4.81(1H, dd, J = 9.8 Hz), 6.91(1H, s), 7.08(1H, dt, J = 2.3, 8.8 Hz), 7.17-7.21(2H, m), 7.35-7.41(1H, m), 8.22(1H, dd, J = 1.3, 5.4 Hz), 9.00(1H, d, J = 5.2 Hz), 9.29(1H, d, J = 1.2 Hz) | 382 | |
| A107 | (DMSO-d6) 2.13-2.21(1H, m), 2.33-2.41(1H, m), 3.46(3H, s), 3.71(1H, ddd, J = 3.2, 9.4, 14.3 Hz), 3.77-3.81(2H, m), 3.86-3.90(1H, m), 4.01(1H, ddd, J = 2.2, 9.4, 13.2 Hz), 4.14(1H, dt, J = 3.8, 13.2 Hz), 4.92(1H, dd, J = 3.2, 9.8 Hz), 6.92(1H, s), 7.64(2H, d, J = 8.3 Hz), 8.10(2H, d, J = 8.4 Hz), 8.23(1H, dd, J = 1.3, 5.1 Hz), 9.00(1H, d, J = 5.2 Hz), 9.10(1H, s), 9.29(1H, d, J = 1.2 Hz) | 432 | +10.01 (c = 0.200, CH2Cl2) |
| A108 | (DMSO-d6) 2.10-2.17(1H, m), 2.24-2.28(1H, m), 3.43(3H, s), 3.62-3.73(3H, m), 3.79-3.83(1H, m), 3.90-3.95(1H, m), 4.07(1H, dt, J = 3.3, 13.4 Hz), 4.76(1H, dd, J = 3.2, 9.9 Hz), 6.49(1H, s), 7.12-7.18(2H, m), 7.38-7.42(2H, m), 7.99(1H, dd, J = 5.3, 6.8 Hz), 8.56(1H, d, J = 5.2 Hz), 9.69(1H, d, J = 3.1 Hz) | 399 | |
| A109 | (DMSO-d6) 2.11-2.18(1H, m), 2.28-2.51(1H, m), 3.43(3H, s), 3.66(1H, ddd, J = 2.8, 9.1, 14.4 Hz), 3.70-3.75(2H, m), 3.74(3H, s), 3.81-3.85(1H, m), 3.90-3.95(1H, m), 4.09(1H, dt, J = 3.5, 13.4 Hz), 4.74(1H, dd, J = 3.2, 9.9 Hz), 6.73(1H, s), 6.80-6.83(1H, m), 6.92-6.93(2H, m), 7.24(1H, t, J = 8.1 Hz), 7.98(2H, d, J = 6.1 Hz), 8.69(2H, d, J = 5.7 Hz) | 393 | |
| A110 | (DMSO-d6) 2.09-2.23(1H, m), 2.26-2.33(1H, m), 3.43(3H, s), 3.67(1H, ddd, J = 3.0, 9.2, 14.4 Hz), 3.73-3.80(2H, m), 3.84-3.88(1H, m), 3.97(1H, ddd, J = 1.9, 9.2, 13.2 Hz), 4.11(1H, dt, J = 3.5, 13.3 Hz), 5.00(1H, dd, J = 3.3, 9.6 Hz), 6.74(1H, s), 7.1 5-7.21(2H, m), 7.30-7.36(1H, m), 7.51(1H, dt, J = 1.3, 7.7 Hz), 7.98(2H, d, J = 6.1 Hz), 8.68(2H, d, J = 6.0 Hz) | 381 | |
| A111 | (DMSO-d6) 2.12-2.23(1H, m), 2.33-2.40(1H, m), 3.46(3H, s), 3.71(1H, ddd, J = 3.0, 9.2, 14.2 Hz), 3.76-3.81(2H, m), 3.86-3.90(1H, m), 3.96-4.02(1H, dt, J = 3.6, 13.1 Hz), 4.14(1H, dt, J = 3.6, 13.1 Hz), 4.88(1H, dd, J = 3.1, 9.8 Hz), 6.92(1H, s), 7.58(2H, d, J = 8.3 Hz), 8.02(2H, d, J = 8.4 Hz), 8.23(1H, dd, J = 1.4, 5.3 Hz), 9.00(1H, dd, J = 1.3, 5.2 Hz), 9.30(1H, d, J = 1.2 Hz), 9.71(1H, s) | 432 | −9.95 (c = 0.190, CH2Cl2) |
| A112 | (DMSO-d6) 2.12-2.21(1H, m), 2.33-2.40(1H, m), 2.66(3H, s), 3.45(3H, s), 3.70(1H, ddd, J = 2.7, 8.8, 14.3 Hz), 3.78-3.80(2H, m), 3.86-3.89(1H, m), 3.99(1H, ddd, J = 2.2, 10.9, 13.3 Hz), 4.13(1H, dt, J = 3.5, 13.3 Hz), 4.87(1H, dd, J = 3.2, 9.8 Hz), 6.91(1H, s), 7.56(2H, d, J = 8.3 Hz), 7.97(2H, d, J = 8.4 Hz), 8.23(1H, dd, J = 1.3, 5.2 Hz), 9.00(1H, d, J = 5.2 Hz), 9.29(1H, d, J = 1.2 Hz) | 446 | −7.95 (c = 0.335, CH2Cl2) |
| A113 | (DMSO-d6) 2.09-2.18(1H, m), 2.32-2.40(1H, m), 2.41(3H, s), 3.44(3H, s), 3.66(1H, ddd, J = 3.2, 9.2, 14.3 Hz), 3.73-3.77(2H, m), 3.82-3.86(1H, m), 3.98(1H, ddd, J = 2.4, 9.4, 13.2 Hz), 4.12(1H, dt, J = 3.2, 13.4 Hz), 4.90(1H, dd, J = 3.4, 10.0 Hz), 6.50(1H, d, J = 1.1 Hz), 7.62(2H, d, J = 8.3 Hz), 7.99(1H, dd, J = 5.0, 6.8 Hz), 8.07(2H, d, J = 8.4 Hz), 8.57(1H, d, J = 4.8 Hz), 8.70(1H, d, J = 3.1 Hz) | 463 | −9.16 (c = 0.385, CH2Cl2) |
| A114 | (DMSO-d6) 2.07-2.14(1H, m), 2.24-2.29(1H, m), 3.43(3H, s), 3.64(1H, ddd, J = 3.2, 9.2, 14.2 Hz), 3.72-3.74(2H, m), 3.79-3.83(1H, m), 3.91-3.96(1H, m), 4.08(1H, dt, J = 4.4, 13.8 Hz), 4.76(1H, dd, J = 3.2, 9.8 Hz), 6.49(1H, d, J = 1.2 Hz), 7.33(2H, d, J = 8.5 Hz), 7.53(2H, d, J = 8.4 Hz), 7.98(1H, dd, J = 5.0, 6.8 Hz), 8.56(1H, dd, J = 0.7, 4.8 Hz), 8.70(1H, d, J = 3.1 Hz) | 459 | +7.56 (c = 0.290, CH2Cl2) |
| A115 | (DMSO-d6) 1.96-2.05(1H, m), 2.27-2.33(1H, m), 3.43(3H, s), 3.62-3.73(3H, m), 3.77(3H, s), 3.85-3.95(2H, m), 4.10(1H, dt, J = 3.3, 13.2 Hz), 4.97(1H, dd, J = 3.1, 9.4 Hz), 6.73(1H, s), 6.93(1H, t, J = 7.7 Hz), 6.98(1H, d, J = 8.1 Hz), 7.24(1H, dt, J = 1.8, 11.8 Hz), 7.40(1H, dd, J = 1.3, 7.7 Hz), 7.98(2H, d, J = 6.0 Hz), 8.68(2H, d, J = 6.0 Hz) | 393 | |
| A116 | (DMSO-d6) 2.11-2.21(1H, m), 2.33-2.41(1H, m), 3.46(3H, s), 3.70(1H, ddd, J = 2.8, 9.0, 14.3 Hz), 3.77-3.81(2H, m), 3.84-3.91(1H, m), 3.97-4.04(1H, m), 4.14(1H, dt, J = 3.9, 9.4 Hz), 4.91(1H, dd, J = 3.2, 9.8 Hz), 6.92(1H, s), 7.64(2H, d, J = 8.3 Hz), 8.11(2H, d, J = 8.4 Hz), 8.23(1H, dd, J = 1.4, 5.2 Hz), 9.00(1H, d, J = 5.2 Hz), 9.10(1H, s), 9.30(1H, d, J = 1.2 Hz) | 432 | −10.78 (c = 0.460, CH2Cl2) |
| A117 | (DMSO-d6) 2.14-2.28(2H, m), 3.44(3H, s), 3.65-3.71(1H, m), 3.73(3H, s), 3.75(2H, t, J = 5.5 Hz), 3.82-3.86(1H, m), 3.90-3.95(1H, m), 4.07(1H, dt, J = 3.3, 13.6 Hz), 4.69(1H, dd, J = 3.5, 9.7 Hz), 6.88(2H, d, J = 8.8 Hz), 6.91(1H, s), 7.28(2H, d, J = 8.6 Hz), 8.22-8.23(1H, m), 9.00(1H, d, J = 4.9 Hz), 9.29(1H, s) | 394 | |
| A118 | (DMSO-d6) 2.13-2.27(2H, m), 3.43(3H, s), 3.66(1H, ddd, J = 3.0, 9.0, 13.8 Hz), 3.72-3.75(5H, m), 3.80-3.75(1H, m), 3.92(1H, ddd, J = 1.8, 8.8, 12.7 Hz), 4.06(1H, dt, J = 3.3, 13.4 Hz), 4.69(1H, dd, J = 3.4, 9.6 Hz), 6.72(1H, s), 6.89(2H, d, J = 8.6 Hz), 7.28(2H, d, J = 8.7 Hz), 7.98(2H, dd, J = 1.4, 4.9 Hz), 8.68(2H, dd, J = 1.3, 5.0 Hz) | 393 | |
| A119 | (DMSO-d6) 2.09-2.25(2H, m), 3.43(3H, s), 3.61-3.68(1H, m), 3.72(2H, t, J = 5.4 Hz), 3.73(3H, s), 3.78-3.82(1H, m), 3.88-3.93(1H, m), 4.05(1H, dt, | 411 | +7.21 (c = 0.260, CH2Cl2) |

TABLE 2-continued

| Comp No. | ¹H-NMR (solvent) δ: | [M + H] | [alpha]D |
|---|---|---|---|
|  | J = 3.4, 13.4 Hz), 4.68(1H, dd, J = 3.4, 9.6 Hz), 6.49(1H, d, J = 1.0 Hz), 6.88(2H, d, J = 8.8 Hz), 7.27(2H, d, J = 8.6 Hz), 7.99(1H, dd, J = 4.9, 6.6 Hz), 8.57(1H, d, J = 5.1 Hz), 8.70(1H, d, J = 3.1 Hz) |  |  |
| A120 | (DMSO-d6) 2.05-2.14(1H, m), 2.24-2.29(1H, m), 3.18(3H, s), 3.65(1H, ddd, J = 3.1, 9.2, 14.3 Hz), 3.72-3.74(2H, m), 3.79-3.83(1H, m), 3.93(1H, ddd, J = 2.2, 9.2, 13.2 Hz), 4.07(1H, dt, J = 3.3, 13.3 Hz), 4.76(1H, dd, J = 3.2, 9.8 Hz), 6.49(1H, d, J = 1.2 Hz), 7.32(2H, d, J = 8.4 Hz), 7.53(2H, d, J = 8.5 Hz), 7.98(1H, dd, J = 5.0, 6.7 Hz), 8.56(1H, dd, J = 0.8, 5.0 Hz), 8.70(1H, d, J = 3.1 Hz) | 459 | −5.62 (c = 0.365, CH2Cl2) |
| A121 | (DMSO-d6) 2.12-2.21(1H, m), 2.33-2.40(11-1, m), 2.41(3H, s), 3.45(3H, s), 3.70(1H, ddd, J = 2.9, 9.2, 14.2 Hz), 3.77-3.81(2H, m), 3.83-3.90(1H, m), 4.00(1H, ddd, J = 2.4, 9.3, 13.2 Hz), 4.14(1H, dt, J = 3.5, 13.5 Hz), 4.91(1H, dd, J = 3.3, 9.8 Hz), 6.92(1H, s), 7.62(2H, d, J = 8.3 Hz), 8.07(2H, d, J = 8.4 Hz), 8.23(1H, dd, J = 1.3, 5.1 Hz), 9.00(1H, d, J = 5.2 Hz), 9.29(1H, d, J = 1.3 Hz) | 446 | −9.26 (c = 0.565, CH2Cl2) |
| A122 | (DMSO-d6) 2.08-2.17(1H, m), 2.27-2.32(1H, m), 3.44(3H, s), 3.68(1H, ddd, J = 3.0, 9.2, 14.2 Hz), 3.74-3.75(2H, m), 3.83-3.87(1H, m), 3.95(1H, ddd, J = 2.3, 9.4, 13.3 Hz), 4.09(1H, dt, J = 3.7, 12.9 Hz), 4.77(1H, dd, J = 3.4, 9.9 Hz), 6.91(1H, s), 7.33(2H, d, J = 8.4 Hz), 7.53(2H, d, J = 8.5 Hz), 8.22(1H, dd, J = 1.4, 5.2 Hz), 9.00(1H, d, J = 5.2 Hz), 9.29(1H, d, J = 1.3 Hz) | 442 | −5.79 (c = 0.295, CH2Cl2) |
| A123 | (DMSO-d6) 2.09-2.19(1H, m), 2.25-2.32(1H, m), 3.43(3H, s), 3.63-3.75(3H, m), 3.81-3.85(1H, m), 3.94(1H, ddd, J = 1.6, 8.7, 11.0 Hz), 4.09(1H, dt, J = 3.8, 13.4 Hz), 4.77(1H, dd, J = 3.1, 9.8 Hz), 6.73(1H, s), 7.13-7.18(2H, m), 7.39-7.42(2H, m), 7.98(2H, dd, J = 1.5, 4.3 Hz), 8.68(2H, dd, J = 1.4, 5.0 Hz) | 381 |  |

Experiment

Inhibitory Activity of the Medicament of the Present Invention Against P-GS1 Phosphorylation by Bovine Cerebral TPK1

A mixture containing 100 mM HEPES-sodium hydroxide (pH 7.2), 1 mM magnesium acetate, 1 mM EGTA, 1 mM dithiothreitol (DTT), 0.02% Tween 20, 7.5 μM P-GS1, 10 μM ATP, human recombinant TPK1 and a compound shown in Table (a final mixture contained 1% DMSO deriving from a solution of a test compound prepared in the presence of 10% DMSO) was used as a reaction system. The phosphorylation was started by adding ATP, and the reaction was conducted at 25° C. for 16 hours. Then equal volume of Kinase Glo Reagent (Promega) was added to the mixture and luminescent signal from the mixture was measured. $IC_{50}$ for each compound was calculated by setting the data of mixture without enzyme as 0% activity and that without compound as 100% activity.

TABLE 3

| Comp No. | IC50/nM |
|---|---|
| A001 | 27.4 |
| A002 | 231.9 |
| A003 | 18.4 |
| A004 | 35.1 |
| A005 | 84.2 |
| A006 | 2.3 |
| A007 | 3.5 |
| A008 | 4.5 |
| A009 | 5.2 |
| A010 | 5.5 |
| A011 | 6 |
| A012 | 6.7 |
| A013 | 7.3 |
| A014 | 8.15 |
| A015 | 9.3 |
| A016 | 10.3 |
| A017 | 11 |
| A018 | 11 |
| A019 | 11.1 |
| A020 | 11.4 |
| A021 | 12 |
| A022 | 12.5 |
| A023 | 12.7 |
| A024 | 13 |
| A025 | 13.7 |
| A026 | 14.6 |
| A027 | 15.4 |
| A028 | 17.6 |
| A029 | 18.8 |
| A030 | 19.8 |
| A031 | 20.2 |
| A032 | 21.6 |
| A033 | 23.4 |
| A034 | 23.5 |
| A035 | 27 |
| A036 | 28.7 |
| A037 | 30.8 |
| A038 | 30.9 |
| A039 | 31.9 |
| A040 | 32.7 |
| A041 | 34.8 |
| A042 | 44.6 |
| A043 | 51 |
| A044 | 52.4 |
| A045 | 57.1 |
| A046 | 61.5 |
| A047 | 67.5 |
| A048 | 68.8 |
| A049 | 70.6 |
| A050 | 77.4 |
| A051 | 80.3 |
| A052 | 92.1 |
| A053 | 100.4 |
| A054 | 110.6 |
| A055 | 164.3 |
| A056 | 169.3 |
| A057 | 207.4 |
| A058 | 221.3 |
| A059 | 240.7 |
| A060 | 252 |
| A061 | 446.2 |
| A062 | 809.4 |
| A063 | 826 |
| A064 | 23.2 |

TABLE 3-continued

| Comp No. | IC50/nM |
| --- | --- |
| A065 | 97.5 |
| A066 | 5.5 |
| A067 | 9.7 |
| A068 | 9.8 |
| A069 | 14.7 |
| A070 | 17.3 |
| A071 | 41 |
| A072 | 65 |
| A073 | 195 |
| A074 | 1.2 |
| A075 | 1.4 |
| A076 | 3.1 |
| A077 | 5.9 |
| A078 | 7.1 |
| A079 | 7.3 |
| A080 | 10.8 |
| A081 | 12.9 |
| A082 | 13.2 |
| A083 | 14 |
| A084 | 15 |
| A085 | 16.7 |
| A086 | 35.8 |
| A087 | 80.1 |
| A088 | 175.8 |
| A089 | 5.4 |
| A090 | 6.1 |
| A091 | 6.8 |
| A092 | 8.3 |
| A093 | 9.65 |
| A094 | 10.35 |
| A095 | 10.65 |
| A096 | 10.8 |
| A097 | 11.3 |
| A098 | 13.8 |
| A099 | 14.7 |
| A100 | 15 |
| A101 | 15.3 |
| A102 | 16.3 |
| A103 | 16.3 |
| A104 | 17.2 |
| A105 | 18.7 |
| A106 | 20.5 |
| A107 | 23 |
| A108 | 24.57 |
| A109 | 28 |
| A110 | 29.2 |
| A111 | 29.5 |
| A112 | 30 |
| A113 | 30 |
| A114 | 34.7 |
| A115 | 47.6 |
| A116 | 48 |
| A117 | 54.7 |
| A118 | 58.6 |
| A119 | 72.2 |
| A120 | 82.8 |
| A121 | 83.4 |
| A122 | 114.4 |
| A123 | 153.1 |

Formulation Example (1) Tablets

The ingredients below were mixed by an ordinary method and compressed by using a conventional apparatus.

| | |
| --- | --- |
| Compound of the present invention (prepared in Preparation Example) | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
| --- | --- |
| Compound of the present invention (prepared in Preparation Example) | 30 mg |
| Olive oil | 300 mg |
| Lecithin | 20 mg |

Industrial Applicability

The compounds of the present invention have TPK1 inhibitory activity and are useful as an active ingredient of a medicament for preventive and/or therapeutic treatment of diseases caused by abnormal advance of TPK1 such as neurodegenerative diseases (e.g. Alzheimer disease) and the above-mentioned diseases.

The invention claimed is:

1. A compound represented by the following formula (I) or a pharmaceutically acceptable salt thereof:

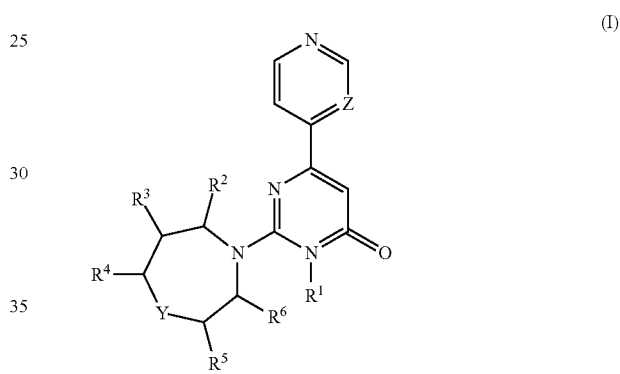

(I)

wherein Z represents nitrogen atom or C—F;
$R^1$ represents a $C_1$-$C_3$ alkyl group;
Y represents an oxygen atom;
$R^2$, $R^3$, $R^4$, $R^5$, and $R^6$ may be the same or different and each independently represents hydrogen atom, a $C_1$-$C_6$ alkyl group, or a group represented by the following formula (II):

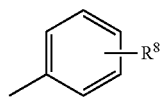

(II)

wherein $R^8$ represents hydrogen atom, a halogen atom, cyano group, nitro group, a $C_1$-$C_6$ alkyl group, or a group represented by any one of the following formulas (IIIa) to (IIIh):

—O—$R^9$ (IIIa)

 (IIIb)

-continued

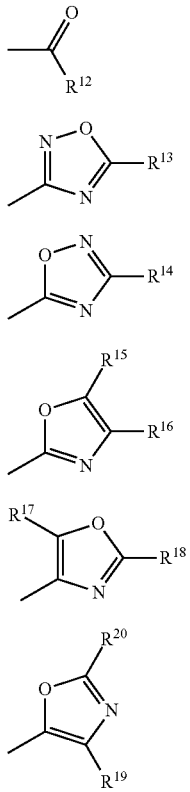

wherein R⁹ represents hydrogen atom or a $C_1$-$C_6$ alkyl group;
$R^{11}$, $R^{13}$, $R^{14}$, $R^{15}$, $R^{16}$, $R^{17}$, $R^{18}$, $R^{19}$ and $R^{20}$ may be the same or different and each independently represents hydrogen atom, a $C_1$-$C_6$ alkyl group, or a $C_6$-$C_{10}$ aryl group;
$R^{12}$ K represents hydrogen atom, hydroxyl group, amino group, a $C_1$-$C_6$ alkyl group, a $C_1$-$C_3$ alkyloxy group, a $C_1$-$C_3$ alkylamino group, a di($C_1$-$C_3$ alkyl)amino group, or a $C_6$-$C_{10}$ aryl group;
$R^{10}$ represents hydrogen atom or a group represented by the following formula(IV):

-A-R²¹ (IV)

wherein A represents —(CH₂)ₚ—, —CO—, or —SO₂—, wherein p represents an integer of 1 to 3;
$R^{21}$ represents hydrogen atom, a $C_1$-$C_3$ alkyl group, —OR²², —NR²³R²⁴, or a $C_6$-$C_{10}$ aryl group:
wherein $R^{22}$, $R^{23}$ and $R^{24}$ may be the same or different and each independently represents hydrogen atom, a $C_1$-$C_6$ alkyl group, a $C_1$-$C_6$ alkenyl group, or a $C_6$-$C_{10}$ aryl-methyl group;
or $R^{10}$ and $R^{11}$ may be combined to each other to form a heterocyclic group together with the nitrogen atom to which $R^{10}$ and $R^{11}$ bind to; and
wherein each of at least four substituents selected from the group consisting of $R^2$, $R^3$, $R^4$, $R^5$, and $R^6$ is a hydrogen atom.

2. The compound or a pharmaceutically acceptable salt thereof according to claim 1, wherein $R^2$, $R^3$, $R^4$, $R^5$ and $R^6$ may be the same or different and is each independently hydrogen atom, a $C_1$-$C_6$ alkyl group or a group represented by the formula (II), wherein $R^8$ is hydrogen atom, a halogen atom, cyano group, a $C_1$-$C_6$ alkyl group, or a group represented by any one of the formula (IIIa), (IIIc), (IIId), and (IIIe).

3. A compound which is selected from the group consisting of:
(S)-2-[6-(4-Bromo-phenyl)-[1,4]oxazepan-4-yl]-1-methyl-1H-[4,4']bipyrimidinyl-6-one;
2-(6-phenyl-[1,4]oxazepan-4-yl)-1-methyl-1H-[4,4']bipyrimidinyl-6-one;
6-(3-Fluoro-pyridin-4-yl)-3-methyl-2-(2-phenyl-[1,4]oxazepan-4-yl)-3H-pyrimidin-4-one;
(S)-2-[6-(4-cyano-phenyl)-[1,4]oxazepan-4-yl]-1-methyl-1H-[4,4']bipyrimidinyl-6-one;
(S)-4-{4-[4-(3-Fluoro-pyridin-4-yl)-1-methyl-6-oxo-1,6-dihydro-pyrimidin-2-yl]-[1,4]oxazepan-2-yl}-benzamide;
(S)-2-[2-(3-Bromo-phenyl)-[1,4]oxazepan-4-yl]-6-(3-fluoro-pyridin-4-yl)-3-methyl-3H-pyrimidin-4-one;
(S)-2-[2-(4-Bromo-phenyl)-[1,4]oxazepan-4-yl]-1-methyl-1H-[4,4']bipyrimidinyl-6-one;
(+)-6-(3-Fluoro-pyridin-4-yl)-3-methyl-2-[7-(4-[1,2,4]oxadiazol-3-yl-phenyl)-[1,4]oxazepan-4-yl]-3H-pyrimidin-4-one;
6-(3-Fluoro-pyridin-4-yl)-3-methyl-2-(5-phenyl-[1,4]oxazepan-4-yl)-3H-pyrimidin-4-one;
(S)-2-[2-(4-Bromo-phenyl)-[1,4]oxazepan-4-yl]-6-(3-fluoro-pyridin-4-yl)-3-methyl-3H-pyrimidin-4-one;
6-(3-Fluoro-pyridin-4-yl)-3-methyl-2-{6-[4-(3-methyl-[1,2,4]oxadiazol-5-yl)-phenyl]-[1,4]oxazepan-4-yl}-3H-pyrimidin-4-one;
(S)-2-[2-(4-Fluoro-phenyl)-[1,4]oxazepan-4-yl]-6-(3-fluoro-pyridin-4-yl)-3-methyl-3H-pyrimidin-4-one;
(+)-6-(3-Fluoro-pyridin-4-yl)-3-methyl-2-{7-[4-(3-methyl-[1,2,4]oxadiazol-5-yl)-phenyl]-[1,4]oxazepan-4-yl}-3H-pyrimidin-4-one;
(S)-3-{4-[4-(3-Fluoro-pyridin-4-yl)-1-methyl-6-oxo-1,6-dihydro-pyrimidin-2-yl]-[1,4]oxazepan-2-yl}-benzamide;
(+)-6-(3-Fluoro-pyridin-4-yl)-3-methyl-2-{7-[4-(5-methyl-[1,2,4]oxadiazol-3-yl)-phenyl]-[1,4]oxazepan-4-yl}-3H-pyrimidin-4-one;
6-(3-Fluoro-pyridin-4-yl)-3-methyl-2-[6-(4-[1,2,4]oxadiazol-3-yl-phenyl)-[1,4]oxazepan-4-yl]-3H-pyrimidin-4-one;
(S)-2-[2-(3-Bromo-phenyl)-[1,4]oxazepan-4-yl]-1-methyl-1H-[4,4']bipyrimidinyl-6-one;
(S)-2-[2-(4-cyano-phenyl)-[1,4]oxazepan-4-yl]-6-(3-fluoro-pyridin-4-yl)-3-methyl-3H-pyrimidin-4-one;
2-[7-(2-Fluoro-phenyl)-[1,4]oxazepan-4-yl]-6-(3-fluoro-pyridin-4-yl)-3-methyl-3H-pyrimidin-4-one;
(S)-2-[2-(4-Fluoro-phenyl)-[1,4]oxazepan-4-yl]-1-methyl-1H-[4,4']bipyrimidinyl-6-one;
(S)-3-[4-(1-Methyl-6-oxo-1,6-dihydro-[4,4']bipyrimidinyl-2-yl)-[1,4]oxazepan-2-yl]-benzamide;
6-(3-Fluoro-pyridin-4-yl)-2-[7-(3-methoxy-phenyl)-[1,4]oxazepan-4-yl]-3-methyl-3H-pyrimidin-4-one;
6-(3-Fluoro-pyridin-4-yl)-3-methyl-2-(5-methyl-[1,4]oxazepan-4-yl)-3H-pyrimidin-4-one; and
(R)-6-(3-Fluoro-pyridin-4-yl)-3-methyl-2-(5-methyl-[1,4]oxazepan-4-yl)-3H-pyrimidin-4-one;
or a pharmaceutically acceptable salt thereof.

4. A composition comprising as an active ingredient the compound or a pharmaceutically acceptable salt thereof according to claim 1, and further comprising one or more pharmaceutical additives.

* * * * *

UNITED STATES PATENT AND TRADEMARK OFFICE
CERTIFICATE OF CORRECTION

PATENT NO. : 9,108,957 B2  
APPLICATION NO. : 13/262396  
DATED : August 18, 2015  
INVENTOR(S) : K. Watanabe et al.

Page 1 of 1

It is certified that error appears in the above-identified patent and that said Letters Patent is hereby corrected as shown below:

IN THE CLAIMS

Column 113, line 40 (claim 1, line 20) please change "$R^{12}K$ represents" to -- $R^{12}$ represents --

Signed and Sealed this  
First Day of March, 2016

Michelle K. Lee  
*Director of the United States Patent and Trademark Office*